US009981990B2

(12) United States Patent
Janganati et al.

(10) Patent No.: US 9,981,990 B2
(45) Date of Patent: May 29, 2018

(54) MELAMPOMAGNOLIDE B DIMERS

(71) Applicant: BioVentures, LLC, Little Rock, AR (US)

(72) Inventors: Venumadhav Janganati, Little Rock, AR (US); Peter Crooks, Little Rock, AR (US); Narsimha Reddy Penthala, Little Rock, AR (US); Craig Jordan, Denver, CO (US); Shobanbabu Bommagani, Little Rock, AR (US); Jessica Ponder, Denver, CO (US)

(73) Assignees: BIOVENTURES, LLC, Little Rock, AR (US); THE REGENTS OF THE UNIVERSITY OF COLORADO, A BODY CORPORATE, Denver, CO (US)

(*) Notice: Subject to any disclaimer, the term of this patent is extended or adjusted under 35 U.S.C. 154(b) by 0 days. days.

(21) Appl. No.: 15/532,413

(22) PCT Filed: Dec. 3, 2015

(86) PCT No.: PCT/US2015/063792
§ 371 (c)(1),
(2) Date: Jun. 1, 2017

(87) PCT Pub. No.: WO2016/090166
PCT Pub. Date: Jun. 9, 2016

(65) Prior Publication Data
US 2017/0362254 A1  Dec. 21, 2017

Related U.S. Application Data

(60) Provisional application No. 62/086,864, filed on Dec. 3, 2014.

(51) Int. Cl.
*C07D 519/00* (2006.01)
*C07F 7/18* (2006.01)

(52) U.S. Cl.
CPC .......... *C07D 519/00* (2013.01); *C07F 7/1852* (2013.01)

(58) Field of Classification Search
CPC .......................... C07D 519/00; C07F 7/1852
See application file for complete search history.

(56) References Cited

U.S. PATENT DOCUMENTS

| 4,241,046 | A | 12/1980 | Papahadjopoulos |
| 4,394,448 | A | 7/1983 | Szoka et al. |
| 4,529,561 | A | 7/1985 | Hunt et al. |
| 4,755,388 | A | 7/1988 | Heath et al. |
| 4,828,837 | A | 5/1989 | Uster et al. |
| 4,925,661 | A | 5/1990 | Huang |
| 4,954,345 | A | 9/1990 | Mueller |
| 4,957,735 | A | 9/1990 | Huang |
| 5,043,164 | A | 8/1991 | Huang et al. |
| 5,064,655 | A | 11/1991 | Uster et al. |
| 5,077,211 | A | 12/1991 | Yarosh |
| 5,264,618 | A | 11/1993 | Felgner et al. |
| 7,312,242 | B2 | 12/2007 | Crooks et al. |
| 7,678,904 | B2 | 3/2010 | Crooks et al. |
| 8,884,027 | B2 | 11/2014 | Crooks et al. |
| 9,469,650 | B2 | 10/2016 | Janganati et al. |
| 9,487,536 | B2 | 11/2016 | Bommagani et al. |
| 2007/0015161 | A1 | 1/2007 | Echeverri et al. |
| 2007/0111203 | A1 | 5/2007 | Cao et al. |
| 2009/0312298 | A1 | 12/2009 | Bamber et al. |
| 2011/0092762 | A1 | 4/2011 | Wong et al. |
| 2012/0122943 | A1 | 5/2012 | Crooks et al. |
| 2014/0045821 | A1 | 2/2014 | Wipf et al. |
| 2015/0133444 | A1 | 5/2015 | Janganati et al. |
| 2015/0203508 | A1 | 7/2015 | Bommagani et al. |
| 2016/0077084 | A1 | 3/2016 | MacNicol et al. |
| 2016/0083397 | A1 | 3/2016 | Penthala et al. |
| 2016/0368928 | A1 | 12/2016 | Bommagani et al. |
| 2016/0368929 | A1 | 12/2016 | Janganati et al. |

FOREIGN PATENT DOCUMENTS

| EP | 2125859 B1 | 5/2013 |
| WO | 2008022104 A1 | 2/2008 |
| WO | 2012145678 A1 | 10/2012 |
| WO | 2013019561 A1 | 2/2013 |
| WO | 2014172607 A1 | 10/2014 |
| WO | 2014172608 A2 | 10/2014 |
| WO | 2016090166 A1 | 6/2016 |
| WO | 2017132528 A1 | 8/2017 |

OTHER PUBLICATIONS

Acton, E. et al., "Anticancer Specificity of Some Ellipticinium Salts against Human Brain Tumors in Vitro," J. Med. Chem., 1994, pp. 2185-2189, vol. 37.
Bork, P. et al., "Sesquiterpene lactone containing Mexican Indian medicinal plants and pure sesquiterpene lactones as potent inhibitors of transcription factor NF-kB," FEBS Letters, 1997, pp. 85-90, vol. 402, Federation of European Biochemical Societies.
Boyd, M. et al., "Some Practical Considerations and Applications of the National Cancer Institute In Vitro Anticancer Drug Discovery Screen," Drug Development Research, 1995, 13 pgs., vol. 34.
Brouwers, L. et al., "Network Neighbors of Drug Targets Contribute to Drug Side-Effect Similarity," PloS One, Jul. 2011, pp. 1-7, vol. 6, Issue 7, No. 222187.
Cha, H. et al., "Evoluntionarily Repurposed Networks Reveal the Well-Known Antifungal Drug Thiabendazole to be a Novel Vascular Disrupting Agent," PLOS Biol., Aug. 2012, pp. 1-13, vol. 10, Issue 8, No. e1001379.

(Continued)

*Primary Examiner* — Timothy R Rozof
(74) *Attorney, Agent, or Firm* — Polsinelli PC

(57) ABSTRACT

The present disclosure provides dimers of melampomagnolide B (MMB), including carbamate, carbonate, succinic amide, ester and carboxamide dimers of MMB. These derivatives are useful for treating cancer in humans, in particular in treating leukemia, including acute myelogenous leukemia (AML). A compound comprising Formula (1) wherein: Z is independently selected from the group consisting of $CH_2$, O, C(O), and CH, wherein when Z is CH, Z is connected to Y via a double bond and Y is N.

11 Claims, 7 Drawing Sheets

(56) References Cited

OTHER PUBLICATIONS

Cotarca, L. et al., "Bis(trichloromethyl) Carbonate in Organic Synthesis," Synthesis, Jan. 1, 1996, pp. 553-576, vol. 1996, No. 5, Georg Thieme Verlag KG.

Dai, Y. et al., "The NF (Nuclear factor)-kB inhibitor parthenolide interacts with histone deacetylase inhibitors to induce MKK7/JNK1-dependent apoptosis in human acute myeloid leukaemia cells," British Journal of Haematology, Aug. 4, 2010, pp. 70-83, vol. 151, Blackwell Publishing Ltd.

De Groot, F. et al., "Synthesis and Biological Evaluation of 2'-Carbamate-Linked and 2'-Carbonate-Linked Prodrugs of Paclitaxel: Selective Activation by the Tumor-Associated Protease Plasmin," J. Med. Chem., 2000, pp. 3093-3102, vol. 43.

Dell'Agli, M. et al., "Inhibition of NF-kB and metalloproteinase-9 expression and secretion by parthenolide derivatives," Bioorganic & Medicinal Chemistry Letters, 2009, pp. 1858-1860, vol. 19, Elsevier Ltd.

Deschler, B. et al., "Acute Myeloid Leukemia: Epidemiology and Etiology," Cancer, Nov. 1, 2006, pp. 2099-2107, vol. 107, No. 9, Wiley Interscience.

Deshpande, A. et al., "Insulin Induction of Xenopus laevis Oocyte Maturation is Inhibited by Monoclonal Antibody against p21 ras Proteins," Mol. Cell. Biol., Mar. 1987, pp. 1285-1288, vol. 7, No. 3.

Deshpande, A. et al "In vitro Induction of Germinal Vesicle Breakdown in Xenopus laevis Oocytes in Melittin," Differentiation, 1982, pp. 127-132, vol. 21, Springer-Verlag.

El-Feraly, F., "Melampolides From Magnolia Grandiflora," Phytochemistry, 1984, pp. 2372-2374, vol. 23, No. 10, Pergamon Press Ltd., Great Britain.

Estey, E. et al., "Acute myeloid leukaemia," Lancet, Nov. 25, 2006, pp. 1894-1907, vol. 368.

Ghantous, A. et al., "What made sesquiterpene lactones reach cancer clinical trials?", Drug Discovery Today, Aug. 2010, pp. 668-678, vol. 15, Nos. 15/16, Elsevier Ltd.

Gopal, Y.N. et al., "Parthenolide Specifically Depletes Histone Deacetylase 1 Protein and Induces Cell Death through Ataxia Telangiectasia Mutated," Chemistry & Biology, Jul. 2007, pp. 813-823, vol. 14, Elsevier Ltd.

Guo, Y., "The Role of Aven in Cell Cycle Regulation," Dissertation, Department of Pharmacology and Cancer Biology, Duke University, Aug. 13, 2008, pp. 1-147, (166 total pgs.), ProQuest, LLC.

Guzman, M. et al., "The sesquiterpene lactone parthenolide induces apoptosis of human acute myelogenous leukemia stem and progenitor cells," Blood, Jun. 1, 2005, pp. 4163-4169, vol. 105, No. 11.

Guzman, M. et al., "Feverfew: weeding out the root of leukaemia," Expert Opin. Biol. Ther., 2005, pp. 1147-1152, vol. 5, No. 9, Ashley Publications Ltd.

Guzman, M. et al., "An orally bioavailable pathenolide analog selectively eradicates acute myelogenous leukemia stem and progenitor cells," Blood, Dec. 15, 2007, pp. 4427-4435, vol. 110, No. 13.

Hall, I. et al., "Anti-Inflammatory Activity of Sesquiterpene Lactones and Related Compounds," J. Pharmaceutical Sciences, May 1979, pp. 537-542, vol. 68, No. 5.

Han, C. et al., "Semisynthetic Derivatives of Sesquiterpene Lactones by Palladium-Catalyzed Arylation of the alpha-Methylene-gamma-lactone Substructure," J. Org. Chem., 2009, pp. 7176-7179, vol. 74.

Hassane, D. et al., "Chemical genomic screening reveals synergism between parthenolide and inhibitors of the PI-3 kinase and mTOR pathways," Blood, Dec. 23, 2010, pp. 5983-5990, vol. 116, No. 26.

Hehner, S. et al., "Sesquiterpene Lactones Specifically Inhibit Activation of NF-kB by Preventing the Degradation of IkB-alpha and IkB-beta," J. Biol. Chem., 1998, pp. 1288-1297, vol. 273, No. 3.

Heptinstall, S. et al., "Inhibition of Platelet Behaviour by Feverfew: a Mechanism of Action Involving Sulphydryl Groups," Folia Haematol., 1988, pp. 447-449, vol. 115, No. 4.

Hewamana, S. et al., "The Nf-kB subunit Rel A is associated with in vitro survival and clinical disease progression in chronic lymphocytic leukemia and represents a promising therapeutic target," Blood, May 1, 2008, pp. 4681-4689, vol. 111, No. 9.

OncoLink, "Cancer Types," http://www.oncolink.org/cancers, 2017, pp. 1-17, Trustees of the University of Pennsylvania.

International Search Report and Written Opinion dated Feb. 5, 2016 from related International Patent Application No. PCT/US2015/063792; 10 pgs.

International Search Report and Written Opinion dated Nov. 7, 2014 from related International Patent Application No. PCT/US2014/034605; 11 pgs.

International Search Report and Written Opinion dated Sep. 12, 2014 from related International Patent Application No. PCT/US2014/034604; 9 pgs.

International Search Report and Written Opinion dated Apr. 25, 2017 from related International Patent Application No. PCT/US2017/015376; 13 pgs.

Kim, Y. et al., "Resistance of cholangiocarcinoma cells to parthenolide-induced apoptosis by the excretory-secretory products of Clonorchis sinensis," Parasitol. Res., 2009, pp. 1011-1016, vol. 104, Springer.

Kim, Y. et al., "Myeloperoxidase Expression as a Potential Determinant of Parthenolide-Induced Apoptosis in Leukemia Bulk and Leukemia Stem Cells," JPET, 2010, pp. 389-400, vol. 335, No. 2.

Knight, D. "Feverfew: Chemistry and Biological Activity," Natural Products Reports, 1995, pp. 271-276.

Kodadek, T. et al., "Optimized protocols for the isolation of specific protein-binding peptides or peptoids from combinatorial libraries displayed on beads," Mol. BioSyst., 2006, pp. 25-35, vol. 2, the Royal Society of Chemistry.

Kolev, J. et al., "Discovery of potent parthenolide-based antileukemic agents enabled by late-stage P450-mediated C—H functionalization," NIH Public Access, Author Manuscript, 2015, pp. 1-22, published in final edited form as: ACS Chem. Biol., Jan. 17, 2014, pp. 164-173, vol. 9, No. 1.

Lowenberg, B. et al., "Mitoxantrone Versus Daunorubicin in Induction-Consolidation Chemotherapy—The Value of Low-Dose Cytarabine for Maintenance of Remission, and an Assessment of Prognostic Factors in Acute Myeloid Leukemia in the Elderly: Final Report of the Leukemia Cooperative Group of the European Organization for the Research and Treatment of Cancer and the Dutch-Belgian Hemato-Oncology Cooperative Hovon Group Randomized Phase III Study AML-9," J. Clin. Oncol., 1998, pp. 872-881, vol. 16, No. 3.

Macias, F. et al., "Potential Allelopathic Activity of Several Sesquiterpene Lactone Models," Phytochemistry, 1992, pp. 1969-1977, vol. 31, No. 6, Pergamon Press Ltd., Great Britain.

Mood, K. et al., "Contribution of JNK, Mek, Mos and PI-3K signaling to GVBD in Xenopus oocytes," Cellular Signaling, 2004, pp. 631-642, vol. 16, Elsevier Inc.

Moumou, M. et al., "Access to new sequiterpenoids by catalytic acid rearrangement of 9alpha-hydroxyparthenolide," Tetrahedron Lett., 2012, pp. 3000-3003, vol. 53, Elsevier Ltd.

Nasim, S. et al., "Antileukemic activity of aminoparthenolide analogs," Bioorg. Med. Chem. Lett., 2008, pp. 3870-3873, vol. 18, Elsevier Ltd.

Nasim, S. et al., "Melampomagnolide B: A new antileukemic sesquiterpenes" Bioorg. Med. Chem., 2011, pp. 1515-1519, vol. 19, Elsevier Ltd.

Neelakantan, S. et al., "Aminoparthenolides as novel anti-leukemic agents: Discovery of the NF-kB inhibitor, DMAPT (LC-1)," Bioorg. Med. Chem. Lett., 2009, pp. 4346-4349, vol. 19, Elsevier Ltd.

Neukirch, H. et al., "Transannular Cyclization in Cyclodecenes: The Case Study of Melampolides," Eur. J. Org. Chem., 2003, pp. 3969-3975, Wiley-VCH Verlag GmbH & Co. KGaA, Weinheim.

Notice of Allowance dated Jun. 7, 2016 from related U.S. Appl. No. 14/537,389; 9 pgs.

Notice of Allowance dated Jun. 8, 2016 from related U.S. Appl. No. 14/676,537; 8 pgs.

(56) References Cited

OTHER PUBLICATIONS

Nozaki, S. et al., "Repression of GADD153/CHOP by NF-kB: a possible cellular defense against endoplasmic reticulum stress-induced cell death," Oncogene, 2001, pp. 2178-2185, vol. 20, Nature Publishing Group.
Office Action dated Oct. 5, 2015 from related U.S. Appl. No. 14/537,389; 10 pgs.
Office Action dated Mar. 11, 2016 from related U.S. Appl. No. 14/537,389; 8 pgs.
Office Action dated Feb. 8, 2016 from related U.S. Appl. No. 14/676,537; 19 pgs.
Office Action dated Jul. 29, 2016 from related U.S. Appl. No. 14/785,196; 12 pgs.
Office Action dated Jan. 25, 2017 from related U.S. Appl. No. 14/785,196; 20 pgs.
Office Action dated Jun. 1 2017 from related U.S. Appl. No. 14/785,196; 17 pgs.
Office Action dated Jun. 9, 2016 from related U.S. Appl. No. 14/785,183; 18 pgs.
Office Action dated Feb. 13, 2017 from related U.S. Appl. No. 14/785,183; 12 pgs.
Office Action dated Aug. 9, 2017 from related U.S. Appl. No. 15/251,889; 16 pgs.
Office Action dated Aug. 9, 2017 from related U.S. Appl. No. 15/254,849; 16 pgs.
Office Action dated Oct. 18, 2017 from related U.S. Appl. No. 14/785,196; 16 pgs.
Oka, D. et al., "Sesquiterpene lactone parthenolide suppresses tumor growth in a xenograft model of renal cell carcinoma by inhibiting the activation of NF-kB," Int. J. Cancer, 2007, pp. 2576-2581, vol. 120, Wiley-Liss, Inc.
Okada, L et al., "Stabilization of Actin Filaments Prevents Germinal Vesicle Breakdown and Affects Microtubule Organization in Xenopus Oocytes," Cytoskeleton, May 2012, pp. 312-323, vol. 69, Wiley Periodicals, Inc.
Papke, R. et al., "The pharmacological activity of nicotine and nornicotine on nAChRs subtypes: relevance to nicotine dependence and drug discovery," J. Neurochem., 2007, pp. 160-167, vol. 101.
Pei, S. et al., "Targeting Aberrant Glutathione Metabolism to Eradicate Human Acute Myelogenous Leukemia Cells," J. Biol. Chem., Nov. 22, 2013, pp. 33542-33558, vol. 288, No. 47.
Penthala, N. et al., "Heck products of parthenolide and melampomagnolide-B as anticancer modulators that modify cell cycle progression," European Journal of Medicinal Chemistry, 2014, pp. 517-525, vol. 85, Elsevier Masson SAS.
Pfaffenrath, V. et al., "The efficacy and safety of Tanacetum parthenium (feverfew) in migraine prophylaxis—a double-blind, multicentre, randomized placebo-controlled dose-response study," Cephalalgia, 2002, pp. 523-532, vol. 22, Blackwell Science Ltd., London.
PUBCHEM, Compound Summary for CID 44255396, Nov. 16, 2009; 3 pgs.
Ralstin, M. et al., "Parthenolide Cooperates with NS398 to Inhibit Growth of Human Hepatocellular Carcinoma Cells through Effects on Apoptosis and G0-G1 Cell Cycle Arrest," Mol. Cancer Res., Jun. 2006, pp. 387-399, vol. 4, No. 6.
Restriction Requirement with Notice of References Cited dated Oct. 6, 2015 from related U.S. Appl. No. 14/676,537; 11 pgs.
Riganti, C. et al., "Artemisinin induces doxorubicin resistance in human colon cancer cells via calcium-dependent activation of HIF-1alpha and P-glycoprotein overexpression," British Journal of Pharmacology, 2009, pp. 1054-1066, vol. 156.
Saadane, A. et al., "Parthenolide inhibits ERK and AP-1 which are dysregulated and contribute to excessive IL-8 expression and secretion in cystic fibrosis cells," J. Inflammation, 2011, pp. 1-15, vol. 8, No. 26, BioMed Central.
Sharma, G. et al., "Synthesis and Structure of alpha/delta-Hybrid Peptides—Access to Novel Helix Patterns in Foldamers," Chem. Eur. J., 2009, pp. 5552-5566, vol. 15, Wiley-VCH Verlag GmbH & Co. KgaA, Weinheim.
Sharma, G. et al., "Theoretical and Experimental Studies on alpha/E-Hybrid Peptides: Design of a 14/12-Helix from Peptides with Alternating (S)-C-Linked Carbo-E-amino Acid [(S)-E-Caa(x)] and L-Ala," J. Org. Chem., 2009, pp. 3703-6713, vol. 74, No. 17.
Skalska, J. et al., "Modulation of Cell Surface Protein Free Thiols: A Potential Novel Mechanism of Action of the Sesquiterpene Lactone Parthenolide," PLoS One, Dec. 2009, pp. 1-8, vol. 4, Issue 12, No. e8115.
Staab, H., "New Methods of Preparative Organic Chemistry IV. Syntheses Using Heterocyclic Amides (Azolides)," Angew. Chem. Internat. Edit, 1962, pp. 351-367, vol. 1, No. 7.
Sugimoto, H. et al., "Activation of Dithiocarbamate by 2-Halothiazolium Salts," J. Org. Chem., 1988, pp. 2263-2267, vol. 53, No. 10.
Sweeney, C. et al., "Nuclear Factor-kB Is Constitutively Activated in Prostate Cancer In vitro and is Overexpressed in Prostatic Intraepithelial Neoplasia and Adenocarcinoma of the Prostate," Clin. Cancer Res., Aug. 15, 2004, pp. 5501-5507, vol. 10.
Tazzari, P. et al., "Multidrug resistance-associated protein 1 expression is under the control of the phosphoinositide 3 kinase/Akt signal transduction network in human acute myelogenous leukemia blasts," Leukemia, 2007, pp. 427-438, vol. 21, Nature Publishing Group.
Wen, J. et al., "Oxidative Stress-mediated Apoptosis. The Anticancer Effect of the Sesquiterpene Lactone Parthenolide," J. Biol. Chem., 2002, pp. 38954-38964, vol. 277, No. 41.
Wheeler, G. et al., "Xenopus: An Ideal System for Chemical Genetics," Genesis, 2012, pp. 207-218, vol. 50, Wiley Periodicals, Inc.
Won, Y-K. et al., "Parthenolide sensitizes ultraviolet (UV)-B-induced apoptosis via protein kinase C-dependent pathways," Carcinogenesis, 2005, pp. 2149-2156, vol. 26, No. 12, Oxford University Press.
Woods, J. et al., "Fluorinated Amino-Derivatives of the Sesquiterpene Lactone, Parthenolide, as 19F NMR Probes in Deuterium-Free Environments," J. Med. Chem., 2011, pp. 7934-7941, vol. 54, ACS Publications.
Yip-Schneider, M. et al., "Parthenolide and sulindac cooperate to mediate growth suppression and inhibit the nuclear factor-kB pathway in pancreatic carcinoma cells," Mol. Cancer Ther., Apr. 2005, pp. 587-594, vol. 4, No. 4.
Zhai, J. et et al., "Biomimetic Semisynthesis of Arglabin from Parthenolide," J. Org. Chem., 2012, pp. 7103-7107, vol. 77, American Chemical Society.
Zhang, Q. et al., "Guaianolide Sesquiterpene Lactones, a Source to Discover Agents That Selectively Inhibit Acute Myelogenous Leukemia Stem and Progenitor Cells," J. Med. Chem., 2012, pp. 8757-8769, vol. 55, American Chemical Society.
Zhu, T. et al., "Differential Recognition of ACE Inhibitors in Xenopus Laevis Oocytes Expressing Rat PEPT1 and PEPT2," Pharmaceutical Res., 2000, pp. 526-532, vol. 17, No. 5, Plenum Publishing Corporation.

MELAMPOMAGNOLIDE B DIMERS

CROSS REFERENCE TO RELATED APPLICATIONS

This application claims the benefit of U.S. Provisional Application No. 62/086,864, filed Dec. 3, 2014, the disclosures of which is hereby incorporated by reference in its entirety.

GOVERNMENTAL RIGHTS

This invention was made with government support under R01CA158275 awarded by the National Institutes of Health (NIH). The government has certain rights to the invention.

FIELD OF THE INVENTION

This disclosure generally relates to a series of melampomagnolide B (MMB) dimers, including carbamate, carbonate, succinic amide, ester and carboxamide dimers of MMB. These compounds exhibit anti-cancer activity.

BACKGROUND OF THE INVENTION

Parthenolide (PTL), an abundant sesquiterpene lactone found in the medicinal herb feverfew (*Tanacetum parthenium*), has undergone intense pharmacological research, especially for its antileukemic properties. Initial biomechanistic studies of PTL and its derivatives indicate that the compound promotes apoptosis by inhibiting the NF-kB transcription factor complex, thereby downregulating anti-apoptotic genes under NF-kB control. PTL and its derivatives may also interfere with glutathione function, specifically glutathione's ability to sequester reactive oxygen species. In culture, PTL induces robust apoptosis of primary acute myeloid leukemia (AML) cells in culture. To overcome poor water-solubility, PTL may be derivatized with an alkylamino, which can convert into water-soluble salts. A series of fluorinated amino derivatives of PTL exhibit activity in antiproliferative assays in HL-60 (human promyelocytic leukemia) cells. PTL has also been the source of several antileukemic compounds arising from chemical modification of the PTL molecule.

Melampomagnolide B (MMB), a melampolide originally isolated from *Magnolia grandiflora*, is an antileukemic sesquiterpene with properties similar to those of PTL. MMB has been synthesized via selenium oxide oxidation of the C10 methyl group of PTL, resulting in a concomitant conversion of the geometry of the C9-C10 double bond from trans to the cis geometry. MMB contains a primary OH group, providing a point of attachment for derivatives with increased water solubility, bioavailability, and tissue targeting. Phase 1 clinical data from dimethylamino-parthenolide (DMAPT), a synthetic aminoparthenolide derivative, indicated improved bioavailability and longer in vivo half-lifes for PTL and MMB derivatives with increased water solubility. However, there remains a need for MMB-like compounds with increased cytotoxicity across a broad range of cancers.

DETAILED DESCRIPTION OF THE INVENTION

DETAILED DESCRIPTION OF THE INVENTION

Figure 1:
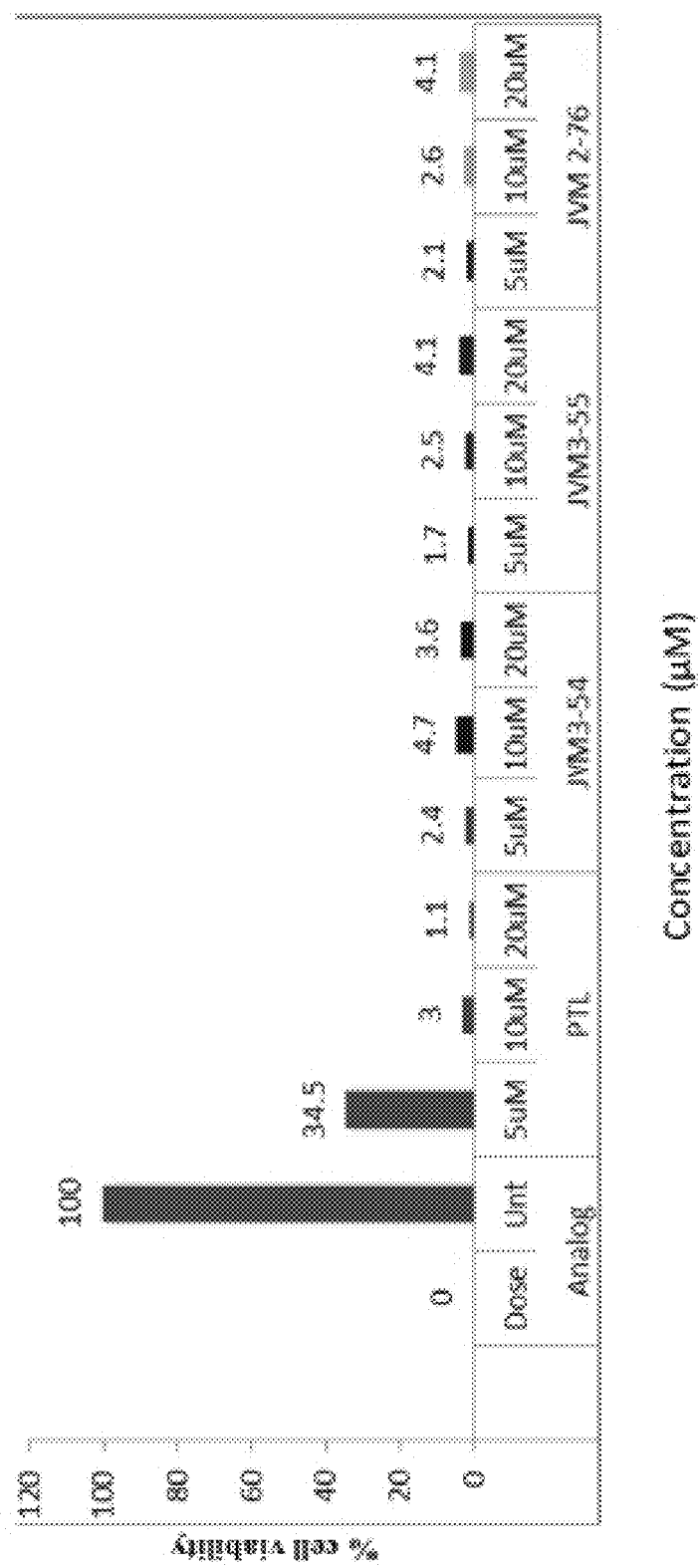
FIG. 1 depicts a graph showing activity of MMB carbamate dimers against M9 cell lines.

Provided herein are carbamate, carbonate, succinic amide, ester and carboxamide dimers of MMB. Carbamate and carbonate dimers may be synthesized via an intermediate prepared by reacting MMB (2) with carbonylditriazole (4) to afford MMB triazole (5). This triazole intermediate may be reacted with various terminal alkyl diamines to afford the corresponding carbamate dimer. To prepare carbonate dimers of MMB, MMB triazole may be reacted with terminal alkyl dihydroxyl compounds. Succinic amide dimers may be synthesized by reacting MMB succinate (7) with various terminal alkyl diamines to afford the corresponding succinic amide dimer. Further, ester dimers of MMB may be prepared by reacting MMB (2) with various terminal alkyl carbonyl chlorides (9). Additionally, carboxamide dimers of MMB may be prepared by reacting a carboxylic acid derivative of PTL with terminal alkyl diamines to afford the corresponding carboxamide dimers.

These newly synthesized compounds were screened for their antileukemic activity against the M9-ENL cell line. Based on cell viability results, the majority of the compounds showed excellent potency and were more potent than parent monomeric compounds, MMB and parthenolide. Moreover, some of these compounds showed activity in the nanomolar range against several human cancer cell lines.

In general, the compounds detailed herein include compounds comprising a melampomagnolide B (MMB) structure as diagrammed below. For the purposes of illustration, the ring atoms of MMB are numbered as shown below:

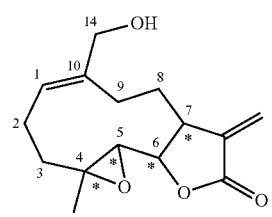 [SMILES: C=C1C(=O)OC2C1CC/C(CO)=C\CCC1(C)OC21]

MMB compounds have asymmetric centers. In particular, the MMB compounds may have at least four chiral carbons (designated by asterisks in the diagram above); namely, C4, C5, C6, and C7.

I. Compounds Comprising Formula (I), (II), (III), (IV) and (V)

Provided herein are compounds comprising Formula (I):

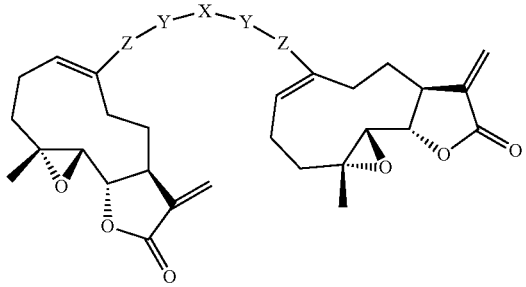

(I)

wherein:
Z is independently selected from the group consisting of CH$_2$, O, C(O), and CH, wherein when Z is CH, Z is connected to Y via a double bond and Y is N;
Y is independently selected from the group consisting of O, NR, N,

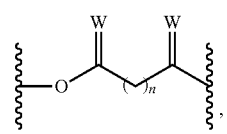

heterocycle, hydrocarbyl and substituted hydrocarbyl;
X is selected from the group consisting of (CH$_2$)$_n$, C(O),

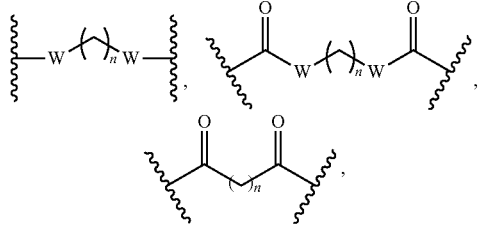

—(CH$_2$)$_n$—W—C(O)—, —C(O)—W—C(O)—, —C(O)NH—W—NHC(O)—, —C(O)O—W—OC(O)—, carbocycle, heterocycle, alkyl, substituted alkyl, hydrocarbyl and substituted hydrocarbyl;
R is selected from the group consisting of H, alkyl, hydrocarbyl and substituted hydrocarbyl;
W is selected from the group consisting of O, S, NH, N-alkyl, heterocycle, alkyl, substituted alkyl, hydrocarbyl and substituted hydrocarbyl; and
n is an integer from 0-10.

In one embodiment, a compound of the disclosure comprises Formula (I), wherein:

Z is selected from the group consisting of CH$_2$ or O;
Y is selected from the group consisting of O, NR, and

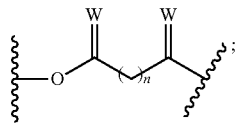

X is selected from the group consisting of (CH$_2$)$_n$, CO,

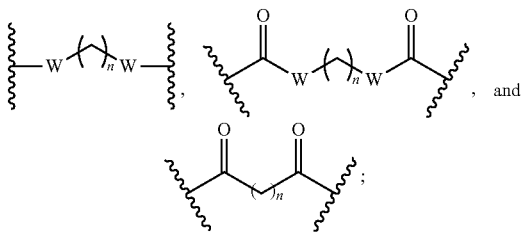

R is selected from the group consisting of H, and alkyl;
W is selected from the group consisting of O, S, NH, and N-alkyl; and
n is an integer from 0-10.

In another embodiment, a compound of the disclosure comprises Formula (I), wherein:
Z is independently selected from the group consisting of CH$_2$, C(O) and CH, wherein when Z is CH, Z is connected to Y via a double bond and Y is N;
Y is independently selected from the group consisting of O, heterocycle, NR, N, and

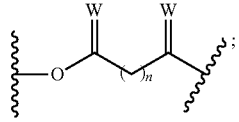

X is selected from the group consisting of C(O), —(CH$_2$)$_n$—W—C(O)—, —C(O)—W—C(O)—, substituted alkyl, (CH$_2$)$_n$, carbocycle, —C(O)NH—W—NHC(O)—, —C(O)O—W—OC(O)—,

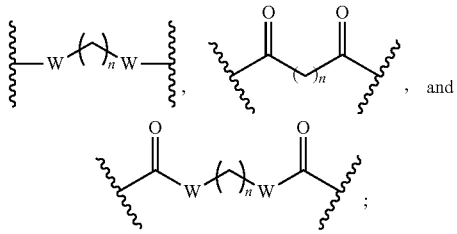

R is H;
W is selected from the group consisting of O, heterocycle, alkyl, substituted alkyl, and NH; and
n is an integer from 0-10.

In still another embodiment, a compound of the disclosure comprises Formula (I), wherein:
Z is CH, Z is connected to Y via a double bond and Y is N;
X is selected from the group consisting of C(O), —(CH$_2$)$_n$—W—C(O)—, —C(O)—W—C(O)—, substituted alkyl, (CH$_2$)$_n$, carbocycle, —C(O)NH—W—NHC(O)—, —C(O)O—W—OC(O)—,

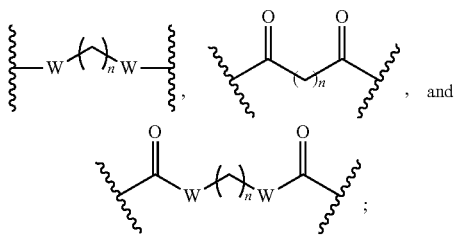

W is selected from the group consisting of O, heterocycle, alkyl, substituted alkyl, and NH; and
n is an integer from 0-10.

In still yet another embodiment, a compound of the disclosure comprises Formula (I), wherein:
Z is CH, Z is connected to Y via a double bond and Y is N;
X is selected from the group consisting of substituted alkyl and $(CH_2)_n$; and
n is an integer from 0-10.

In one embodiment, a compound of the disclosure comprises Formula (I), wherein:
Z is CH, Z is connected to Y via a double bond and Y is N;
X is $(CH_2)_n$; and
n is an integer from 0-10.

In yet another embodiment, a compound of the disclosure comprises Formula (I), wherein:
Z is independently selected from the group consisting of $CH_2$ and CH, wherein when Z is CH, Z is connected to Y via a double bond and Y is N;
Y is independently selected from the group consisting of heterocycle and N;
X is selected from the group consisting of C(O), —$(CH_2)_n$—W—C(O)—, —C(O)—W—C(O)—, substituted alkyl, $(CH_2)_n$, carbocycle, —C(O)NH—W—NHC(O)—, —C(O)O—W—OC(O)—,

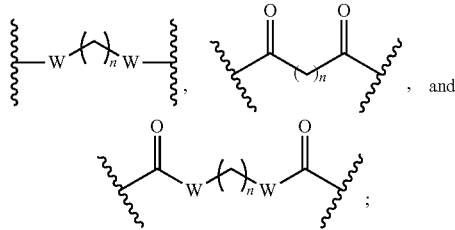

W is selected from the group consisting of O, heterocycle, alkyl, substituted alkyl, and NH; and
n is an integer from 0-10.

In a different embodiment, a compound of the disclosure comprises Formula (I), wherein:
Z is independently selected from the group consisting of $CH_2$ and CH, wherein when Z is CH, Z is connected to Y via a double bond and Y is N;
Y is independently selected from the group consisting of heterocycle and N;
X is selected from the group consisting of substituted alkyl and $(CH_2)_n$; and
n is an integer from 0-10.

In other embodiments, a compound of the disclosure comprises Formula (I), wherein:
Z is independently selected from the group consisting of $CH_2$ and CH, wherein when Z is CH, Z is connected to Y via a double bond and Y is N;
Y is independently selected from the group consisting of heterocycle and N;
X is $(CH_2)_n$; and
n is an integer from 0-10.

In another embodiment, a compound of the disclosure comprises Formula (I), wherein:
Z is C(O);
Y is independently selected from the group consisting of O, heterocycle, NR, N, and

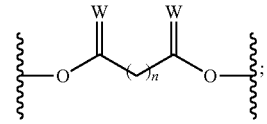

X is selected from the group consisting of C(O), —$(CH_2)_n$—W—C(O)—, —C(O)—W—C(O)—, substituted alkyl, $(CH_2)_n$, carbocycle, —C(O)NH—W—NHC(O)—, —C(O)O—W—OC(O)—,

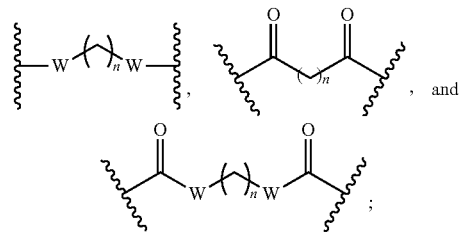

R is H;
W is selected from the group consisting of O, heterocycle, alkyl, substituted alkyl, and NH; and
n is an integer from 0-10.

In still another embodiment, a compound of the disclosure comprises Formula (I), wherein:
Z is C(O);
Y is NR;
X is selected from the group consisting of C(O), —$(CH_2)_n$—W—C(O)—, —C(O)—W—C(O)—, substituted alkyl, $(CH_2)_n$, carbocycle, —C(O)NH—W—NHC(O)—, —C(O)O—W—OC(O)—,

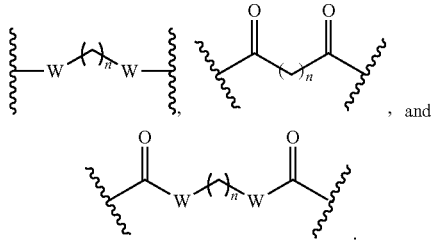

R is H;
W is selected from the group consisting of O, heterocycle, alkyl, substituted alkyl, and NH; and
n is an integer from 0-10.

In still yet another embodiment, a compound of the disclosure comprises Formula (I), wherein:

Z is C(O);
Y is NR;
X is selected from the group consisting of substituted alkyl and $(CH_2)_n$;
R is H; and
n is an integer from 0-10.

In yet another embodiment, a compound of the disclosure comprises Formula (I), wherein:
Z is $CH_2$;
Y is independently selected from the group consisting of O, heterocycle, NR, N, and

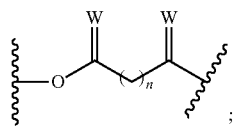
;

X is selected from the group consisting of C(O), $-(CH_2)_n-W-C(O)-$, $-C(O)-W-C(O)-$, substituted alkyl, $(CH_2)_n$, carbocycle, $-C(O)NH-W-NHC(O)-$, $-C(O)O-W-OC(O)-$,

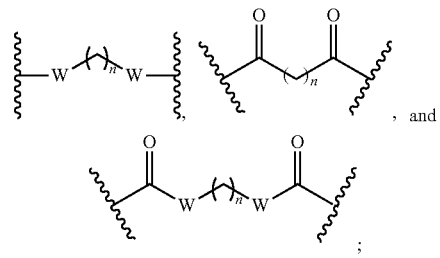
, and

;

R is H;
W is selected from the group consisting of O, heterocycle, alkyl, substituted alkyl, and NH; and
n is an integer from 0-10.

In a different embodiment, a compound of the disclosure comprises Formula (I), wherein:
Z is $CH_2$;
Y is heterocycle;
X is selected from the group consisting of C(O), $-(CH_2)_n-W-C(O)-$, $-C(O)-W-C(O)-$, substituted alkyl, $(CH_2)_n$, carbocycle, $-C(O)NH-W-NHC(O)-$, $-C(O)O-W-OC(O)-$,

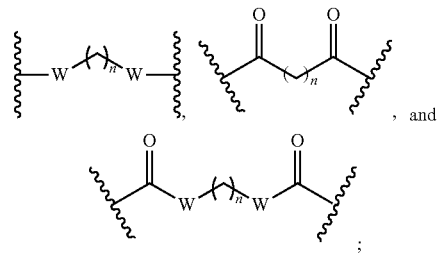
, and

;

W is selected from the group consisting of O, heterocycle, alkyl, substituted alkyl, and NH; and
n is an integer from 0-10.

In certain embodiments, a compound of the disclosure comprises Formula (I), wherein:
Z is $CH_2$;
Y is heterocycle;
X is selected from the group consisting of substituted alkyl, $(CH_2)_n$, carbocycle; and
n is an integer from 0-10.

In other embodiments, a compound of the disclosure comprises Formula (I), wherein:
Z is $CH_2$;
Y is independently selected from the group consisting of O and heterocycle;
X is selected from the group consisting of C(O), $-(CH_2)_n-W-C(O)-$, $-C(O)-W-C(O)-$, substituted alkyl, $(CH_2)_n$, carbocycle, $-C(O)NH-W-NHC(O)-$, $-C(O)O-W-OC(O)-$,

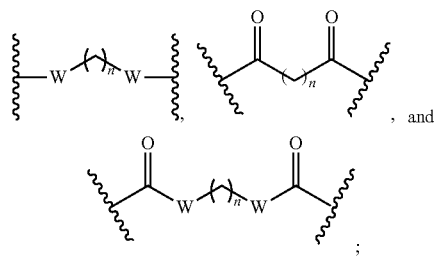
, and

;

R is H;
W is selected from the group consisting of O, heterocycle, alkyl, substituted alkyl, and NH; and
n is an integer from 0-10.

In another embodiment, a compound of the disclosure comprises Formula (I), wherein:
Z is $CH_2$;
Y is independently selected from the group consisting of O and heterocycle;
X is $-(CH_2)_n-W-C(O)$;
W is selected from the group consisting of O, heterocycle, alkyl, substituted alkyl, and NH; and
n is an integer from 0-10.

In still another embodiment, a compound of the disclosure comprises Formula (I), wherein:
Z is $CH_2$;
Y is independently selected from the group consisting of O and heterocycle;
X is $-(CH_2)_n-W-C(O)$;
W is selected from the group consisting of O and NH; and
n is an integer from 0-10.

In still yet another embodiment, a compound of the disclosure comprises Formula (I), wherein:
Z is $CH_2$;
Y is NR;
X is selected from the group consisting of C(O), $-(CH_2)_n-W-C(O)-$, $-C(O)-W-C(O)-$, substituted alkyl, $(CH_2)_n$, carbocycle, $-C(O)NH-W-NHC(O)-$, $-C(O)O-W-OC(O)-$,

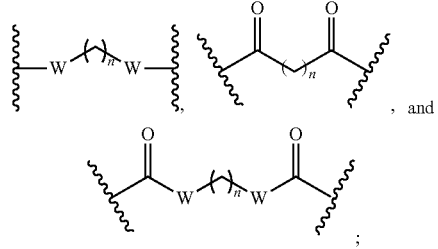
, and

;

R is H;
W is selected from the group consisting of O, heterocycle, alkyl, substituted alkyl, and NH; and
n is an integer from 0-10.

In yet another embodiment, a compound of the disclosure comprises Formula (I), wherein:
Z is CH$_2$;
Y is NR;
X is selected from the group consisting of C(O), —C(O)—W—C(O)—, —C(O)NH—W—NHC(O)—, —C(O)O—W—OC(O)—,

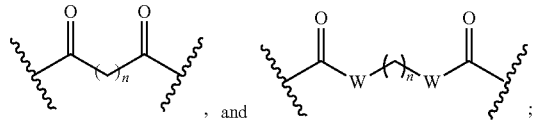
, and ;

R is H;
W is selected from the group consisting of O, heterocycle, alkyl, substituted alkyl, and NH; and
n is an integer from 0-10.

In a different embodiment, a compound of the disclosure comprises Formula (I), wherein:
Z is CH$_2$;
Y is NR;
X is selected from the group consisting of C(O), —C(O)—W—C(O)—, —C(O)NH—W—NHC(O)—, —C(O)O—W—OC(O)—,

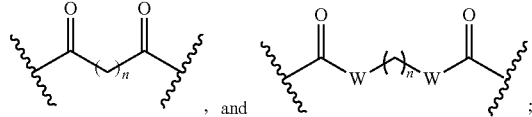
, and ;

R is H;
W is selected from the group consisting of heterocycle, alkyl, substituted alkyl, and NH; and
n is an integer from 0-10.

In other embodiments, a compound of the disclosure comprises Formula (I), wherein:
Z is CH$_2$;
Y is O;
X is selected from the group consisting of C(O), —(CH$_2$)$_n$—W—C(O)—, —C(O)—W—C(O)—, substituted alkyl, (CH$_2$)$_n$, carbocycle, —C(O)NH—W—NHC(O)—, —C(O)O—W—OC(O)—,

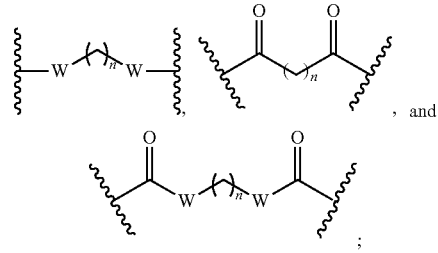
;

R is H;
W is selected from the group consisting of O, heterocycle, alkyl, substituted alkyl, and NH; and
n is an integer from 0-10.

In certain embodiments, a compound of the disclosure comprises Formula (I), wherein:
Z is CH$_2$;
Y is O;
X is selected from the group consisting of C(O), —C(O)—W—C(O)—, substituted alkyl, —C(O)NH—W—NHC(O)—, —C(O)O—W—OC(O)—,

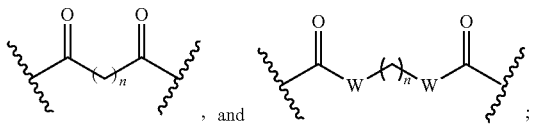
, and ;

W is selected from the group consisting of O, heterocycle, alkyl, substituted alkyl, and NH; and
n is an integer from 0-10.

In another embodiment, a compound of the disclosure comprises Formula (I), wherein:
Z is CH$_2$;
Y is

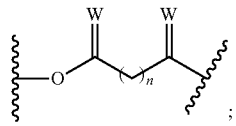
;

X is selected from the group consisting of C(O), —(CH$_2$)$_n$—W—C(O)—, —C(O)—W—C(O)—, substituted alkyl, (CH$_2$)$_n$, carbocycle, —C(O)NH—W—NHC(O)—, —C(O)O—W—OC(O)—,

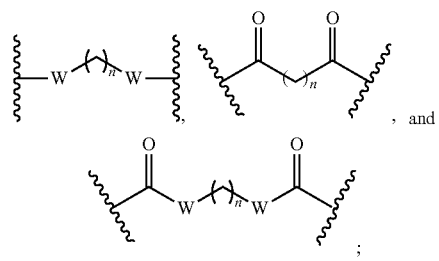
, and ;

W is selected from the group consisting of O, heterocycle, alkyl, substituted alkyl, and NH; and
n is an integer from 0-10.

In still another embodiment, a compound of the disclosure comprises Formula (I), wherein:
Z is CH$_2$;
Y is

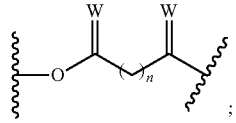
;

X is selected from the group consisting of substituted alkyl, (CH$_2$)$_n$, and

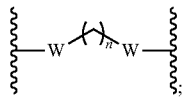
;

W is selected from the group consisting of O, heterocycle, alkyl, substituted alkyl, and NH; and
n is an integer from 0-10.

In still yet another embodiment, a compound of the disclosure comprises Formula (I), wherein:
Z is $CH_2$;
Y is

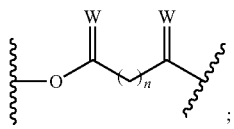

X is selected from the group consisting of substituted alkyl, $(CH_2)_n$, and

W is selected from the group consisting of O and NH; and
n is an integer from 0-10.

Also provided herein are compounds comprising Formula (II):

(II)

wherein:
X is selected from the group consisting of O or NH; and
n is an integer from 0-10.

Also provided herein are compounds comprising Formula (III):

wherein:
n is an integer from 1-10.

Also provided herein are compounds comprising Formula (IV):

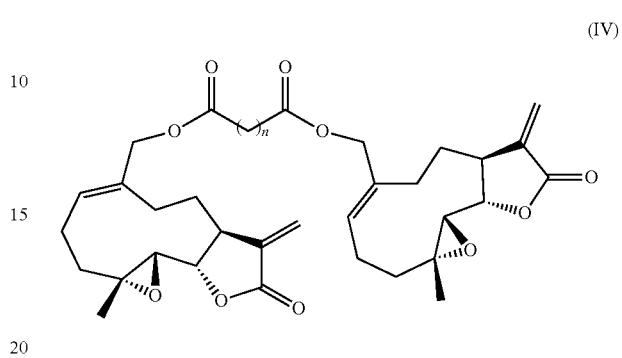

wherein:
n is an integer from 1-10.

Also provided herein are compounds comprising Formula (V):

(V)

wherein:
n is an integer from 1-10.

In all of the foregoing embodiments, the core MMB compound of Formula (I), (II), (III), (IV) and (V) may be modified. Specifically, the core MMB compound of Formula (I), (II), (III), (IV) and (V) may be modified at position $R_1$ as shown below:

(III)

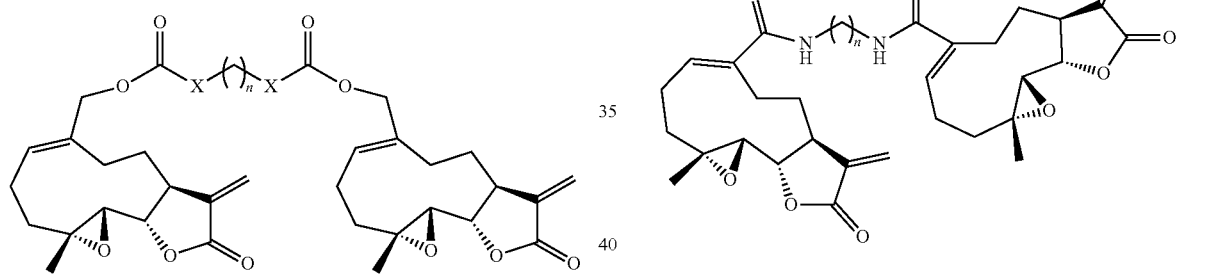

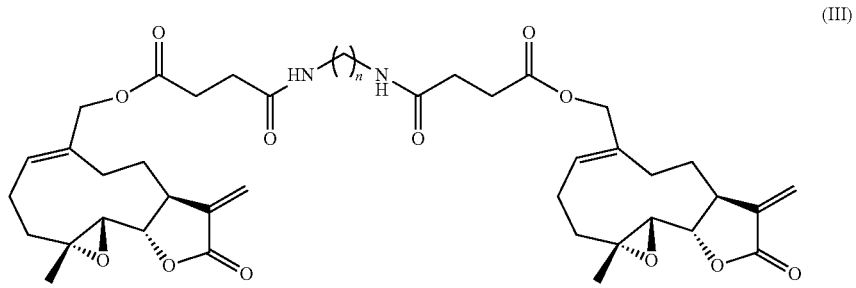

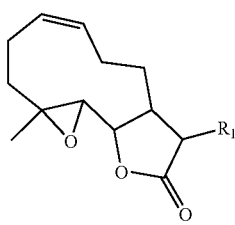

In certain embodiments, $R_1$ is another MMB compound connected at $R_1$ via a linker. The linker may be X as described above. In other embodiments, $R_1$ is a linker connecting the two MMB compounds of the dimer to one another. The linker may be X as described above. In still other embodiment, $R_1$ comprises an amine which may or may not be contacted with a carboxylic acid compound. The amine may be a tertiary amine. The amine may be connected at $R_1$ via an alkyl chain. Exemplary compounds comprising an $R_1$ modification are depicted in Table 5, lines 33-38.

Non-limiting examples of compounds comprising Formula (I), (II), (III), (IV) and (V) are presented in Table 5.

(a) Downstream Applications

In some embodiments, the compound comprising Formulas (I), (II), (III), (IV) and (V) may be converted into a pharmaceutically acceptable salt. "Pharmaceutically acceptable salts" are salts commonly used to form alkali metal salts and to form addition salts of free acids or free bases. The nature of the salt may vary, provided that it is pharmaceutically acceptable.

Suitable pharmaceutically acceptable acid addition salts of compounds comprising Formulas (I), (II), (III), (IV) and (V) may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically acceptable base addition salts include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine-(N-methylglucamine) and procaine. All of these salts may be prepared by conventional means from the corresponding compound by reacting, for example, the appropriate acid or base with the any compound comprising Formulas (I), (II), (III), (IV) and (V).

(b) Stereochemistry

The compounds comprising Formulas (I), (II), (III), (IV) and (V) may independently have an optical activity of (−) or (+). In particular, the configuration of C4, C5, C6, and C7, respectively, may be RRRR, RRSR, RRRS, RRSS, RSRR, RSSR, RSRS, RSSS, SRRR, SRSR, SRRS, SRSS, SSRR, SSSR, SSRS, or SSSS.

II. Processes for Preparing Compounds Comprising Formulas (I), (II), (III), (IV) and (V)

In particular, provided herein are processes for preparing a compound comprising Formula (I). In general, the process comprises contacting MMB (2) or its carboxylic acid (3) with an appropriate reagent to form a compound comprising Formula (I).

In an aspect, provided herein are processes for preparing a carbamate or carbonate compound comprising Formulas (I) or (II). The process comprises (a) contacting MMB (2) with a triazole reagent to form a triazole intermediate (e.g. (5)). The process continues with (b) contacting the triazole intermediate with a terminal alkyl diamine or a terminal alkyl dihydroxyl to form a carbamate or carbonate compound comprising Formulas (I) or (II).

In another aspect, provided herein are processes for preparing an amide compound comprising Formulas (I) or (III). The process comprises (a) contacting MMB (2) with an acid anhydride to form a carboxylic acid derivative (e.g. (7)). The process continues with (b) contacting the carboxylic acid derivative with a terminal alkyl diamine to form a succinic amide compound comprising Formulas (I) or (III).

In still another aspect, provided herein are processes for preparing an ester compound comprising Formulas (I) or (IV). The process comprises contacting MMB (2) with a terminal alkyl carbonyl chloride (9) to form an ester compound comprising Formulas (I) or (IV).

In still yet another aspect, provided herein are processes for preparing a carboxamide compound comprising Formulas (I) or (V). The process comprises (a) oxidizing parthenolide to form a carboxylic acid derivative of melampomagnolic acid (3). The process continues with (b) contacting the carboxylic acid derivative with a terminal alkyl diamine to form a carboxamide compound comprising Formulas (I) or (V).

(a) Carbamate and Carbonate Dimers of MMB

Carbamate and carbonate dimers may be synthesized via a triazole intermediate of MMB (5). The triazole intermediate of MMB (5) may be prepared by reacting MMB with carbonyldiatriazole (CDT) dissolved in dichloromethane. The triazole intermediate (5) may then be reacted with various terminal alkyl diamines and dihydroxyls to form a variety of carbamate (6; X=NH) and carbonate dimers (6; X=O) (Scheme 1). Exemplary compounds are depicted in Table 5, lines 1-11.

Scheme 1: Synthesis of carbamate and carbonate dimers of MMB

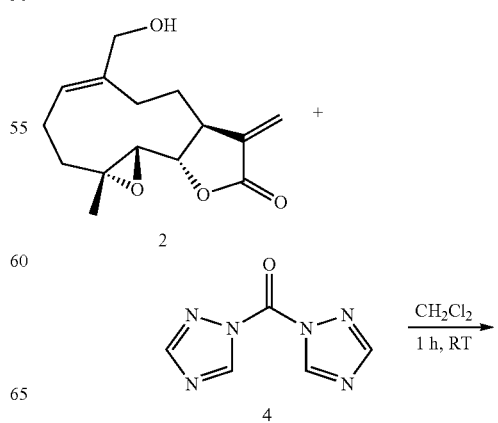

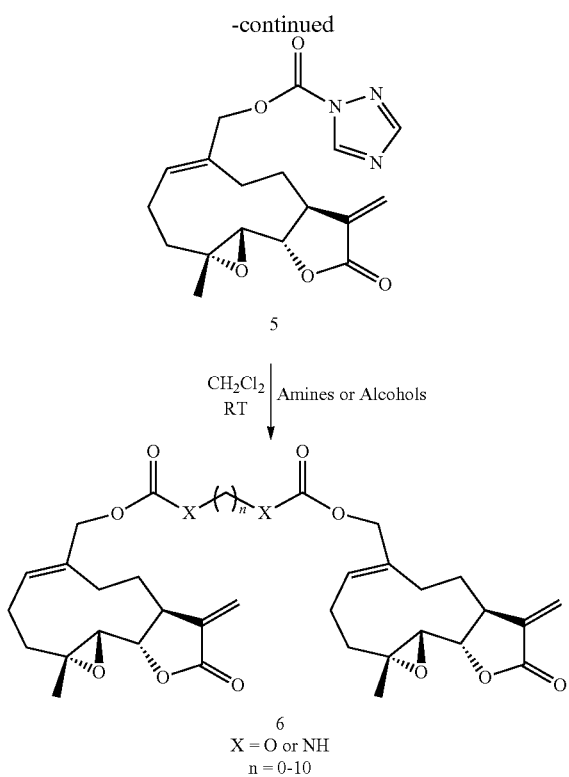

6
X = O or NH
n = 0-10

In particular, provided herein are processes for preparing a carbamate or carbonate compound comprising Formulas (I) or (II). The process comprises (a) contacting MMB (2) with a triazole reagent to form a triazole intermediate (e.g. (5)). The process continues with (b) contacting the triazole intermediate with a terminal alkyl diamine or a terminal alkyl dihydroxyl to form a carbamate or carbonate compound comprising Formulas (I) or (II).

(i) Step (a)—Reaction Mixture

Step (a) of the process comprises contacting MMB (2) with a triazole reagent to form a triazole intermediate (e.g. (5)). The process commences with the formation of a reaction mixture comprising MMB (2), which is detailed above, the triazole reagent, and optionally a solvent system.

The triazole reagent may be any compound which reacts with a hydroxyl group to provide a triazolyl carbamate. Non-limiting examples of suitable triazole reagents include carbonylditriazole (such as 1,1'-carbonyl-di-(1,2,4-triazole) and thiocarbonylditriazole. Another possible synthetic approach to the synthesis of the imidazole carbamate analog of MMB is by utilizing carbonyldiimidazole as a reagent instead of carbonylditriazole.

The amounts of triazole reagent that are contacted with MMB (2) may vary. In general, the mole to mole ratio of MMB (2) to triazole agent may range from about 1:0.2 to about 1:15. In certain embodiments, the mole to mole ratio of MMB (2) to the triazole reagent may range from about 1:0.2 to about 1:0.7, from about 1:0.7 to about 1:1.5, from about 1:1.5 to about 1:2.5, from about 1:2.5 to about 1:5, from about 1:5 to about 1:10, or from about 1:10 to about 1:15. In certain embodiments, the mole to mole ratio of MMB (2) to the triazole reagent may range from about 1:0.7 to about 1:3.

The reaction is generally conducted in the presence of a solvent or solvent system. The solvent may be a polar aprotic solvent, a polar protic solvent, or a nonpolar solvent. Non-limiting examples of suitable polar aprotic solvents include acetone, acetonitrile, diethoxymethane, N,N-dimethylformamide (DMF), dimethyl sulfoxide (DMSO), N,N-dimethylpropanamide (or dimethylpropionamide; DMP), 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMA), N-methyl-2-pyrrolidinone (NMP), 1,4-dioxane, ethyl formate, formamide, hexachloroacetone, hexamethylphosphoramide, methyl acetate, N-methylacetamide, N-methylformamide, methylene chloride (dichloromethane, DCM), chloroform, methoxyethane, morpholine, nitrobenzene, nitromethane, propionitrile, pyridine, sulfolane, tetramethylurea, tetrahydrofuran (THF), 2-methyl tetrahydrofuran, tetrahydropyran, trichloromethane, and combinations thereof. Non-limiting examples of suitable polar protic solvents include water; alcohols such as methanol, ethanol, isopropanol, n-propanol, isobutanol, n-butanol, s-butanol, t-butanol, and the like; diols such as propylene glycol; organic acids such as formic acid, acetic acid, and so forth; amides such as formamide, acetamide, and the like; and combinations of any of the above. Representative nonpolar solvents include, but are not limited to, alkane and substituted alkane solvents (including cycloalkanes), aromatic hydrocarbons, esters, ethers, ketones, and combinations thereof. Specific polar aprotic solvents that may be employed include, for example, dichloromethane, chloroform, and combinations thereof.

In general, the volume to mass ratio of the solvent to MMB (2) ranges from about 1:1 to about 100:1. In various embodiments, the volume to mass ratio of the solvent to MMB (2) may range from about 1:1 to about 5:1, from about 5:1 to about 10:1, from about 10:1 to about 20:1, from about 20:1 to about 30:1, from about 30:1 to about 40:1, from about 40:1 to about 50:1, from about 50:1 to about 60:1, from about 60:1 to about 70:1, from about 70:1 to about 80:1, from about 80:1 to about 90:1, or from about 90:1 to about 100:1. In exemplary embodiments, the volume to mass ratio of the solvent to MMB (2) may range from about 20:1 to about 30:1.

(ii) Step (a)—Reaction Conditions

In general, the reaction is conducted at a temperature that ranges from about 0° C. to about 50° C. In various embodiments, the reaction may be conducted at a temperature from about 0° C. to about 10° C., from about 10° C. to about 20° C., from about 20° C. to about 30° C., from about 30° C. to about 40° C., or from about 40° C. to about 50° C. In certain embodiments, the reaction may be conducted at a temperature of about 25° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., TLC, HPLC) or another suitable method. In this context, a "completed reaction" generally means that the reaction mixture contains a significantly diminished amount of MMB (2), and a significantly increased amount of the triazole intermediate (e.g. (5)) compared to the amounts of each present at the beginning of the reaction. Typically, the amount of MMB (2) remaining in the reaction mixture after the reaction is complete may be less than about 3%, or less than about 1%. In general, the reaction may proceed for about 5 minutes to about 48 hours. Typically, the duration of the reaction is longer at lower reaction temperatures. In certain embodiments, the reaction may be allowed to proceed for about a period of time ranging from about 5 minutes to about 10 minutes, from about 10 minutes to about 15 minutes, from about 15 minutes to about 30 minutes, from about 30 minutes to about 1 hour, about 1 hour to about 3 hours, from about 3 hours to about 6 hours, from about 6 hours to about 12 hours, from about 12 hours to about 18 hours, from about 18 hours to about 24 hours, from about 24 hours to about 36 hours, or from about 36 hours to about 48 hours. In certain embodiments, the reaction may be allowed to proceed about 5 minutes to about 15 minutes. In other embodiments, the reaction may be allowed to proceed about 45 minutes to about 75 minutes.

Generally, the triazole intermediate is not isolated and step (b) of the process proceeds in the same reaction pot or reactor. In some embodiments, the triazole intermediate may be isolated from the reaction mixture using techniques known to those of skill in the art. Non-limiting examples of suitable techniques include precipitation, extraction, evaporation, distillation, chromatography, and crystallization.

The yield of the triazole intermediate can and will vary. Typically, the yield of the triazole intermediate may be at least about 40%. In one embodiment, the yield of the triazole intermediate may range from about 40% to about 60%. In another embodiment, the yield of the triazole intermediate may range from about 60% to about 80%. In a further embodiment, the yield of the triazole intermediate may range from about 80% to about 90%. In still another embodiment, the yield of the triazole intermediate may be greater than about 90%, or greater than about 95%.

(iii) Step (b)—Reaction Mixture

Step (b) of the process continues with contacting the triazole intermediate with a terminal alkyl diamine or a terminal alkyl dihydroxyl to form a compound comprising Formulas (I) or (II). The process commences with the formation of a reaction mixture comprising the triazole intermediate, which is detailed above, a terminal alkyl diamine or a terminal alkyl dihydroxyl, and optionally a solvent system.

As used herein, a "terminal alkyl diamine" is a polyamine that comprises two amino groups on either end of an alkyl chain. The alkyl chain may be linear, branched or contain an aromatic ring. As used herein, a "terminal alkyl dihydroxyl" is an alcohol that comprises two functional hydroxyl groups on either end of an alkyl chain. The alkyl chain may be a hydrocarbyl alkyl chain or a substituted hydrocarbyl alkyl chain. The alkyl chain may be a length of 1 to 10 atoms. For example, the alkyl chain may be 1, 2, 3, 4, 5, 6, 7, 8, 9 or 10 atoms in length. In an embodiment where the alkyl chain is branched or contains an aromatic ring, the length refers to the consecutive atoms connecting the two amino groups or the two hydroxyl groups.

The amounts of the terminal alkyl diamine or a terminal alkyl dihydroxyl that are contacted with the triazole intermediate may vary. In general, the mole to mole ratio of the triazole intermediate to the terminal alkyl diamine or a terminal alkyl dihydroxyl may range from about 1:0.2 to about 1:15. In certain embodiments, the mole to mole ratio of the triazole intermediate to the terminal alkyl diamine or a terminal alkyl dihydroxyl may range from about 1:0.2 to about 1:0.7, from about 1:0.7 to about 1:1.5, from about 1:1.5 to about 1:2.5, from about 1:2.5 to about 1:5, from about 1:5 to about 1:10, or from about 1:10 to about 1:15. In certain embodiments, the mole to mole ratio of the triazole intermediate to the terminal alkyl diamine or a terminal alkyl dihydroxyl may range from about 1:0.7 to about 1:3.

Contact with the triazole intermediate generally is conducted in the presence of a solvent or solvent system. Suitable solvents are detailed above in Section II(a)(i). In exemplary embodiments, the solvent may be dichloromethane, chloroform, or combinations thereof. In general, the volume to mass ratio of the solvent to the triazole intermediate ranges from about 1:1 to about 100:1. In various embodiments, the volume to mass ratio of the solvent to the triazole intermediate may range from about 1:1 to about 5:1, from about 5:1 to about 10:1, from about 10:1 to about 20:1, from about 20:1 to about 30:1, from about 30:1 to about 40:1, from about 40:1 to about 50:1, from about 50:1 to about 60:1, from about 60:1 to about 70:1, from about 70:1 to about 80:1, from about 80:1 to about 90:1, or from about 90:1 to about 100:1. In exemplary embodiments, the volume to mass ratio of the solvent to the triazole intermediate may range from about 20:1 to about 30:1.

(iv) Step (b)—Reaction Conditions

In general, the reaction is conducted at a temperature that ranges from about 0° C. to about 50° C. In various embodiments, the reaction may be conducted at a temperature from about 0° C. to about 10° C., from about 10° C. to about 20° C., from about 20° C. to about 30° C., from about 30° C. to about 40° C., or from about 40° C. to about 50° C. In certain embodiments, the reaction may be conducted at a temperature of about 25° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., TLC, HPLC) or another suitable method. Typically, the amount of the triazole intermediate remaining in the reaction mixture after the reaction is complete may be less than about 3%, or less than about 1%. In general, the reaction may proceed for about 5 minutes to about 48 hours. Typically, the duration of the reaction is longer at lower reaction temperatures. In certain embodiments, the reaction may be allowed to proceed for about a period of time ranging from about 5 minutes to about 10 minutes, from about 10 minutes to about 15 minutes, from about 15 minutes to about 30 minutes, from about 30 minutes to about 1 hour, about 1 hour to about 3 hours, from about 3 hours to about 6 hours, from about 6 hours to about 12 hours, from about 12 hours to about 18 hours, from about 18 hours to about 24 hours, from about 24 hours to about 36 hours, or from about 36 hours to about 48 hours. In certain embodiments, the reaction may be allowed to proceed about 20 minutes to about 40 minutes. In other embodiments, the reaction may be allowed to proceed about 8 hours to about 12 hours. In still other embodiments, the reaction may be allowed to proceed about 2 hours to about 6 hours. In still yet other embodiments, the reaction may be allowed to proceed about 2 hours to about 16 hours.

The yield of the compound comprising Formulas (I) or (II) can and will vary. Typically, the yield of the compound comprising Formulas (I) or (II) may be at least about 40%. In one embodiment, the yield of the compound comprising Formulas (I) or (II) may range from about 40% to about 60%. In another embodiment, the yield of the compound comprising Formulas (I) or (II) may range from about 60% to about 80%. In a further embodiment, the yield of the compound comprising Formulas (I) or (II) may range from about 80% to about 90%. In still another embodiment, the yield of the compound comprising Formulas (I) or (II) may be greater than about 90%, or greater than about 95%.

(b) Amide Dimers of MMB

In other embodiments, MMB may be reacted with succinic anhydride in the presence of triethylamine to afford a carboxylic acid derivative of MMB (7). The MMB carboxylic acid derivative may be reacted with various terminal alkyl diamines to afford the corresponding amide dimers of MMB (8) (Scheme 2). Exemplary compounds are depicted in Table 5, lines 12-19.

Scheme 2: Synthesis of succinic amide dimers of MMB

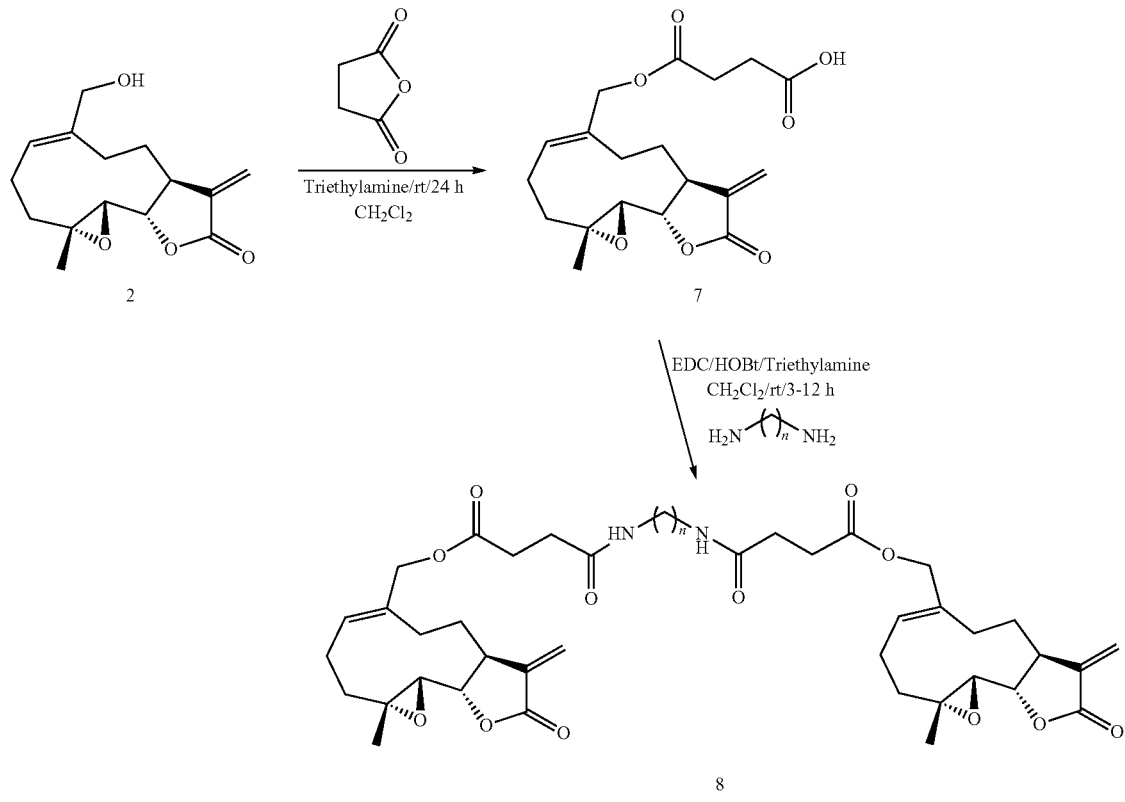

n = 1-10

In particular, provided herein are processes for preparing an amide compound comprising Formulas (I) or (III). The process comprises (a) contacting MMB (2) with an acid anhydride to form a carboxylic acid derivative (e.g. (7)). The process continues with (b) contacting the carboxylic acid derivative with a terminal alkyl diamine to form a succinic amide compound comprising Formulas (I) or (III).

(i) Step (a)—Reaction Mixture

Step (a) of the process comprises contacting MMB (2) with an acid anhydride to form a carboxylic acid derivative (e.g. (7)). The process commences with the formation of a reaction mixture comprising MMB (2), which is detailed above, the acid anhydride, and optionally a solvent system.

The acid anhydride may be any compound which reacts with a hydroxyl group to provide a carboxylic acid derivative. A suitable acid anhydride is a compound that has two acyl groups bonded to the same oxygen atom. In a preferred embodiment, the acid anhydride is a cyclic anhydride. Non-limiting examples of suitable acid anhydrides include succinic anhydride, maleic anhydride, itaconic anhydride, citraconic anhydride and 2-pentendioic anhydride. In an exemplary embodiment, the acid anhydride is succinic anhydride.

The amounts of acid anhydride that are contacted with MMB (2) may vary. In general, the mole to mole ratio of MMB (2) to acid anhydride may range from about 1:0.2 to about 1:15. In certain embodiments, the mole to mole ratio of MMB (2) to acid anhydride may range from about 1:0.2 to about 1:0.7, from about 1:0.7 to about 1:1.5, from about 1:1.5 to about 1:2.5, from about 1:2.5 to about 1:5, from about 1:5 to about 1:10, or from about 1:10 to about 1:15. In certain embodiments, the mole to mole ratio of MMB (2) to acid anhydride may range from about 1:0.7 to about 1:3. In an exemplary embodiment, the mole to mole ratio of MMB (2) to acid anhydride may range from about 1:1.

The reaction is generally conducted in the presence of a solvent or solvent system. The solvent may be a polar aprotic solvent, a polar protic solvent, or a nonpolar solvent. Non-limiting examples of suitable polar aprotic solvents include acetone, acetonitrile, diethoxymethane, N,N-dimethylformamide (DMF), dimethyl sulfoxide (DMSO), N,N-dimethylpropanamide (or dimethylpropionamide; DMP), 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMA), N-methyl-2-pyrrolidinone (NMP), 1,4-dioxane, ethyl formate, formamide, hexachloroacetone, hexamethylphosphoramide, methyl acetate, N-methylacetamide, N-methylformamide, methylene chloride (dichloromethane, DCM), chloroform, methoxyethane, morpholine, nitrobenzene, nitromethane, propionitrile, pyridine, sulfolane, tetramethylurea, tetrahydrofuran (THF), 2-methyl tetrahydrofuran, tetrahydropyran, trichloromethane, and combinations thereof. Non-limiting examples of suitable polar protic solvents include water; alcohols such as methanol, ethanol, isopropanol, n-propanol, isobutanol, n-butanol, s-butanol, t-butanol, and the like; diols such as propylene glycol; organic acids such as formic acid, acetic acid, and so forth; amides such as formamide, acetamide, and the like; and combinations of any of the above. Representative nonpolar solvents include, but are not limited to, alkane and substituted alkane solvents (including cycloalkanes), aromatic hydrocarbons, esters, ethers, ketones, and combinations thereof. Specific polar aprotic solvents that may be employed include, for example, dichloromethane, chloroform, and combinations thereof.

A proton acceptor is generally added to facilitate the reaction. The proton acceptor generally has a pKa greater than about 7, or from about 7 to about 13, or more specifically from about 9 to about 11. Representative proton acceptors may include, but are not limited to, borate salts (such as, for example, $NaBO_3$), di- and tri-basic phosphate salts, (such as, for example, $Na_2HPO_4$ and $NaPO_4$), bicarbonate salts, carbonate salts, hydroxides, alkoxides, (including methoxide, ethoxide, propoxide, butoxide, and pentoxide, including straight chain and branched), and organic proton acceptors, (such as, for example, pyridine, triethylamine, N-methylmorpholine, and N,N-dimethylaminopyridine), and mixtures thereof. In some embodiments, the proton acceptor may be stabilized by a suitable counterion such as lithium, potassium, sodium, calcium, magnesium, and the like. In a specific embodiment, the proton acceptor is triethylamine. The amount of proton acceptor included in the reaction can and will vary, but can be readily determined by a person of ordinary skill in the art.

In general, the volume to mass ratio of the solvent to MMB (2) ranges from about 1:1 to about 100:1. In various embodiments, the volume to mass ratio of the solvent to MMB (2) may range from about 1:1 to about 5:1, from about 5:1 to about 10:1, from about 10:1 to about 20:1, from about 20:1 to about 30:1, from about 30:1 to about 40:1, from about 40:1 to about 50:1, from about 50:1 to about 60:1, from about 60:1 to about 70:1, from about 70:1 to about 80:1, from about 80:1 to about 90:1, or from about 90:1 to about 100:1. In exemplary embodiments, the volume to mass ratio of the solvent to MMB (2) may range from about 20:1 to about 30:1. In other exemplary embodiments, the volume to mass ratio of the solvent to MMB (2) may range from about 10:1 to about 20:1.

(ii) Step (a)—Reaction Conditions

In general, the reaction is conducted at a temperature that ranges from about 0° C. to about 50° C. In various embodiments, the reaction may be conducted at a temperature from about 0° C. to about 10° C., from about 10° C. to about 20° C., from about 20° C. to about 30° C., from about 30° C. to about 40° C., or from about 40° C. to about 50° C. In certain embodiments, the reaction may be conducted at a temperature of about 25° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., TLC, HPLC) or another suitable method. In this context, a "completed reaction" generally means that the reaction mixture contains a significantly diminished amount of MMB (2), and a significantly increased amount of the carboxylic acid derivative (e.g. (7)) compared to the amounts of each present at the beginning of the reaction. Typically, the amount of MMB (2) remaining in the reaction mixture after the reaction is complete may be less than about 3%, or less than about 1%. In general, the reaction may proceed for about 5 minutes to about 48 hours. Typically, the duration of the reaction is longer at lower reaction temperatures. In certain embodiments, the reaction may be allowed to proceed for about a period of time ranging from about 5 minutes to about 10 minutes, from about 10 minutes to about 15 minutes, from about 15 minutes to about 30 minutes, from about 30 minutes to about 1 hour, about 1 hour to about 3 hours, from about 3 hours to about 6 hours, from about 6 hours to about 12 hours, from about 12 hours to about 18 hours, from about 18 hours to about 24 hours, from about 24 hours to about 36 hours, or from about 36 hours to about 48 hours. In certain embodiments, the reaction may be allowed to proceed about 5 minutes to about 15 minutes. In other embodiments, the reaction may be allowed to proceed about 45 minutes to about 75 minutes. In still other embodiments, the reaction may be allowed to proceed about 18 hours to about 36 hours.

Generally, the carboxylic acid derivative is not isolated and step (b) of the process proceeds in the same reaction pot or reactor. In some embodiments, the carboxylic acid derivative may be isolated from the reaction mixture using techniques known to those of skill in the art. Non-limiting examples of suitable techniques include precipitation, extraction, evaporation, distillation, chromatography, and crystallization.

The yield of the carboxylic acid derivative can and will vary. Typically, the yield of the carboxylic acid derivative may be at least about 40%. In one embodiment, the yield of the carboxylic acid derivative may range from about 40% to about 60%. In another embodiment, the yield of the carboxylic acid derivative may range from about 60% to about 80%. In a further embodiment, the yield of the carboxylic acid derivative may range from about 80% to about 90%. In still another embodiment, the yield of the carboxylic acid derivative may be greater than about 90%, or greater than about 95%.

(iii) Step (b)—Reaction Mixture

Step (b) of the process continues with contacting the carboxylic acid derivative with a terminal alkyl diamine to form a compound comprising Formulas (I) or (III). The process commences with the formation of a reaction mixture comprising the carboxylic acid derivative, which is detailed above, a terminal alkyl diamine, and optionally a solvent system.

As used herein, a "terminal alkyl diamine" is a polyamine that comprises two amino groups on either end of an alkyl chain. The alkyl chain may be linear, branched or contain an aromatic ring. As used herein, a "terminal alkyl dihydroxyl" is an alcohol that comprises two functional hydroxyl groups on either end of an alkyl chain. The alkyl chain may be a hydrocarbyl alkyl chain or a substituted hydrocarbyl alkyl chain. The alkyl chain may be a length of 1 to 10 atoms. For example, the alkyl chain may be 1, 2, 3, 4, 5, 6, 7, 8, 9 or 10 atoms in length. In an embodiment where the alkyl chain is branched or contains an aromatic ring, the length refers to the consecutive atoms connecting the two amino groups or the two hydroxyl groups.

The amounts of the terminal alkyl diamine that are contacted with the carboxylic acid derivative may vary. In general, the mole to mole ratio of the carboxylic acid derivative to the terminal alkyl diamine may range from about 1:0.2 to about 1:15. In certain embodiments, the mole to mole ratio of the carboxylic acid derivative to the terminal alkyl diamine may range from about 1:0.2 to about 1:0.7, from about 1:0.7 to about 1:1.5, from about 1:1.5 to about 1:2.5, from about 1:2.5 to about 1:5, from about 1:5 to about 1:10, or from about 1:10 to about 1:15. In certain embodiments, the mole to mole ratio of the carboxylic acid derivative to the terminal alkyl diamine may range from about 1:0.7 to about 1:3.

Contact with the terminal alkyl diamine generally is conducted in the presence of a solvent or solvent system. Suitable solvents are detailed above in Section II(b)(i). In exemplary embodiments, the solvent may be dichloromethane, chloroform, or combinations thereof. Additionally, a proton acceptor is generally added to facilitate the reaction. Suitable proton acceptors are detailed above in Section II(b)(i). In a specific embodiment, the proton acceptor is triethylamine. Further, peptide coupling agents may also be added to the reaction. Non-limiting examples of suitable peptide coupling agents include EDC (1-Ethyl-3-(3-dimethylaminopropyl)carbodiimide)), HOBt (Hydroxybenzotriazole), DCC (N,N'-Dicyclohexylcarbodiimide), HATU ((1-[Bis(dimethylamino)methylene]-1H-1,2,3-triazolo[4,5-b]pyridinium 3-oxid hexafluorophosphate)), HBTU (O-(Benzotriazol-1-yl)-N,N,N',N'-tetramethyluronium Hexafluorophosphate), and TBTU (O-(Benzotriazol-1-yl)-N,N,N',N'-tetramethyluronium tetrafluoroborate). In an exemplary embodiment, suitable peptide coupling agents are EDC (1-Ethyl-3-(3-dimethylaminopropyl)carbodiimide)) and HOBt (Hydroxybenzotriazole).

In general, the volume to mass ratio of the solvent to the carboxylic acid derivative ranges from about 1:1 to about 100:1. In various embodiments, the volume to mass ratio of the solvent to the carboxylic acid derivative may range from about 1:1 to about 5:1, from about 5:1 to about 10:1, from about 10:1 to about 20:1, from about 20:1 to about 30:1, from about 30:1 to about 40:1, from about 40:1 to about 50:1, from about 50:1 to about 60:1, from about 60:1 to about 70:1, from about 70:1 to about 80:1, from about 80:1 to about 90:1, or from about 90:1 to about 100:1. In exemplary embodiments, the volume to mass ratio of the solvent to the carboxylic acid derivative may range from about 20:1 to about 30:1. In another exemplary embodiment, the volume to mass ratio of the solvent to the carboxylic acid derivative may range from about 10:1 to about 20:1.

(iv) Step (b)—Reaction Conditions

In general, the reaction is conducted at a temperature that ranges from about 0° C. to about 50° C. In various embodiments, the reaction may be conducted at a temperature from about 0° C. to about 10° C., from about 10° C. to about 20° C., from about 20° C. to about 30° C., from about 30° C. to about 40° C., or from about 40° C. to about 50° C. In certain embodiments, the reaction may be conducted at a temperature of about 25° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., TLC, HPLC) or another suitable method. Typically, the amount of the carboxylic acid derivative remaining in the reaction mixture after the reaction is complete may be less than about 3%, or less than about 1%. In general, the reaction may proceed for about 5 minutes to about 48 hours. Typically, the duration of the reaction is longer at lower reaction temperatures. In certain embodiments, the reaction may be allowed to proceed for about a period of time ranging from about 5 minutes to about 10 minutes, from about 10 minutes to about 15 minutes, from about 15 minutes to about 30 minutes, from about 30 minutes to about 1 hour, about 1 hour to about 3 hours, from about 3 hours to about 6 hours, from about 6 hours to about 12 hours, from about 12 hours to about 18 hours, from about 18 hours to about 24 hours, from about 24 hours to about 36 hours, or from about 36 hours to about 48 hours. In certain embodiments, the reaction may be allowed to proceed about 3 hours to about 12 hours.

The yield of the compound comprising Formulas (I) or (III) can and will vary. Typically, the yield of the compound comprising Formulas (I) or (III) may be at least about 40%. In one embodiment, the yield of the compound comprising Formulas (I) or (III) may range from about 40% to about 60%. In another embodiment, the yield of the compound comprising Formulas (I) or (III) may range from about 60% to about 80%. In a further embodiment, the yield of the compound comprising Formulas (I) or (III) may range from about 80% to about 90%. In still another embodiment, the yield of the compound comprising Formulas (I) or (III) may be greater than about 90%, or greater than about 95%.

(c) Ester Dimers of MMB

In yet other embodiments, MMB may be reacted with various terminal alkyl carbonyl chlorides (9) in the presence of triethylamine in dichloromethane to obtain the ester dimer (10) (Scheme 3). Exemplary compounds are depicted in Table 5, lines 20-21.

Scheme 3: Synthesis of cester dimers of MMB

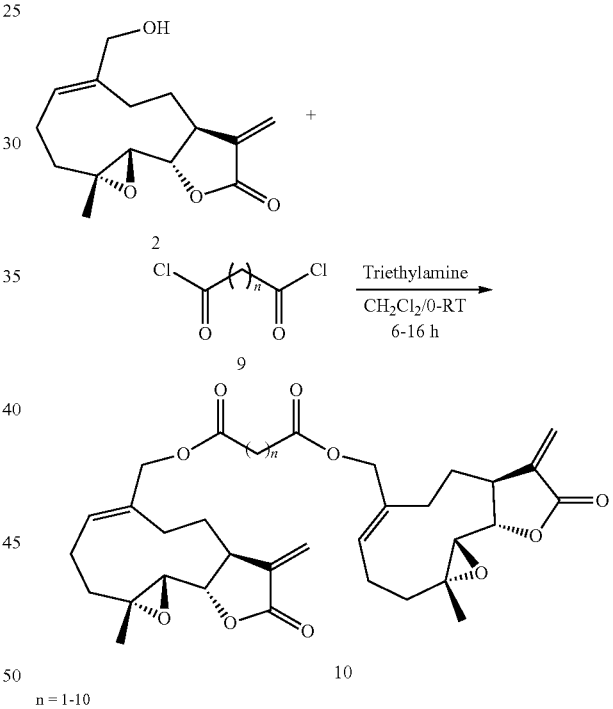

n = 1-10

In particular, provided herein are processes for preparing an ester compound comprising Formulas (I) or (IV). The process comprises contacting MMB (2) with a terminal alkyl carbonyl chloride (9) to form an ester compound comprising Formulas (I) or (IV).

(i) Reaction Mixture

The process comprises contacting MMB (2) with a terminal alkyl carbonyl chloride (9) to form an ester compound comprising Formulas (I) or (IV). The process commences with the formation of a reaction mixture comprising MMB (2), which is detailed above, the terminal alkyl carbonyl chloride, and optionally a solvent system.

As used herein, a "terminal alkyl carbonyl chloride" is a compound that comprises two acyl chloride groups (—COCl) groups on either end of an alkyl chain. The alkyl chain may be linear, branched or contain an aromatic ring. The alkyl chain may be a hydrocarbyl alkyl chain or a substituted hydrocarbyl alkyl chain. The alkyl chain may be a length of 1 to 10 atoms. For example, the alkyl chain may be 1, 2, 3, 4, 5, 6, 7, 8, 9 or 10 atoms in length. In an embodiment where the alkyl chain is branched or contains an aromatic ring, the length refers to the consecutive atoms connecting the two acyl chloride groups.

The amounts of terminal alkyl carbonyl chloride that are contacted with MMB (2) may vary. In general, the mole to mole ratio of MMB (2) to terminal alkyl carbonyl chloride may range from about 1:0.2 to about 1:15. In certain embodiments, the mole to mole ratio of MMB (2) to terminal alkyl carbonyl chloride may range from about 1:0.2 to about 1:0.7, from about 1:0.7 to about 1:1.5, from about 1:1.5 to about 1:2.5, from about 1:2.5 to about 1:5, from about 1:5 to about 1:10, or from about 1:10 to about 1:15. In certain embodiments, the mole to mole ratio of MMB (2) to terminal alkyl carbonyl chloride may range from about 1:0.7 to about 1:3.

The reaction is generally conducted in the presence of a solvent or solvent system. The solvent may be a polar aprotic solvent, a polar protic solvent, or a nonpolar solvent. Non-limiting examples of suitable polar aprotic solvents include acetone, acetonitrile, diethoxymethane, N,N-dimethylformamide (DMF), dimethyl sulfoxide (DMSO), N,N-dimethylpropanamide (or dimethylpropionamide; DMP), 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMA), N-methyl-2-pyrrolidinone (NMP), 1,4-dioxane, ethyl formate, formamide, hexachloroacetone, hexamethylphosphoramide, methyl acetate, N-methylacetamide, N-methylformamide, methylene chloride (dichloromethane, DCM), chloroform, methoxyethane, morpholine, nitrobenzene, nitromethane, propionitrile, pyridine, sulfolane, tetramethylurea, tetrahydrofuran (THF), 2-methyl tetrahydrofuran, tetrahydropyran, trichloromethane, and combinations thereof. Non-limiting examples of suitable polar protic solvents include water; alcohols such as methanol, ethanol, isopropanol, n-propanol, isobutanol, n-butanol, s-butanol, t-butanol, and the like; diols such as propylene glycol; organic acids such as formic acid, acetic acid, and so forth; amides such as formamide, acetamide, and the like; and combinations of any of the above. Representative nonpolar solvents include, but are not limited to, alkane and substituted alkane solvents (including cycloalkanes), aromatic hydrocarbons, esters, ethers, ketones, and combinations thereof. Specific polar aprotic solvents that may be employed include, for example, dichloromethane, chloroform, and combinations thereof.

A proton acceptor is generally added to facilitate the reaction. The proton acceptor generally has a pKa greater than about 7, or from about 7 to about 13, or more specifically from about 9 to about 11. Representative proton acceptors may include, but are not limited to, borate salts (such as, for example, $NaBO_3$), di- and tri-basic phosphate salts, (such as, for example, $Na_2HPO_4$ and $NaPO_4$), bicarbonate salts, carbonate salts, hydroxides, alkoxides, (including methoxide, ethoxide, propoxide, butoxide, and pentoxide, including straight chain and branched), and organic proton acceptors, (such as, for example, pyridine, triethylamine, N-methylmorpholine, and N,N-dimethylaminopyridine), and mixtures thereof. In some embodiments, the proton acceptor may be stabilized by a suitable counterion such as lithium, potassium, sodium, calcium, magnesium, and the like. In a specific embodiment, the proton acceptor is triethylamine. The amount of proton acceptor included in the reaction can and will vary, but can be readily determined by a person of ordinary skill in the art.

In general, the volume to mass ratio of the solvent to MMB (2) ranges from about 1:1 to about 100:1. In various embodiments, the volume to mass ratio of the solvent to MMB (2) may range from about 1:1 to about 5:1, from about 5:1 to about 10:1, from about 10:1 to about 20:1, from about 20:1 to about 30:1, from about 30:1 to about 40:1, from about 40:1 to about 50:1, from about 50:1 to about 60:1, from about 60:1 to about 70:1, from about 70:1 to about 80:1, from about 80:1 to about 90:1, or from about 90:1 to about 100:1. In exemplary embodiments, the volume to mass ratio of the solvent to MMB (2) may range from about 20:1 to about 30:1.

(ii) Reaction Conditions

In general, the reaction is conducted at a temperature that ranges from about 0° C. to about 50° C. In various embodiments, the reaction may be conducted at a temperature from about 0° C. to about 10° C., from about 10° C. to about 20° C., from about 20° C. to about 30° C., from about 30° C. to about 40° C., or from about 40° C. to about 50° C. In certain embodiments, the reaction may be conducted at a temperature of about 25° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., TLC, HPLC) or another suitable method. In this context, a "completed reaction" generally means that the reaction mixture contains a significantly diminished amount of MMB (2), and a significantly increased amount of the ester dimer of Formulas (I) or (IV) compared to the amounts of each present at the beginning of the reaction. Typically, the amount of MMB (2) remaining in the reaction mixture after the reaction is complete may be less than about 3%, or less than about 1%. In general, the reaction may proceed for about 5 minutes to about 48 hours. Typically, the duration of the reaction is longer at lower reaction temperatures. In certain embodiments, the reaction may be allowed to proceed for about a period of time ranging from about 5 minutes to about 10 minutes, from about 10 minutes to about 15 minutes, from about 15 minutes to about 30 minutes, from about 30 minutes to about 1 hour, about 1 hour to about 3 hours, from about 3 hours to about 6 hours, from about 6 hours to about 12 hours, from about 12 hours to about 18 hours, from about 18 hours to about 24 hours, from about 24 hours to about 36 hours, or from about 36 hours to about 48 hours. In certain embodiments, the reaction may be allowed to proceed about 5 minutes to about 15 minutes. In other embodiments, the reaction may be allowed to proceed about 45 minutes to about 75 minutes. In still other embodiments, the reaction may be allowed to proceed about 6 hours to about 16 hours.

The yield of the compound comprising Formulas (I) or (IV) can and will vary. Typically, the yield of the compound comprising Formulas (I) or (IV) may be at least about 40%. In one embodiment, the yield of the compound comprising Formulas (I) or (IV) may range from about 40% to about 60%. In another embodiment, the yield of the compound comprising Formulas (I) or (IV) may range from about 60% to about 80%. In a further embodiment, the yield of the compound comprising Formulas (I) or (IV) may range from about 80% to about 90%. In still another embodiment, the yield of the compound comprising Formulas (I) or (IV) may be greater than about 90%, or greater than about 95%.

(d) Carboxylic Amide Dimers of Melampomagnolic Acid

In still other embodiments, parthenolide (1) C10 methyl group may be oxidized via treatment with selenium dioxide to form compounds (2), (11) and (3) (Scheme 4). The carboxylic acid derivative (3) may be reacted with various terminal alkyl diamines to afford the corresponding carboxylic amide dimers of melampomagnolic acid (12) (Scheme 5). Exemplary compounds are depicted in Table 5, lines 22-27.

Scheme 4: Oxidation of the C10 methyl group of parthenolide to form melampomagnolic acid (3)

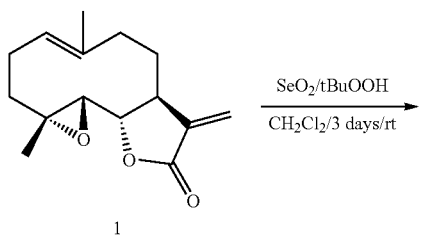

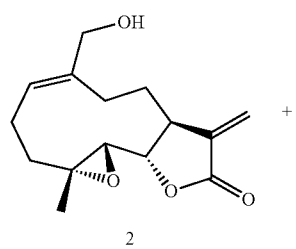

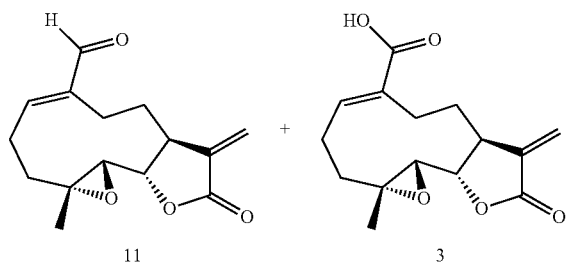

Scheme 5: synthesis of carboxamide dimers of melampomagnolic acid

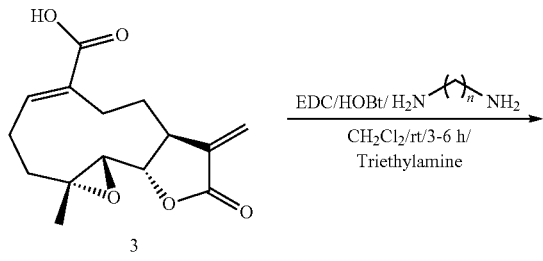

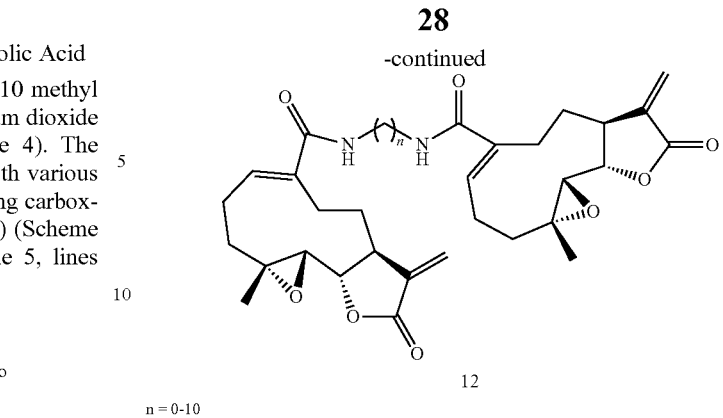

n = 0-10

In particular, provided herein are processes for preparing a carboxamide compound comprising Formulas (I) or (V). The process comprises (a) oxidizing parthenolide (PTL) to form a carboxylic acid derivative of melampomagnolic acid (3). The process continues with (b) contacting the carboxylic acid derivative with a terminal alkyl diamine to form a carboxamide compound comprising Formulas (I) or (V).

(i) Step (a)—Reaction Mixture

Step (a) of the process comprises oxidizing PTL (1) to form a carboxylic acid derivative (3). The process commences with the formation of a reaction mixture comprising PTL (1), which is detailed above, an oxidizing agent, and optionally a solvent system.

The oxidizing agent may be any compound which reacts with the C10 methyl group to provide an oxidized carboxylic acid derivative. Non-limiting examples of suitable oxidizing agents include selenium dioxide ($SeO_2$), potassium permanganate ($KMnO_4$), osmium tetroxide ($OsO_4$), and chromic acid ($H_2CrO_4$). In an exemplary embodiment, the oxidizing agent is selenium dioxide ($SeO_2$).

The amounts of oxidizing agent that are contacted with PTL (1) may vary. In general, the mole to mole ratio of PTL (1) to oxidizing agent may range from about 1:0.2 to about 1:15. In certain embodiments, the mole to mole ratio of PTL (1) to oxidizing agent may range from about 1:0.2 to about 1:0.7, from about 1:0.7 to about 1:1.5, from about 1:1.5 to about 1:2.5, from about 1:2.5 to about 1:5, from about 1:5 to about 1:10, or from about 1:10 to about 1:15. In certain embodiments, the mole to mole ratio of PTL (1) to oxidizing agent may range from about 1:0.7 to about 1:3. In an exemplary embodiment, the mole to mole ratio of PTL (1) to oxidizing agent may be about 1:1.5.

The reaction is generally conducted in the presence of a solvent or solvent system. The solvent may be a polar aprotic solvent, a polar protic solvent, or a nonpolar solvent. Non-limiting examples of suitable polar aprotic solvents include acetone, acetonitrile, diethoxymethane, N,N-dimethylformamide (DMF), dimethyl sulfoxide (DMSO), N,N-dimethylpropanamide (or dimethylpropionamide; DMP), 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMA), N-methyl-2-pyrrolidinone (NMP), 1,4-dioxane, ethyl formate, formamide, hexachloroacetone, hexamethylphosphoramide, methyl acetate, N-methylacetamide, N-methylformamide, methylene chloride (dichloromethane, DCM), chloroform, methoxyethane, morpholine, nitrobenzene, nitromethane, propionitrile, pyridine, sulfolane, tetramethylurea, tetrahydrofuran (THF), 2-methyl tetrahydrofuran, tetrahydropyran, trichloromethane, and combinations thereof. Non-limiting examples of suitable polar protic solvents include water; alcohols such as methanol, ethanol, isopropanol, n-propanol, isobutanol, n-butanol, s-butanol, t-butanol, and the like; diols such as propylene glycol; organic acids such as formic acid, acetic acid, and so forth; amides such as formamide, acetamide, and the like; and combinations of any of the above. Representative nonpolar solvents include, but are not limited to, alkane and substituted alkane solvents (including cycloalkanes), aromatic hydrocarbons, esters, ethers, ketones, and combinations thereof. Specific polar aprotic solvents that may be employed include, for example, dichloromethane, chloroform, and combinations thereof.

Further, tert-butyl hydroperoxide (tBuOOH) may also be added to the reaction. tBuOOH is used as a starter of radical polymerization. Accordingly, any other compound capable of radical polymerization may be used. By way of non-limiting example, other organic peroxides such as ethyl hydroperoxide, acetyl benzoyl peroxide and diacetyl peroxide.

In general, the volume to mass ratio of the solvent to PTL (1) ranges from about 1:1 to about 100:1. In various embodiments, the volume to mass ratio of the solvent to PTL (1) may range from about 1:1 to about 5:1, from about 5:1 to about 10:1, from about 10:1 to about 20:1, from about 20:1 to about 30:1, from about 30:1 to about 40:1, from about 40:1 to about 50:1, from about 50:1 to about 60:1, from about 60:1 to about 70:1, from about 70:1 to about 80:1, from about 80:1 to about 90:1, or from about 90:1 to about 100:1. In exemplary embodiments, the volume to mass ratio of the solvent to PTL (1) may range from about 10:1 to about 20:1.

(ii) Step (a)—Reaction Conditions

In general, the reaction is conducted at a temperature that ranges from about 0° C. to about 50° C. In various embodiments, the reaction may be conducted at a temperature from about 0° C. to about 10° C., from about 10° C. to about 20° C., from about 20° C. to about 30° C., from about 30° C. to about 40° C., or from about 40° C. to about 50° C. In certain embodiments, the reaction may be conducted at a temperature of about 25° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., TLC, HPLC) or another suitable method. In this context, a "completed reaction" generally means that the reaction mixture contains a significantly diminished amount of PTL (1), and a significantly increased amount of the carboxylic acid derivative (3) compared to the amounts of each present at the beginning of the reaction. Typically, the amount of PTL (1) remaining in the reaction mixture after the reaction is complete may be less than about 3%, or less than about 1%. In general, the reaction may proceed for about 5 minutes to about 96 hours. Typically, the duration of the reaction is longer at lower reaction temperatures. In certain embodiments, the reaction may be allowed to proceed for about a period of time ranging from about 5 minutes to about 10 minutes, from about 10 minutes to about 15 minutes, from about 15 minutes to about 30 minutes, from about 30 minutes to about 1 hour, about 1 hour to about 3 hours, from about 3 hours to about 6 hours, from about 6 hours to about 12 hours, from about 12 hours to about 18 hours, from about 18 hours to about 24 hours, from about 24 hours to about 36 hours, from about 36 hours to about 48 hours, from about 48 hour to about 72 hours, or from about 72 hours to about 96 hours. In certain embodiments, the reaction may be allowed to proceed about 36 hours to about 48 hours. In other embodiments, the reaction may be allowed to proceed about 48 hours to about 72 hours. In still other embodiments, the reaction may be allowed to proceed about 72 hours to about 96 hours.

Generally, the carboxylic acid derivative is not isolated and step (b) of the process proceeds in the same reaction pot or reactor. In some embodiments, the carboxylic acid derivative may be isolated from the reaction mixture using techniques known to those of skill in the art. Non-limiting examples of suitable techniques include precipitation, extraction, evaporation, distillation, chromatography, and crystallization.

The yield of the carboxylic acid derivative can and will vary. Typically, the yield of the carboxylic acid derivative may be at least about 40%. In one embodiment, the yield of the carboxylic acid derivative may range from about 40% to about 60%. In another embodiment, the yield of the carboxylic acid derivative may range from about 60% to about 80%. In a further embodiment, the yield of the carboxylic acid derivative may range from about 80% to about 90%. In still another embodiment, the yield of the carboxylic acid derivative may be greater than about 90%, or greater than about 95%.

(iii) Step (b)—Reaction Mixture

Step (b) of the process continues with contacting the carboxylic acid derivative with a terminal alkyl diamine to form a compound comprising Formulas (I) or (V). The process commences with the formation of a reaction mixture comprising the carboxylic acid derivative, which is detailed above, a terminal alkyl diamine, and optionally a solvent system.

As used herein, a "terminal alkyl diamine" is a polyamine that comprises two amino groups on either end of an alkyl chain. The alkyl chain may be linear, branched or contain an aromatic ring. As used herein, a "terminal alkyl dihydroxyl" is an alcohol that comprises two functional hydroxyl groups on either end of an alkyl chain. The alkyl chain may be a hydrocarbyl alkyl chain or a substituted hydrocarbyl alkyl chain. The alkyl chain may be a length of 1 to 10 atoms. For example, the alkyl chain may be 1, 2, 3, 4, 5, 6, 7, 8, 9 or 10 atoms in length. In an embodiment where the alkyl chain is branched or contains an aromatic ring, the length refers to the consecutive atoms connecting the two amino groups or the two hydroxyl groups.

The amounts of the terminal alkyl diamine that are contacted with the carboxylic acid derivative may vary. In general, the mole to mole ratio of the carboxylic acid derivative to the terminal alkyl diamine may range from about 1:0.2 to about 1:15. In certain embodiments, the mole to mole ratio of the carboxylic acid derivative to the terminal alkyl diamine may range from about 1:0.2 to about 1:0.7, from about 1:0.7 to about 1:1.5, from about 1:1.5 to about 1:2.5, from about 1:2.5 to about 1:5, from about 1:5 to about 1:10, or from about 1:10 to about 1:15. In certain embodiments, the mole to mole ratio of the carboxylic acid derivative to the terminal alkyl diamine may range from about 1:0.7 to about 1:3.

Contact with the carboxylic acid derivative generally is conducted in the presence of a solvent or solvent system. Suitable solvents are detailed above in Section II(d)(i). In exemplary embodiments, the solvent may be dichloromethane, chloroform, or combinations thereof.

A proton acceptor is generally added to facilitate the reaction. The proton acceptor generally has a pKa greater than about 7, or from about 7 to about 13, or more specifically from about 9 to about 11. Representative proton acceptors may include, but are not limited to, borate salts (such as, for example, NaBO$_3$), di- and tri-basic phosphate salts, (such as, for example, Na$_2$HPO$_4$ and NaPO$_4$), bicarbonate salts, carbonate salts, hydroxides, alkoxides, (including methoxide, ethoxide, propoxide, butoxide, and pentoxide, including straight chain and branched), and organic proton acceptors, (such as, for example, pyridine, triethylamine, N-methylmorpholine, and N,N-dimethylaminopyridine), and mixtures thereof. In some embodiments, the proton acceptor may be stabilized by a suitable counterion such as lithium, potassium, sodium, calcium, magnesium, and the like. In a specific embodiment, the proton acceptor is triethylamine. The amount of proton acceptor included in the reaction can and will vary, but can be readily determined by a person of ordinary skill in the art.

Further, peptide coupling agents may also be added to the reaction. Non-limiting examples of suitable peptide coupling agents include EDC (1-Ethyl-3-(3-dimethylaminopropyl)carbodiimide)), HOBt (Hydroxybenzotriazole), DCC (N,N'-Dicyclohexylcarbodiimide), HATU ((1-[Bis(dimethylamino)methylene]-1H-1,2,3-triazolo[4,5-b]pyridinium 3-oxid hexafluorophosphate)), HBTU (O-(Benzotriazol-1-yl)-N,N,N',N'-tetramethyluronium Hexafluorophosphate), and TBTU (O-(Benzotriazol-1-yl)-N,N,N',N'-tetramethyluronium tetrafluoroborate). In an exemplary embodiment, suitable peptide coupling agents are EDC (1-Ethyl-3-(3-dimethylaminopropyl)carbodiimide)) and HOBt (Hydroxybenzotriazole).

In general, the volume to mass ratio of the solvent to the carboxylic acid derivative ranges from about 1:1 to about 100:1. In various embodiments, the volume to mass ratio of the solvent to the carboxylic acid derivative may range from about 1:1 to about 5:1, from about 5:1 to about 10:1, from about 10:1 to about 20:1, from about 20:1 to about 30:1, from about 30:1 to about 40:1, from about 40:1 to about 50:1, from about 50:1 to about 60:1, from about 60:1 to about 70:1, from about 70:1 to about 80:1, from about 80:1 to about 90:1, or from about 90:1 to about 100:1. In exemplary embodiments, the volume to mass ratio of the solvent to the carboxylic acid derivative may range from about 10:1 to about 20:1. In other exemplary embodiments, the volume to mass ratio of the solvent to the carboxylic acid derivative may range from about 5:1 to about 10:1.

(iv) Step (b)—Reaction Conditions

In general, the reaction is conducted at a temperature that ranges from about 0° C. to about 50° C. In various embodiments, the reaction may be conducted at a temperature from about 0° C. to about 10° C., from about 10° C. to about 20° C., from about 20° C. to about 30° C., from about 30° C. to about 40° C., or from about 40° C. to about 50° C. In certain embodiments, the reaction may be conducted at a temperature of about 25° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., TLC, HPLC) or another suitable method. Typically, the amount of the carboxylic acid derivative remaining in the reaction mixture after the reaction is complete may be less than about 3%, or less than about 1%. In general, the reaction may proceed for about 5 minutes to about 48 hours. Typically, the duration of the reaction is longer at lower reaction temperatures. In certain embodiments, the reaction may be allowed to proceed for about a period of time ranging from about 5 minutes to about 10 minutes, from about 10 minutes to about 15 minutes, from about 15 minutes to about 30 minutes, from about 30 minutes to about 1 hour, about 1 hour to about 3 hours, from about 3 hours to about 6 hours, from about 6 hours to about 12 hours, from about 12 hours to about 18 hours, from about 18 hours to about 24 hours, from about 24 hours to about 36 hours, or from about 36 hours to about 48 hours. In certain embodiments, the reaction may be allowed to proceed about 3 hours to about 12 hours. In other embodiments, the reaction may be allowed to proceed about 3 hours to about 6 hours.

The yield of the compound comprising Formulas (I) or (V) can and will vary. Typically, the yield of the compound comprising Formulas (I) or (V) may be at least about 40%. In one embodiment, the yield of the compound comprising Formulas (I) or (V) may range from about 40% to about 60%. In another embodiment, the yield of the compound comprising Formulas (I) or (V) may range from about 60% to about 80%. In a further embodiment, the yield of the compound comprising Formulas (I) or (V) may range from about 80% to about 90%. In still another embodiment, the yield of the compound comprising Formulas (I) or (V) may be greater than about 90%, or greater than about 95%.

III. Compositions

The present disclosure also provides pharmaceutical compositions. The pharmaceutical composition comprises a compound comprising Formulas (I), (II), (III), (IV) or (V) which is detailed above in Section I, as an active ingredient and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18$^{th}$ ed, 1995), and Liberman, H. A. and Lachman, L., Eds., Pharmaceutical Dosage Forms, Marcel Dekker Inc., New York, N.Y. (1980).

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

For topical (e.g., transdermal or transmucosal) administration, penetrants appropriate to the barrier to be permeated are generally included in the preparation. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising a compound of the invention is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of the compound of the invention in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the compound of the invention may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally, contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetonitrile, alcohols, dimethylformamide, tetrahydrofuran, or combinations thereof.

Liposomes carrying the compound of the invention (i.e., having at least one methionine compound) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The composition of the invention may be encapsulated in a microemulsion by any method generally known in the art.

In yet another embodiment, a composition of the invention may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

IV. Methods for Inhibiting Cancer Cell Growth

A further aspect of the present disclosure provides a method for inhibiting growth of a cancer cell. Cancer cell growth includes cell proliferation and cell metastasis. The method comprises contacting the cancer cell with an effective amount of a compound comprising Formulas (I), (II), (III), (IV) or (V), or a pharmaceutically acceptable salt thereof, wherein the amount is effective to inhibit growth of the cancer cell. Compounds comprising Formulas (I), (II), (III), (IV) or (V) are detailed above in Section I. In some embodiments, the compound comprising Formulas (I), (II), (III), (IV) or (V) is used as part of a composition, examples of which are detailed above in Section III.

(a) Contacting the Cell

In some embodiments, the cancer cell may be in vitro. The cancer cell may be an established, commercially-available cancer cell line (e.g., American Type Culture Collection (ATCC), Manassas, Va.). The cancer cell line may be derived from a blood cancer or a solid tumor. The cancer cell line may be a human cell line or a mammalian cell line. In a specific embodiment, the cancer cell line may be derived from a blood cancer. In one exemplary embodiment, the cancer cell line may be derived from a leukemic cell. The leukemic cell may be an acute myeloid leukemia cell, a chronic myeloid leukemia cell, an acute lymphocytic leukemia cell, a chronic lymphocytic leukemia cell, a cutaneous T cell leukemia, or another type of leukemia cell. In some embodiments, the cancer cell line may be a leukemia cell line such as CCRF-CEM, HL-60(TB), K-562, MOLT-4, RPMI-8226, or SR. In other embodiments, the cancer cell line may be a hematopoietic or lymphoid cell line. Non-limiting examples of hematopoietic or lymphoid cell lines include 380, 697, A3-KAW, A3/KAW, A4-Fuk, A4/Fuk, ALL-PO, ALL-SIL, AML-193, AMO-1, ARH-77, ATN-1, BALL-1, BC-3, BCP-1, BDCM, BE-13, BL-41, BL-70, BV-173, C8166, CA46, CCRF-CEM, Cl-1, CMK, CMK-11-5, CMK-86, CML-T1, COLO 775, COLO-677, CTB-1, CTV-1, Daudi, DB, DEL, DG-75, DND-41, DOHH-2, EB1, EB2, EHEB, EJM, EM-2, EOL-1, EoL-1-cell, F-36P, GA-10, GA-10-Clone-4, GDM-1, GR-ST, GRANTA-519, H9, HAL-01, HD-MY-Z, HDLM-2, HEL, HEL 92.1.7, HH, HL-60, HPB-ALL, Hs 604.T, Hs 611.T, Hs 616.T, Hs 751.T, HT, HTK-, HuNS1, HuT 102, HuT 78, IM-9, J-RT3-T3-5, JeKo-1, JiyoyeP-2003, JJN-3, JK-1, JM1, JURKAT, JURL-MK1, JVM-2, JVM-3, K-562, K052, KARPAS-299, KARPAS-422, KARPAS-45, KARPAS-620, KASUMI-1, KASUMI-2, Kasumi-6, KCL-22, KE-37, KE-97, KG-1, KHM-1B, Ki-JK, KM-H2, KMM-1, KMOE-2, KMS-11, KMS-12-BM, KMS-12-PE, KMS-18, KMS-20, KMS-21BM, KMS-26, KMS-27, KMS-28BM, KMS-34, KO52, KOPN-8, KU812, KY821, KYO-1, L-1236, L-363, L-428, L-540, LAMA-84, LC4-1, Loucy, LOUCY, LP-1, M-07e, MC-CAR, MC116, ME-1, MEC-1, MEC-2, MEG-01, MHH-CALL-2, MHH-CALL-3, MHH-CALL-4, MHH-PREB-1, Mino, MJ, ML-2, MLMA, MM1-S, MN-60, MOLM-13, MOLM-16, MOLM-6, MOLP-2, MOLP-8, MOLT-13, MOLT-16, MOLT-4, MONO-MAC-1, MONO-MAC-6, MOTN-1, MUTZ-1, MUTZ-3, MUTZ-5, MV-4-11, NALM-1, NALM-19, NALM-6, NAMALWA, NB-4, NCI-H929, NCO2, NKM-1, NOMO-1, NU-DHL-1, NU-DUL-1, OCI-AML2, OCI-AML3, OCI-AML5, OCI-LY-19, OCI-LY10, OCI-LY3, OCI-M1, OPM-2, P12-ICHIKAWA, P30-OHK, P31-FUJ, P31/FUJ, P3HR-1, PCM6, PEER, PF-382, Pfeiffer, PL-21, Raji, Ramos-2G6-4C10, RCH-ACV, REC-1, Reh, REH, RI-1, RL, RPMI 8226, RPMI-8226, RPMI-8402, RS4-11, "RS4;11", SEM, Set-2, SIG-M5, SK-MM-2, SKM-1, SR, SR-786, ST486, SU-DHL-1, SU-DHL-10, SU-DHL-4, SU-DHL-5, SU-DHL-6, SU-DHL-8, SUP-B15, SUP-B8, SUP-HD1, SUP-M2, SUP-T1, SUP-T11, TALL-1, TF-1, THP-1, TO 175.T, Toledo, TUR, U-266, U-698-M, U-937, U266B1, UT-7, WSU-DLCL2, and WSU-NHL.

In another exemplary embodiment, the cancer cell line may be derived from a solid tumor cell. The solid tumor cell may be a non-small cell lung cancer, colon cancer, CNS cancer, melanoma cancer, ovarian cancer, renal cancer, prostate cancer, breast cancer, or another type of solid tumor cell. In some embodiments, the cancer cell line may be a non-small cell lung cancer cell line such as A549/ATCC, HOP-92, NCI-H226, NCI-H23, NCI-H322M, NCI-H460, or NCI-H522. In other embodiments, the cancer cell line may be a colon cancer cell line such as COLO 205, HCC-2998, HCT-116, HCT-15, HT29, KM12 or SW-620. In different embodiments, the cancer cell line may be a CNS cancer cell line such as SF-268, SF-295, SF-539, SNB-19, SNB-75 or U251. In some other embodiments, the cancer cell line may be a melanoma cell line such as LOX IMVI, MALME-3M, M14, MDA-MB-435, SK-MEL-2, SK-MEL-28, SK-MEL-5, UACC-257, or UACC-62. In still other embodiments, the cancer cell line may be an ovarian cancer cell line such as OVCAR-3, OVCAR-4, OVCAR-5, OVCAR-8, NCI/ADR-RES, or SK-OV-3. In some different embodiments, the cancer cell line may be a renal cancer cell line such as 786-0, A498, ACHN, CAK1-1, RXF 393, SN12C, TK-10, or UO-31. In other embodiments, the cancer cell line may be a prostate cancer cell line such as PC-3 or DU-145. In some embodiments, the cancer cell line may be a breast cancer cell line such as MCF7, MDA-BM-231/ATCC, HS 578T, BT-549, T-47D, or MDA-MB-468.

In other embodiments, the cancer cell may be in vivo; i.e., the cell may be disposed in a subject. In such embodiments, the cancer cell is contacted with the compound comprising Formulas (I), (II), (III), (IV) or (V) by administering the compound comprising Formulas (I), (II), (III), (IV) or (V) to the subject. In some embodiments, the subject may be a human. In other embodiments, the subject may be a non-human animal. Non-limiting examples of non-human animals include companion animals (e.g., cats, dogs, horses, rabbits, gerbils), agricultural animals (e.g., cows, pigs, sheep, goats, fowl), research animals (e.g., rats, mice, rabbits, primates), and zoo animals (e.g., lions, tiger, elephants, and the like).

The cancer cell disposed in the subject may be a blood cancer cell (e.g., leukemia, lymphoma, myeloma) or a solid tumor cancer cell. The cancer may be primary or metastatic; early stage or late stage; and/or the tumor may be malignant or benign. Non-limiting cancers include bladder cancer, bone cancer, brain cancer, breast cancer, central nervous system cancer, cervical cancer, colon cancer, colorectal cancer, duodenal cancer, endometrial cancer, esophageal cancer, eye cancer, gallbladder cancer, germ cell cancer, kidney cancer, larynx cancer, leukemia, liver cancer, lymphoma, lung cancer, melanoma, mouth/throat cancer, ovarian cancer, pancreatic cancer, prostate cancer, skin cancer, testicular cancer, thyroid cancer, vaginal cancer, and drug resistant cancers. In one exemplary embodiment, the cancer cell may be a leukemia. The leukemia may be an acute lymphocytic (lymphoblastic) leukemia, a chronic lymphocytic leukemia, an acute myeloid leukemia, a chronic myeloid leukemia, a hairy cell leukemia, a T-cell prolymphocytic leukemia, a large granular lymphocytic leukemia, or an adult T-cell leukemia. In another exemplary embodiment, the cancer cell may be a solid tumor cancer cell selected from the group consisting of non-small cell lung cancer, colon cancer, melanoma cancer, ovarian cancer, renal cancer, breast cancer.

The compound comprising Formulas (I), (II), (III), (IV) or (V) may be administered to the subject orally (as a solid or a liquid), parenterally (which includes intramuscular, intravenous, intradermal, intraperitoneal, and subcutaneous), or topically (which includes transmucosal and transdermal). An effective amount of the compound can be determined by a skilled practitioner in view of desired dosages and potential side effects of the compound.

The compound comprising Formulas (I), (II), (III), (IV) or (V) may be administered once or administered repeatedly to the subject. Repeated administrations may be at regular intervals of 2 hours, 6 hours, 12 hours, 24 hours, 2 days, 5 days, 7 days, 30 days, and so forth.

(b) Inhibiting Cancer Cell Growth

Following contact with an effective amount of the compound comprising Formulas (I), (II), (III), (IV) or (V), growth of the cancer cell is inhibited. Cell growth or proliferation can be measured in cells grown in vitro using standard cell viability or cell cytotoxicity assays (e.g., based on DNA content, cell permeability, etc.) in combination with cell counting methods (e.g., flow cytometry, optical density). Cell growth or proliferation can be measured in vivo using imaging procedures and/or molecular diagnostic indicators.

In an embodiment, contact with an effective amount of the compound comprising Formulas (I), (II), (III), (IV) or (V) selectively inhibits growth of cancer cells. As such, a compound comprising Formulas (I), (II), (III), (IV) or (V) does not appreciably kill non-cancer cells at the same concentration. Accordingly, more than 50% of non-cancer cells remain viable following contact with a compound comprising Formulas (I), (II), (III), (IV) or (V) at the same concentration. For example about 50%, about 55%, about 60%, about 65%, about 70%, about 75%, about 80%, about 85%, about 90%, about 95% or about 100% of non-cancer cells remain viable following contact with a compound comprising Formulas (I), (II), (III), (IV) or (V) at the same concentration. Or, 50%, 55%, 60%, 65%, 70%, 75%, 80%, 85%, 90%, 95% or 100% of non-cancer cells remain viable following contact with a compound comprising Formulas (I), (II), (III), (IV) or (V) at the same concentration.

In various embodiments, cancer cell growth may be inhibited about 0.5-fold, about 1-fold, about 2-fold, about 3-fold, about 4-fold, about 5-fold, about 8-fold, about 10-fold, or more than 10-fold relative to a reference value. In various other embodiments, cancer cell growth may be inhibited 0.5-fold, 1-fold, 2-fold, 3-fold, 4-fold, 5-fold, 8-fold, 10-fold, or more than 10-fold relative to a reference value. In other embodiments, cancer cell growth may be inhibited to such a degree that the cell undergoes cell death (via apoptosis or necrosis). Any suitable reference value known in the art may be used. For example, a suitable reference value may be cancer cell growth in a sample that has not been contacted with a compound comprising Formulas (I), (II), (III), (IV) or (V). In another example, a suitable reference value may be the baseline growth rate of the cells as determined by methods known in the art. In another example, a suitable reference value may be a measurement of the number of cancer cells in a reference sample obtained from the same subject. For example, when monitoring the effectiveness of a therapy or efficacy of a compound comprising Formulas (I), (II), (III), (IV) or (V), a reference sample may be a sample obtained from a subject before therapy or administration of the compound comprising Formulas (I), (II), (III), (IV) or (V) began.

(c) Optional Contact

In certain embodiments, the method may further comprise contacting the cell with at least one chemotherapeutic agent and/or a radiotherapeutic agent. The chemotherapeutic agent and/or radiotherapeutic agent may be administered concurrently or sequentially with the compound comprising Formulas (I), (II), (III), (IV) or (V).

The chemotherapeutic agent may be an alkylating agent, an anti-metabolite, an anti-tumor antibiotic, an anti-cytoskeletal agent, a topoisomerase inhibitor, an anti-hormonal agent, a targeted therapeutic agent, or a combination thereof. Non-limiting examples of suitable alkylating agents include altretamine, benzodopa, busulfan, carboplatin, carboquone, carmustine (BCNU), chlorambucil, chlornaphazine, cholophosphamide, chlorozotocin, cisplatin, cyclosphosphamide, dacarbazine (DTIC), estramustine, fotemustine, ifosfamide, improsulfan, lomustine (CCNU), mechlorethamine, mechlorethamine oxide hydrochloride, melphalan, meturedopa, nimustine, novembichin, phenesterine, pipobsulfan, prednimustine, ranimustine; temozolomide, thiotepa, triethylenemelamine, trietylenephosphoramide, triethylenethiophosphaoramide, trimethylolomelamine, trofosfamide, uracil mustard and uredopa. Suitable anti-metabolites include, but are not limited to aminopterin, ancitabine, azacitidine, 6-azauridine, capecitabine, carmofur (1-hexylcarbomoyl-5-fluorouracil), cladribine, cytarabine or cytosine arabinoside (Ara-C), dideoxyuridine, denopterin, doxifluridine, enocitabine, floxuridine, fludarabine, 5-fluorouracil, gemcetabine, hydroxyurea, leucovorin (folinic acid), 6-mercaptopurine, methotrexate, pemetrexed, pteropterin, thiamiprine, trimetrexate, and thioguanine. Non-limiting examples of suitable anti-tumor antibiotics include aclacinomysin, actinomycins, adriamycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mithramycin, mycophenolic acid, nogalamycin, olivomycins, peplomycin, plicamycin, potfiromycin, puromycin, quelamycin, rodorubicin, streptonigrin, streptozocin, tubercidin, valrubicin, ubenimex, zinostatin, and zorubicin. Non-limiting examples of suitable anti-cytoskeletal agents include colchicines, docetaxel, macromycin, paclitaxel, vinblastine, vincristine, vindesine, and vinorelbine. Suitable topoisomerase inhibitors include, but are not limited to, amsacrine, etoposide (VP-16), irinotecan, mitoxantrone, RFS 2000, teniposide, and topotecan. Non-limiting examples of suitable anti-hormonal agents such as aminoglutethimide, aromatase inhibiting 4(5)-imidazoles, bicalutamide, finasteride, flutamide, goserelin, 4-hydroxytamoxifen, keoxifene, leuprolide, LY117018, mitotane, nilutamide, onapristone, raloxifene, tamoxifen, toremifene, and trilostane. Examples of targeted therapeutic agents include, without limit, monoclonal antibodies such as alemtuzumab, epratuzumab, gemtuzumab, ibritumomab tiuxetan, rituximab, tositumomab, and trastuzumab; protein kinase inhibitors such as bevacizumab, cetuximab, dasatinib, erlotinib, gefitinib, imatinib, lapatinib, mubritinib, nilotinib, panitumumab, pazopanib, sorafenib, sunitinib, and vandetanib; angiogeneisis inhibitors such as angiostatin, endostatin, bevacizumab, genistein, interferon alpha, interleukin-2, interleukin-12, pazopanib, pegaptanib, ranibizumab, rapamycin, thalidomide; and growth inhibitory polypeptides such as erythropoietin, interleukins (e.g., IL-1, IL-2, IL-3, IL-6), leukemia inhibitory factor, interferons, thrombopoietin, TNF-α, CD30 ligand, 4-1BB ligand, and Apo-1 ligand. Also included are pharmaceutically acceptable salts, acids, or derivatives of any of the above listed agents. The mode of administration of the chemotherapeutic agent can and will vary depending upon the agent and the type of cancer. A skilled practitioner will be able to determine the appropriate dose of the chemotherapeutic agent.

The radiotherapeutic agent may include a radioisotope. Suitable radioisotopes include, without limit, Iodine-131, Iodine-125, Iodine-124, Lutecium-177, Phosphorous-132, Rhenium-186, Strontium-89, Yttrium-90, Iridium-192, and Samarium-153. Alternatively, the radiotherapeutic agent may include a high Z-element chosen from gold, silver, platinum, palladium, cobalt, iron, copper, tin, tantalum, vanadium, molybdenum, tungsten, osmium, iridium, rhenium, hafnium, thallium, lead, bismuth, gadolinium, dysprosium, holmium, and uranium. The appropriate dose of the radiotherapeutic agent may be determined by a skilled practitioner.

Definitions

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like. The "substituted alkyl" moieties described herein are alkyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "oxygen-protecting group" as used herein denotes a group capable of protecting an oxygen atom (and hence, forming a protected hydroxyl group), wherein the protecting group may be removed, subsequent to the reaction for which protection is employed, without disturbing the remainder of the molecule. Exemplary oxygen protecting groups include ethers (e.g., allyl, triphenylmethyl (trityl or Tr), p-methoxybenzyl (PMB), p-methoxyphenyl (PMP)); acetals (e.g., methoxymethyl (MOM), 1-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)); esters (e.g., benzoate (Bz), allyl carbonate, 2,2,2-trichloroethyl carbonate (Troc), 2-trimethylsilylethyl carbonate); silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS)) and the like. A variety of oxygen protecting groups and the synthesis thereof may be found in "Protective Groups in Organic Synthesis" by T. W. Greene and P. G. M. Wuts, $3^{rd}$ ed., John Wiley & Sons, 1999.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate certain embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Example 1

Carbamate and Carbonate Dimers of Melampomagnolide B

Carbamate dimers of MMB (2) were prepared via the triazole intermediate 5. To obtain this intermediate, MMB (2) was reacted with carbonylditriazole (4) in the presence of dichloromethane as solvent at ambient temperature. This intermediate was reacted with various terminal alkyl diamines to obtain the corresponding carbamate dimer of MMB (6; X=NH), or with terminal alkyl dihydroxyl compounds to afford carbonate dimers of MMB (6; X=O) (Scheme 1). All the reactions were carried out at ambient temperature and compounds were purified by column chromatography (silica gel; methanol/dichloromethane) to afford pure compounds (Table 5, lines 1-11) in 50-72% yield. The synthesized compounds were fully characterized by $^{1}$11 NMR, $^{13}$C NMR and high-resolution mass spectral analysis.

Scheme 1: Synthesis of carbamate and carbonate dimers of melampomagnolide B

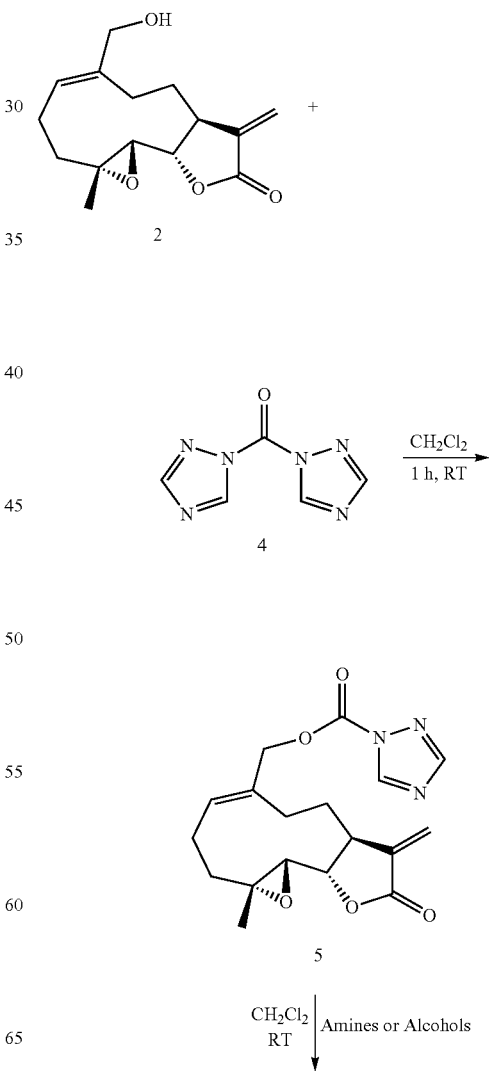

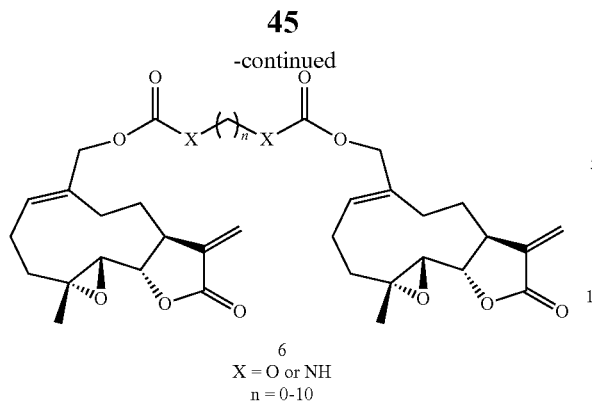

6
X = O or NH
n = 0-10

Example 2

Succinate Dimers of Melampomagnolide B

A series of succinate dimers of MMB (2) were prepared by reaction of MMB succinate (7) with various terminal alkyl diamines in the presence of EDC, HOBt and triethylamine (Scheme 2). All these reactions were carried out at ambient temperature in dichloromethane as a solvent. The compounds were purified by column chromatography (silica gel; methanol/dichloromethane) to afford pure compounds (Table 5, lines 12-19) of general structure 8 in 7075% yield. The synthesized compounds were fully characterized by $^1$H NMR, $^{13}$C NMR and high resolution mass spectral analysis.

Example 3

Ester Dimers of Melampomagnolide B

Ester dimers of MMB were prepared (Table 5, lines 20-21) by reaction of MMB (2) with various terminal alkyl carbonyl chlorides (9) in the presence triethylamine (Scheme 3).

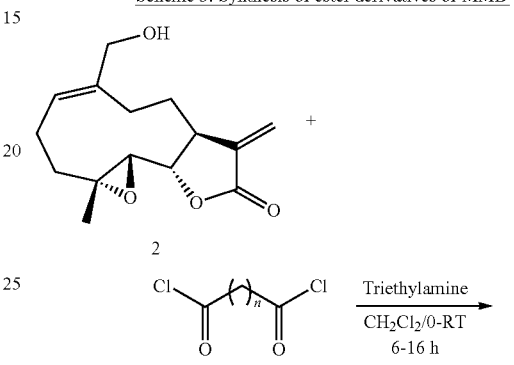

Scheme 3. Synthesis of ester derivatives of MMB

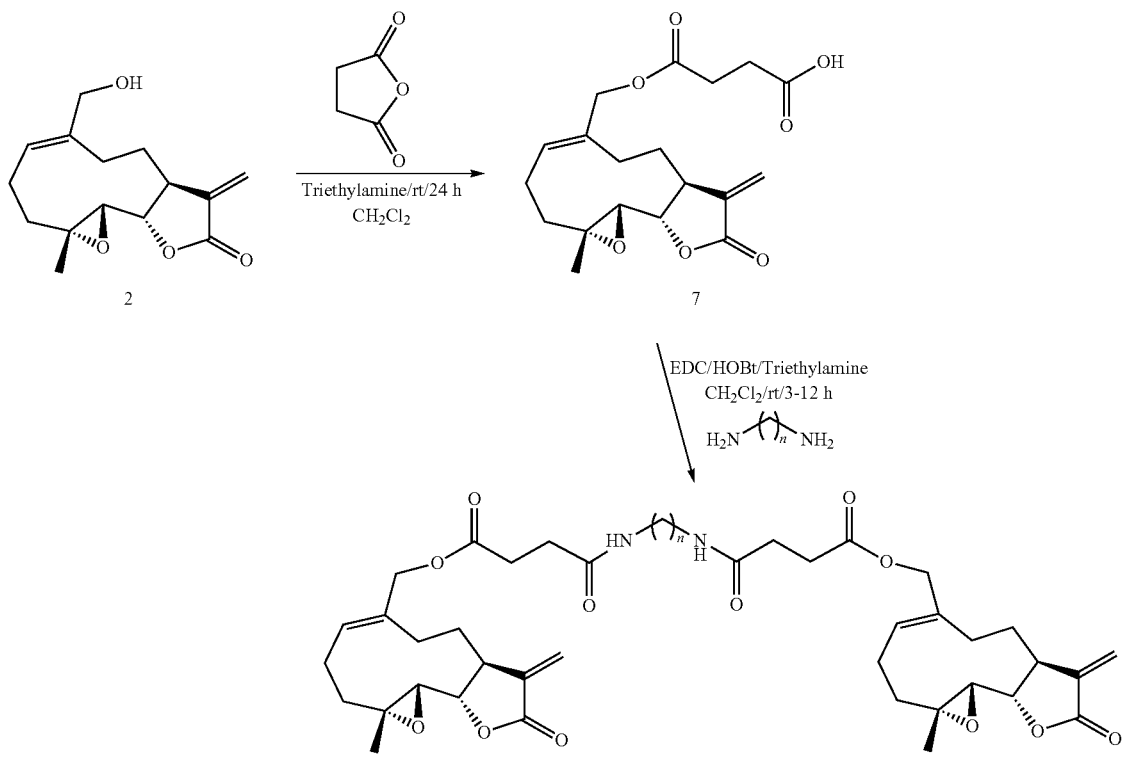

Scheme 2: Synthesis of succinic amide dimers of melampomagnolide B 8
n = 1-10

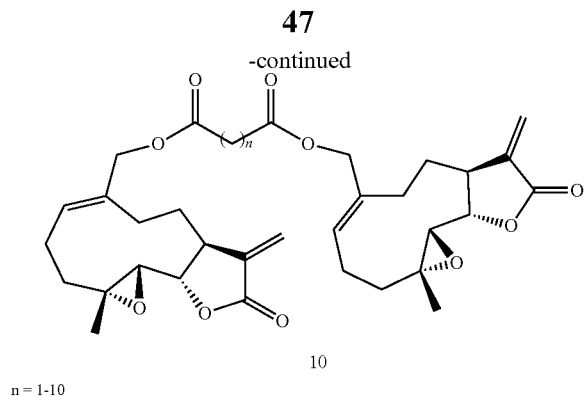

n = 1-10

Example 4

Carboxylic Amide Dimers of Melampomagnolic Acid

Carboxylic amide dimers of melampomagnolic acid were prepared via melampomagnolic acid (3) and alkyl terminal diamines. To obtain compound 3, the parthenolide C10 methyl group was oxidized via treatment with selenium dioxide (Scheme 4). Compound 3 was reacted with terminal alkyl diamines in presence of EDC/HOBt and triethylamine to obtain a variety of amide dimers (Scheme 5). All these reactions were carried out at ambient temperature and compounds were purified by column chromatography (silica gel; methanol/dichloromethane) to afford pure compounds (Table 5, lines 22-27) in 40-50% yield. The synthesized compounds were fully characterized by $^1$H NMR, $^{13}$C NMR and high-resolution mass spectral analysis.

Scheme 4: Oxidation of the C10 methyl group of parthenolide

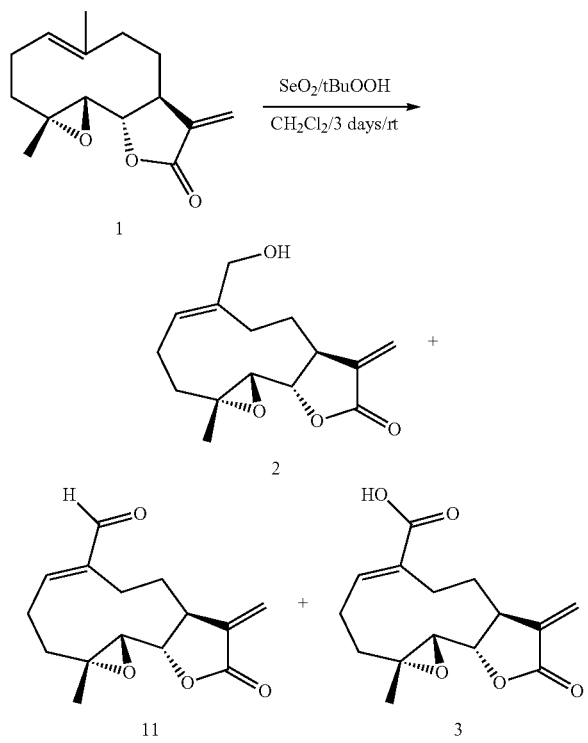

Scheme 5: Synthesis of carboxamide dimers of MMB

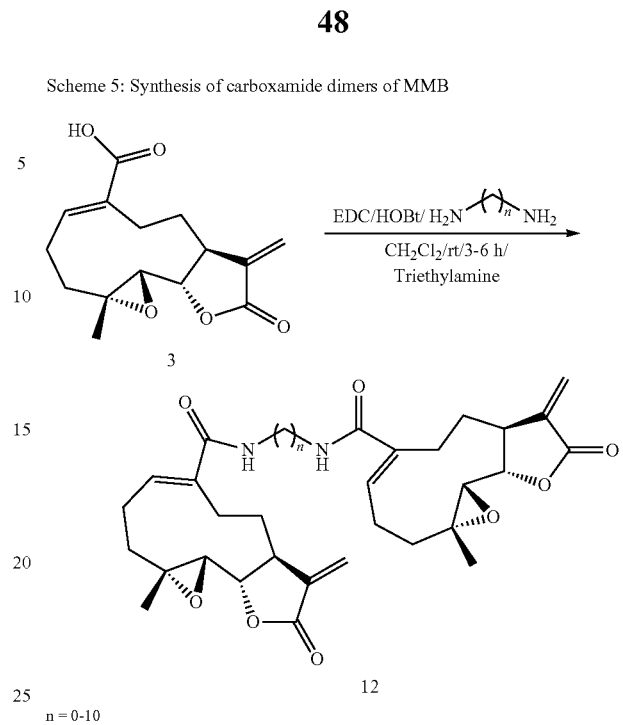

n = 0-10

Example 5

Biological Activity of MMB Dimers

Figure 2:
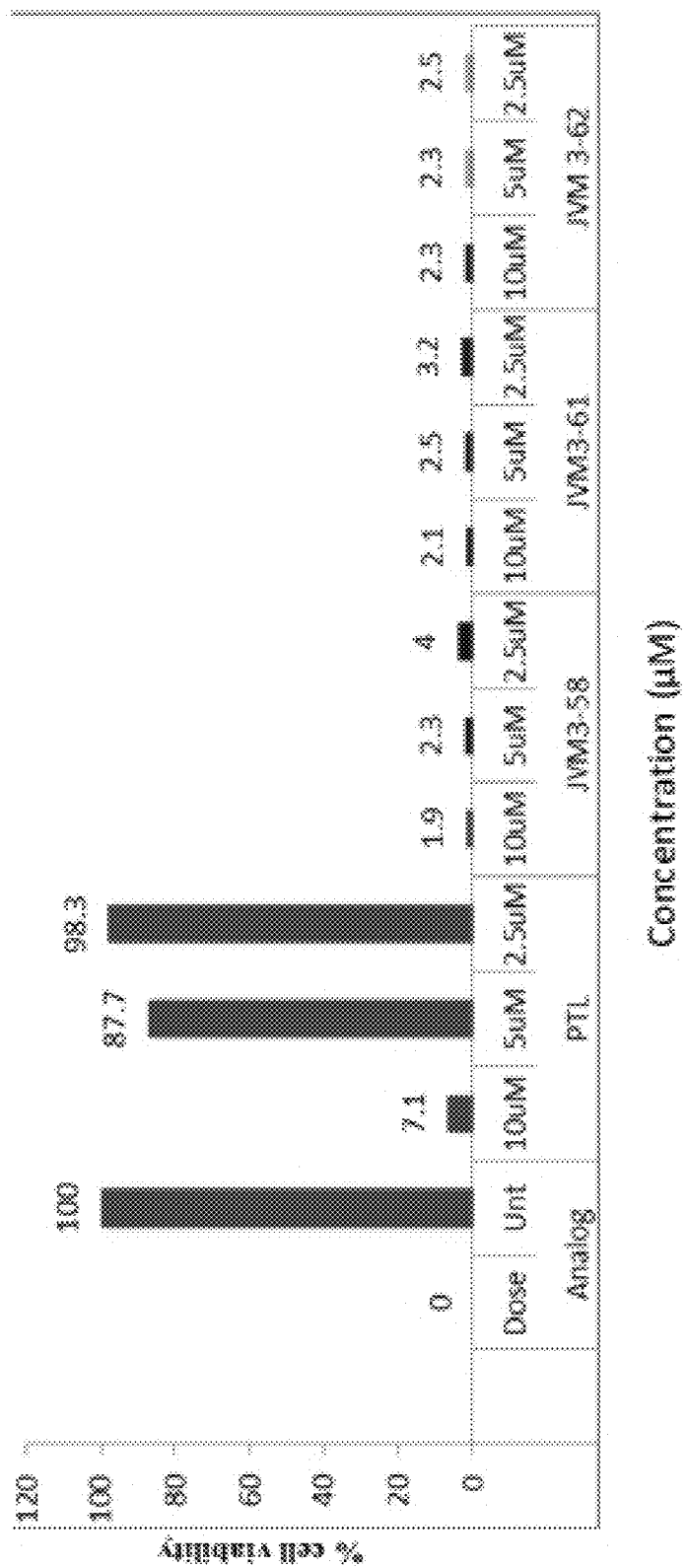
FIG. 2 depicts a graph showing activity of MMB carbamate dimers against M9 cell lines.
Figure 3:
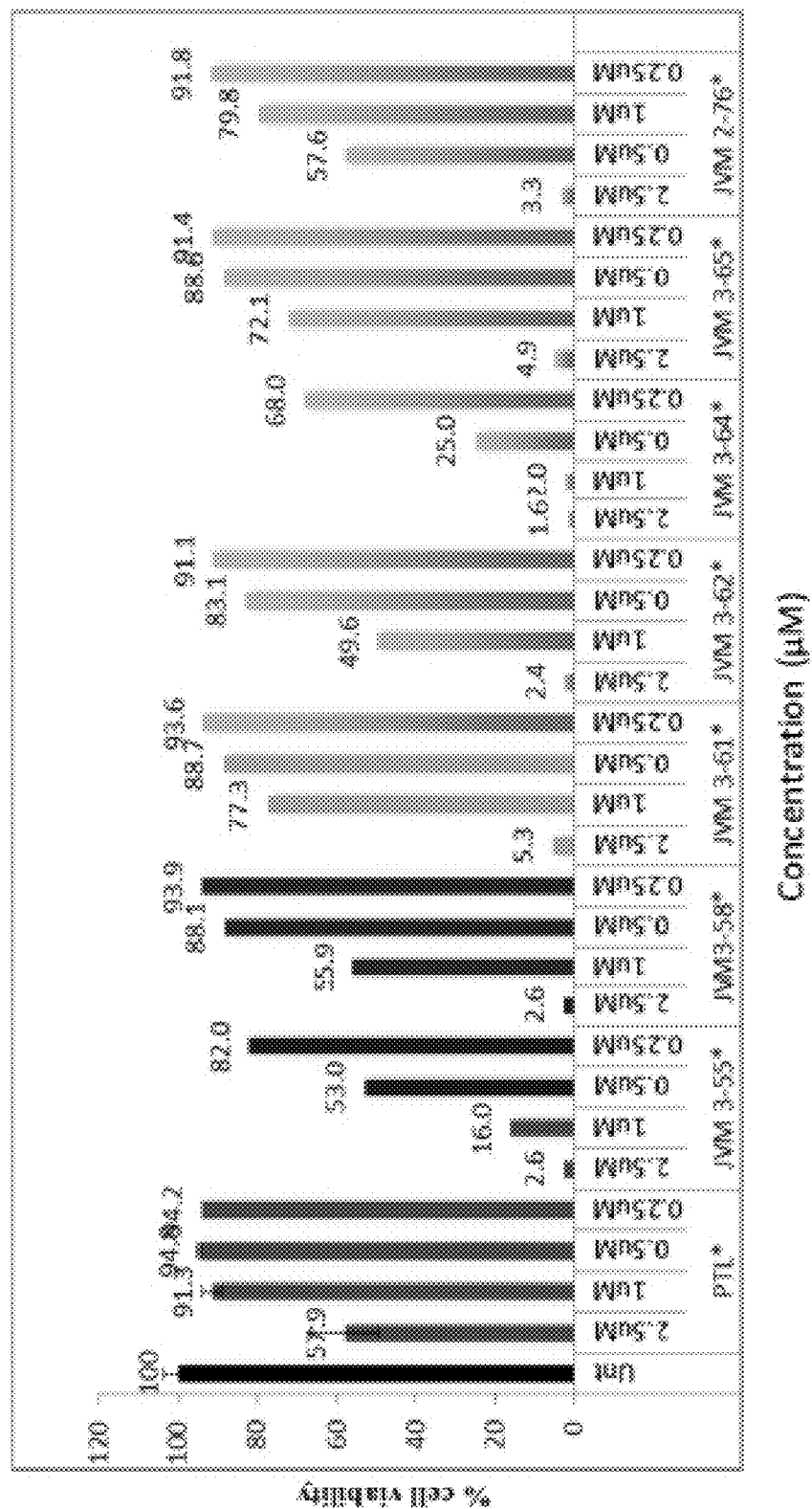
FIG. 3 depicts a graph showing activity of MMB carbamate dimers against M9 cell lines in lower doses.
Figure 4:
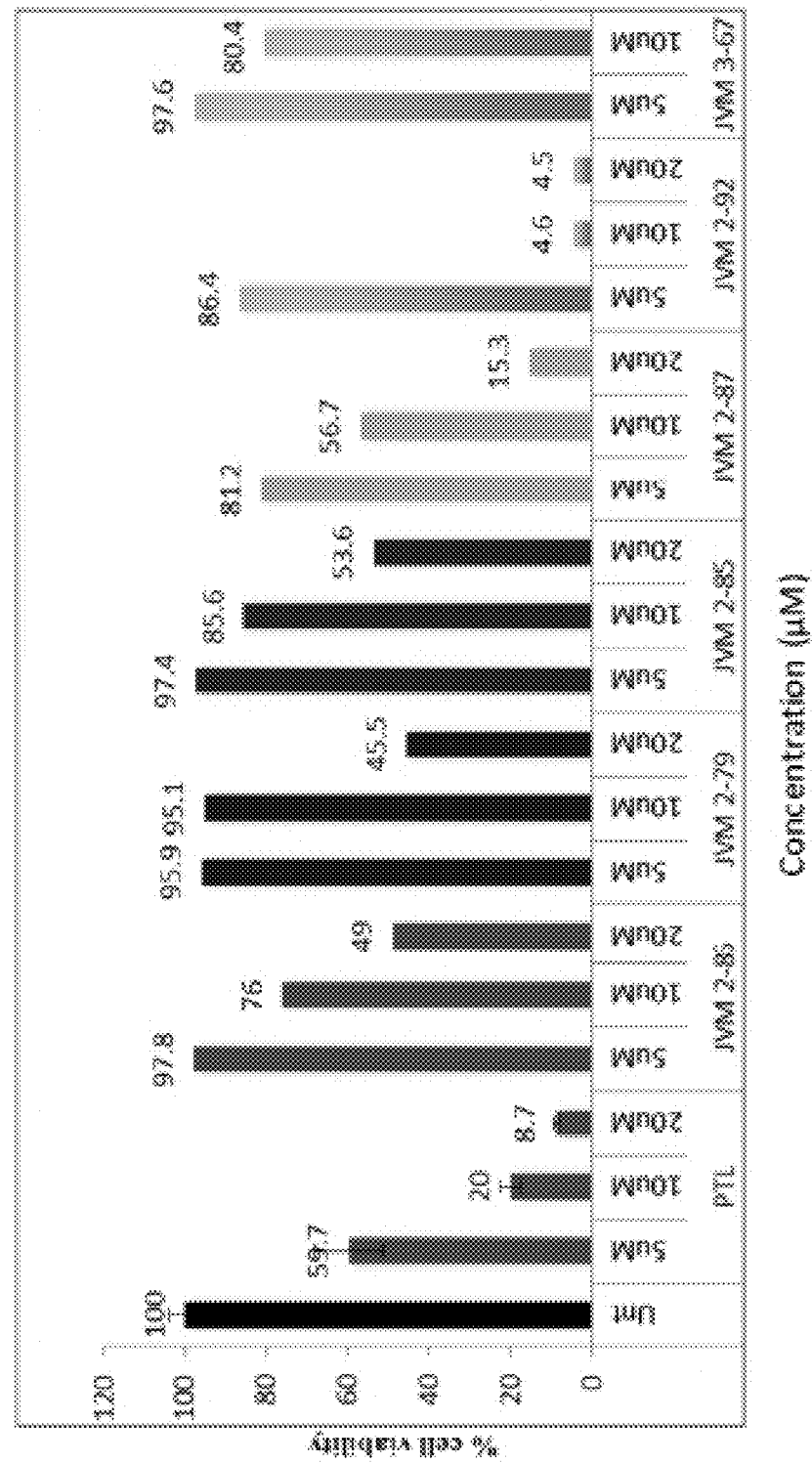
FIG. 4 depicts a graph showing activity of MMB succinic amide dimers against M9 cell lines.
Figure 5:
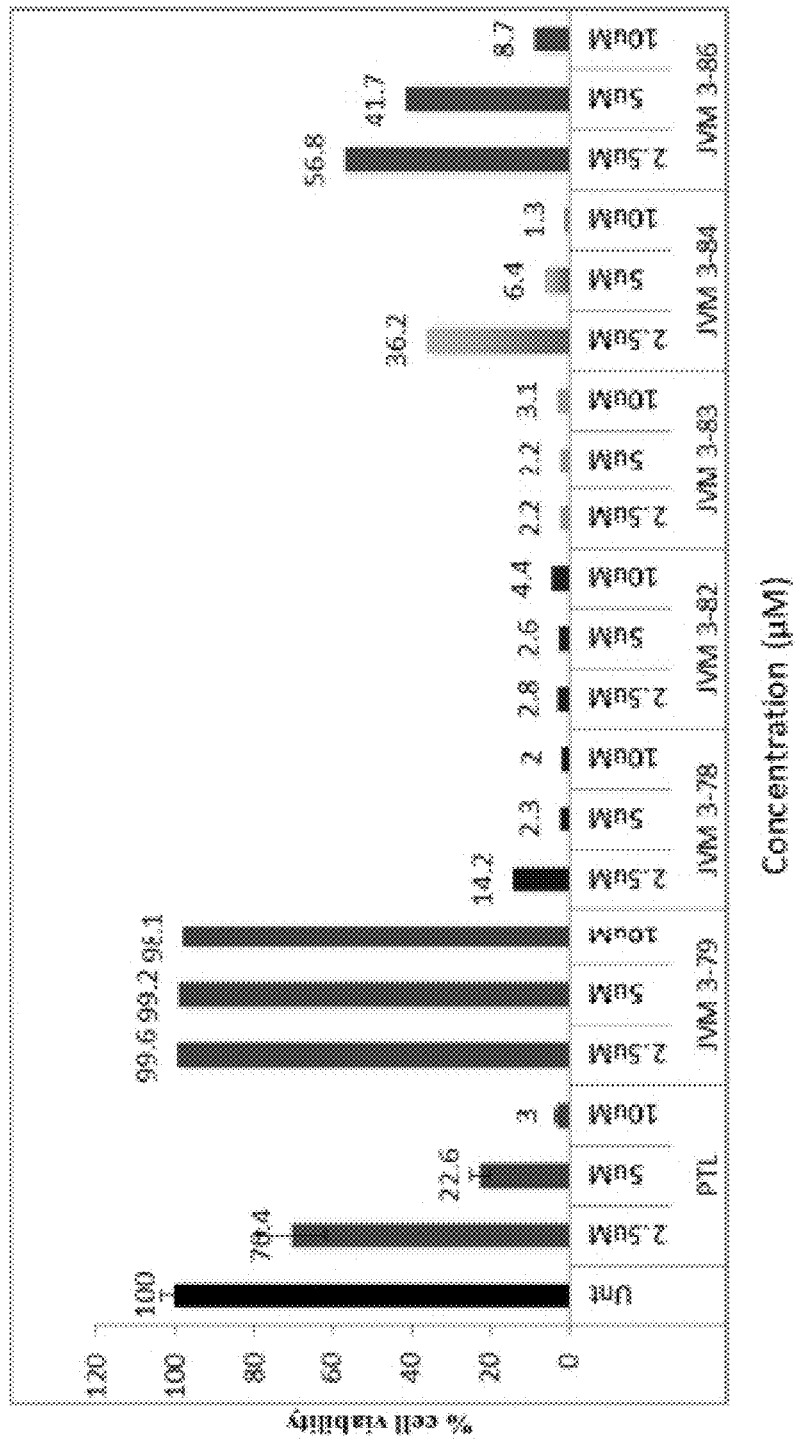
FIG. 5 depicts a graph showing activity of amide dimers of melampomagnolic acid against M9 cell lines.

The newly synthesized carbamate dimers of melampomagnalide were screened for anti-leukemic activity against M9ENL AML cell lines. For each compound, in vitro cell culture studies were performed in which a range of concentrations (0.25-20 µM) was tested for cytotoxicity against leukemia cell lines, primary leukemia specimens and normal bone marrow controls. Evaluations were performed generally after 24 hours of drug exposure using viability labeling with trypan blue dye, as well as flow cytometric labeling with Annexin V and propidium iodide to delineate dead cell populations. For all studies, native parthenolide (PTL) was included as a reference control. As expected, relative cytotoxicity varied considerably as a function of the specific modifications made to each molecule. These compounds consistently demonstrated approximately 10-fold greater cytotoxicity than PTL (FIG. 1, FIG. 2, FIG. 3). Remarkably, these agents had little effect on glutathione levels, in striking contrast to all previously synthesized compounds that showed biological activity. $LC_{50}$ values of these compounds are 0.34 µM (JVM 3-64), 0.56 µM (JVM 3-55), 1 µM (JVM 3-62), 1.2 µM (JVM 3-58), 1.35 µM (JVM 2-76), 1.6 µM (JVM 3-65) and 1.8 µM (JVM 3-61) against M9ENL AML cell lines. Another compound JVM 2-92 also showed promising result when compared to parthenolide at 10 µM against M9ENL cell line (FIG. 4). Moreover, compounds JVM 3-78, JVM 3-82, JVM 3-83 and JVM 3-84 showed more potency than parthenolide and MMB against M9 ENL cell lines (FIG. 5).

Figure 6:
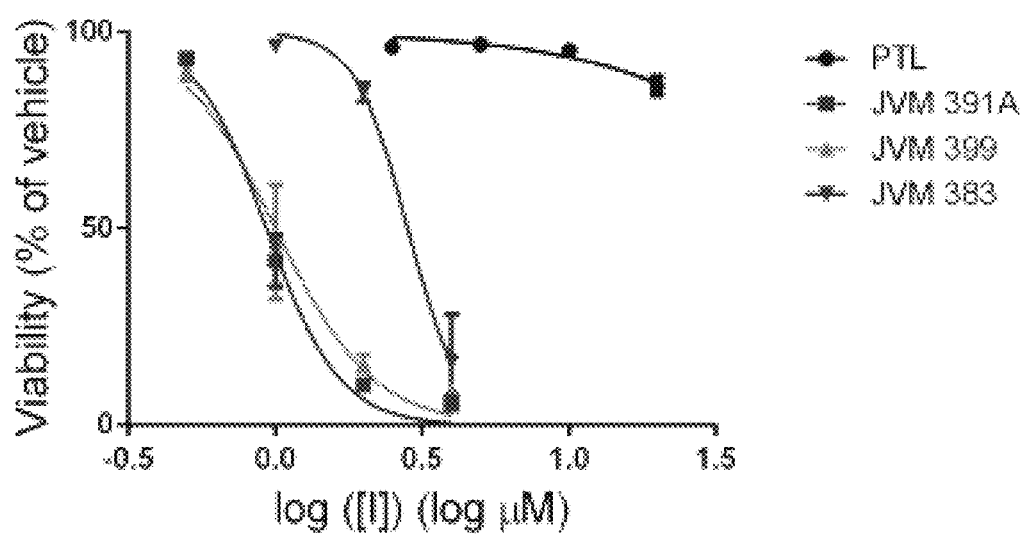
FIG. 6 depicts a graph showing activity of a few dimers of melampomagnolic acid against AML 1230009 cell lines.
Figure 7:
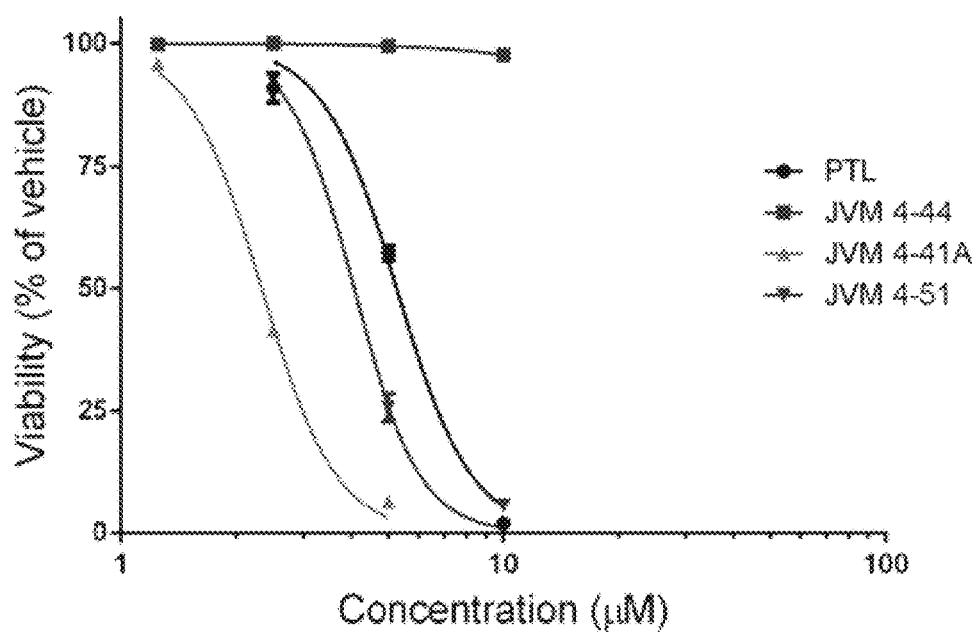
FIG. 7 depicts a graph showing activity of MMP dimers JVM 391A, JVM 399 and JVM 383 against AML cell lines.

When tested for activity against AML cell line AML 123009, JVM 3-91A, JVM 3-99 and JVM 3-83 showed enhanced cytotoxicity relative to PTL (FIG. 6).

TABLE 1

Activity against AML cell line

| | 123009 Viability | |
|---|---|---|
| | EC50 | ± |
| PTL | 100 | — |
| JVM 399 | 1.0 | 0.1 |
| JVM 391A | 0.93 | 0.07 |
| JVM 383 | 2.8 | 0.4 |

Example 6

In Vitro Growth Inhibition and Cytotoxicity

The above dimers of MMB were evaluated for growth inhibition properties against a panel of 60 human cancer cell lines derived from nine human cancer cell types, grouped into disease sub-panels that represent leukemia, lung, colon, central nervous system (CNS), melanoma, renal, ovary, breast, and prostate cancer cells. Growth inhibitory ($GI_{50}$) effects were measured as a function of the variation of optical density as a percentage of control. Initial screening assays were carried out at a single concentration of 10 μM. The compounds were first screened at a single concentration of $10^{-5}$ M. Compounds which showed more than 60% growth inhibition in at least eight cell lines from the panel of sixty cell lines were selected for a complete dose response study with five different concentrations of $10^{-4}$ M, $10^{-5}$ M, $10^{-6}$ M, $10^{-7}$ M and $10^{-8}$ M. Among all these compounds 5 compounds were selected for five-dose testing and the results obtained for 3 compounds, which are given in Table 2. Compound JVM 2-76 exhibited nano-molar range growth inhibition ($GI_{50}$) against the leukemia cell line subpanel: CCRF-CEM, HL-60 (TB), K-562, RPMI-8226, SR; non-small cell lung cancer cell line subpanel: NCI-H522; colon cancer cell line subpanel: COLO 205, HCT-116, HT29, SW-620; melanoma cancer cell line panel: LOX IMVI; ovarian cancer cell line subpanel: OVCAR-3; renal cancer cell line panel: RXF 393; and breast cancer cell line panel: MCF7 (Table 2). JVM 2-76 also exhibited low micromolar range $GI_{50}$ values against the remaining human cancer cell lines. JVM 2-92 showed promising results against all hematological leukemia cell lines in the nanomolar range (Table 2). This compound also exhibited nano-molar range growth inhibition against solid tumor cell lines NCI-H522 (non-small cell lung cancer cell line); SW-620 (colon cancer cell line); LOX IMVI (melanoma cell line); MCF7, BT-549 and MDA-MB-468 (breast cancer cell lines). Compound JVM 2-87 exhibited nanomolar range growth inhibition ($GI_{50}$) against leukemia cell lines: CCRF-CEM, HL-60 (TB), K-562 and SR; this compound also exhibited nanomolar range growth inhibition ($GI_{50}$) against solid tumor cell lines NCI-H522 (non-small cell lung cancer cell line); RXF 393 (renal cancer); and MCF7 (breast cancer cell line) and showed low micromolar range growth inhibition ($GI_{50}$) against other human tumor cell lines in the panel.

TABLE 2

Growth inhibition activity ($GI_{50}$), total growth inhibition activity (TGI), cytotoxicity ($LC_{50}$) of the potent compounds.

| | JVM 2-76 | | | JVM 2-87 | | | JVM 2-92 | | |
|---|---|---|---|---|---|---|---|---|---|
| Panel/cell line | $GI_{50}{}^a$ (μM) | $TGI^b$ (μM) | $LC_{50}{}^c$ (μM) | $GI_{50}{}^a$ (μM) | $TGI^b$ (μM) | $LC_{50}{}^c$ (μM) | $GI_{50}{}^a$ (μM) | $TGI^b$ (μM) | $LC_{50}{}^c$ (μM) |
| Leukemia | | | | | | | | | |
| CCRF-CEM | 0.28 | 0.96 | >100 | 0.32 | 1.48 | >100 | 0.28 | 1.00 | >100 |
| HL-60(TB) | 0.31 | 1.71 | >100 | 0.63 | 3.12 | >100 | 0.44 | 2.13 | >100 |
| K-562 | 0.56 | 16.1 | >100 | 0.97 | 12.9 | >100 | 0.45 | 3.21 | >100 |
| MOLT-4 | 1.48 | 9.29 | >100 | 2.11 | 6.41 | >100 | 0.64 | 4.20 | >100 |
| RPMI-8226 | 0.78 | 4.16 | >100 | 1.67 | 5.70 | >100 | 0.50 | 3.33 | >100 |
| SR | 0.38 | 2.30 | >100 | 0.41 | 2.10 | >100 | 0.33 | 1.17 | >100 |
| Non-Small Cell Lung Cancer | | | | | | | | | |
| A549/ATCC | 14.9 | 32.7 | 71.7 | 18.5 | 40.7 | 89.4 | 13.8 | 33.7 | 82.6 |
| HOP-92 | 1.30 | 3.35 | 8.61 | 1.58 | 3.27 | 6.77 | 1.40 | 3.05 | 6.64 |
| NCI-H226 | 2.56 | 8.18 | 30.9 | 2.06 | 4.95 | 15.7 | 1.90 | 4.05 | 8.60 |
| NCI-H23 | 2.66 | 7.71 | 45.5 | 2.99 | 8.25 | 42.6 | 2.23 | 5.13 | 18.5 |
| NCI-H322M | 16.4 | 41.6 | >100 | 16.3 | 31.4 | 60.5 | 16.3 | 31.6 | 61.3 |
| NCI-H460 | 4.34 | 16.2 | 50.7 | 5.0 | 19.9 | 66.2 | 2.18 | 5.17 | 25.7 |
| NCI-H522 | 0.22 | 0.44 | 0.88 | 0.48 | 1.80 | 6.36 | 0.42 | 1.64 | 5.63 |
| Colon Cancer | | | | | | | | | |
| COLO 205 | 0.52 | 2.33 | 7.97 | 1.35 | 3.14 | 7.28 | 1.22 | 3.16 | 8.15 |
| HCC-2998 | 6.71 | 20.7 | 53.9 | 4.12 | 16.7 | 63.6 | 2.25 | 4.70 | 9.82 |
| HCT-116 | 0.54 | 1.86 | 4.56 | 1.54 | 2.88 | 5.41 | 0.86 | 2.18 | 4.97 |
| HCT-15 | 6.18 | 20.7 | 49.8 | 3.60 | 15.6 | 43.2 | 2.63 | 11.9 | 46.0 |
| HT29 | 0.51 | 1.78 | 4.85 | 1.64 | 3.12 | 5.92 | 1.33 | 2.75 | 5.69 |
| KM12 | 6.53 | 21.0 | 54.2 | 9.46 | 22.9 | 53.4 | 4.60 | 17.1 | 50.2 |
| SW-620 | 0.43 | 1.75 | 5.14 | 1.22 | 2.97 | 7.20 | 0.54 | 2.07 | 6.14 |
| CNS Cancer | | | | | | | | | |
| SF-268 | 3.08 | 12.0 | 42.3 | 3.34 | 11.6 | 42.4 | 2.92 | 10.1 | 42.4 |
| SF-295 | 11.1 | 26.9 | 65.2 | 15.1 | 29.3 | 56.8 | 7.68 | 21.9 | 52.0 |
| SF-539 | 1.92 | 4.56 | 12.7 | 2.43 | 5.76 | 20.9 | 1.85 | 4.29 | 9.95 |
| SNB-19 | 3.97 | 19.0 | 92.5 | 4.15 | 19.9 | >100 | 3.38 | 16.3 | >100 |
| SNB-75 | 2.20 | 11.4 | 33.8 | 2.02 | 7.25 | 26.9 | 1.47 | 4.35 | 15.6 |
| U251 | 3.51 | 13.7 | 51.5 | 3.03 | 10.6 | 43.0 | 3.01 | 9.25 | 44.7 |

TABLE 2-continued

Growth inhibition activity (GI$_{50}$), total growth inhibition activity (TGI), cytotoxicity (LC$_{50}$) of the potent compounds.

| Panel/cell line | JVM 2-76 | | | JVM 2-87 | | | JVM 2-92 | | |
|---|---|---|---|---|---|---|---|---|---|
| | GI$_{50}$[a] (μM) | TGI[b] (μM) | LC$_{50}$[c] (μM) | GI$_{50}$[a] (μM) | TGI[b] (μM) | LC$_{50}$[c] (μM) | GI$_{50}$[a] (μM) | TGI[b] (μM) | LC$_{50}$[c] (μM) |
| Melanoma | | | | | | | | | |
| LOX IMVI | 0.46 | 1.85 | 5.82 | 1.37 | 2.76 | 5.56 | 0.37 | 1.36 | 4.06 |
| MALME-3M | 2.06 | 5.24 | 27.3 | 2.04 | 4.04 | 8.00 | 1.94 | 4.17 | 8.93 |
| M14 | 1.71 | 3.74 | 8.20 | 1.79 | 3.79 | 8.02 | 1.65 | 3.64 | 8.05 |
| MDA-MB-435 | 1.51 | 3.32 | 7.30 | 1.80 | 3.69 | 7.58 | 1.63 | 3.44 | 7.25 |
| SK-MEL-2 | 2.01 | 3.96 | 7.81 | 2.25 | 4.59 | 9.38 | 2.12 | 4.15 | 8.13 |
| SK-MEL-28 | 1.58 | 4.13 | 12.6 | 1.65 | 3.23 | 6.32 | 1.47 | 3.03 | 6.22 |
| SK-MEL-5 | 3.19 | 12.2 | 37.0 | 3.13 | 11.1 | 38.4 | 1.88 | 4.19 | 9.37 |
| UACC-257 | 2.07 | 7.46 | 42.4 | 1.76 | 4.48 | 16.0 | 2.06 | 5.59 | 32.0 |
| UACC-62 | 1.41 | 3.16 | 7.04 | 1.97 | 4.20 | 8.94 | 1.69 | 3.78 | 8.44 |
| Ovarian Cancer | | | | | | | | | |
| OVCAR-3 | 0.76 | 2.13 | 5.07 | 1.50 | 2.82 | 5.31 | 1.29 | 2.61 | 5.30 |
| OVCAR-4 | 2.72 | 15.2 | 41.9 | 1.64 | 3.92 | 9.38 | 1.48 | 3.46 | 8.06 |
| OVCAR-5 | 1.67 | 3.53 | 7.47 | 1.82 | 3.64 | 7.31 | 1.70 | 3.47 | 7.06 |
| OVCAR-8 | 3.27 | 13.7 | 61.0 | 2.90 | 13.3 | >100 | 3.24 | 16.5 | >100 |
| NCI/ADR-RES | 70.0 | >100 | >100 | 33.5 | >100 | >100 | 26.7 | >100 | >100 |
| SK-OV-3 | 5.99 | 19.7 | 49.9 | 6.45 | 19.7 | 47.9 | 5.80 | 19.2 | 49.1 |
| Renal Cancer | | | | | | | | | |
| 786-0 | 1.57 | 3.17 | 6.39 | 1.62 | 3.29 | 6.67 | 1.49 | 3.00 | 6.04 |
| A498 | 6.24 | 19.4 | 47.5 | 6.72 | 20.8 | 49.6 | 2.72 | 8.30 | 31.3 |
| ACHN | 3.05 | 9.84 | 35.4 | 3.13 | 10.9 | 34.7 | 2.10 | 5.16 | 17.2 |
| CAKI-1 | 16.1 | 33.1 | 68.1 | 12.7 | 32.0 | 80.3 | 10.5 | 22.8 | 49.9 |
| RXF 393 | 0.85 | 2.43 | 6.35 | 0.85 | 2.61 | 7.27 | 1.01 | 2.50 | 6.21 |
| SN12C | 2.49 | 10.7 | 45.5 | 3.74 | 14.8 | 53.8 | 2.69 | 10.3 | 49.7 |
| TK-10 | 1.82 | 4.40 | 11.8 | 20.8 | 3.94 | 7.46 | 1.78 | 3.28 | 6.02 |
| UO-31 | 8.90 | 22.5 | 52.3 | 10.9 | 24.2 | 54.0 | 3.90 | 16.1 | 45.6 |
| Prostate Cancer | | | | | | | | | |
| PC-3 | 3.79 | 15.6 | 49.4 | 3.64 | 13.7 | 40.7 | 2.53 | 7.31 | 29.6 |
| DU-145 | 3.06 | 9.55 | 32.6 | 1.92 | 3.61 | 6.81 | 1.75 | 3.18 | 5.78 |
| Breast Cancer | | | | | | | | | |
| MCF7 | 0.39 | 1.93 | 6.20 | 0.77 | 2.47 | — | 0.42 | 1.85 | — |
| MDA-MB-231/ATCC | 1.47 | 3.07 | 6.40 | 1.97 | 4.41 | 9.88 | 1.58 | 4.05 | 13.3 |
| HS 578T | 2.91 | 13.0 | >100 | 3.88 | 29.5 | >100 | 2.99 | 24.9 | >100 |
| BT-549 | 1.00 | 2.23 | 4.96 | 1.23 | 2.51 | 5.12 | 0.66 | 2.03 | 4.65 |
| T-47D | 1.60 | 5.73 | >100 | 1.51 | 3.86 | — | 1.49 | 4.48 | >100 |
| MDA-MB-468 | 1.06 | 3.96 | 24.7 | 1.33 | 3.84 | 21.3 | 0.98 | 2.64 | 7.04 |

[a]GI$_{50}$: 50% Growth inhibition, concentration of drug resulting in a 50% reduction in net protein increase compared with control cells.
[b]TGI: 100% Growth inhibition, concentration of drug resulting in a 100% reduction in net protein increase compared with control cells.
[c]LC50, concentration of compound that halves cell population through cell death.

TABLE 3

NCI five dose result for JVM 3-62

| Panel/Cell | Time | | Mean Optical Densities | | | | | Percent Growth | | | | | GI50 | TGI | LC50 |
|---|---|---|---|---|---|---|---|---|---|---|---|---|---|---|---|
| | | | Log10 Concentration | | | | | | | | | | | | |
| | Zero | Ctrl | −8.0 | −7.0 | −6.0 | −5.0 | −4.0 | −8.0 | −7.0 | −6.0 | −5.0 | −4.0 | | | |
| Leukemia | | | | | | | | | | | | | | | |
| CCRF-CEM | 0.799 | 2.955 | 2.935 | 2.727 | 0.739 | 0.442 | 0.446 | 99 | 89 | −8 | −45 | −44 | 2.55E−7 | 8.37E−7 | >1.00E−4 |
| HL-60(TB) | 0.823 | 2.731 | 2.783 | 2.574 | 0.774 | 0.519 | 0.502 | 103 | 92 | −6 | −37 | −39 | 2.68E−7 | 8.69E−7 | >1.00E−4 |
| K-562 | 0.345 | 2.255 | 2.307 | 2.384 | 0.387 | 0.297 | 0.193 | 103 | 107 | 2 | −14 | −44 | 3.49E−7 | 1.37E−6 | >1.00E−4 |
| MOLT-4 | 1.048 | 3.078 | 3.083 | 3.108 | 1.092 | 0.764 | 0.697 | 100 | 101 | 2 | −27 | −34 | 3.30E−7 | 1.18E−6 | >1.00E−4 |

TABLE 3-continued

NCI five dose result for JVM 3-62

| | Time | | Log10 Concentration | | | | | | | | | | | | | |
| | | | Mean Optical Densities | | | | | Percent Growth | | | | | | | |
| Panel/Cell | Zero | Ctrl | -8.0 | -7.0 | -6.0 | -5.0 | -4.0 | -8.0 | -7.0 | -6.0 | -5.0 | -4.0 | GI50 | TGI | LC50 |
|---|---|---|---|---|---|---|---|---|---|---|---|---|---|---|---|
| RPMI-8226 | 1.002 | 2.831 | 2.798 | 2.686 | 0.867 | 0.548 | 0.621 | 98 | 92 | -13 | -45 | -38 | 2.50E-7 | 7.45E-7 | >1.00E-4 |
| SR | 0.542 | 2.545 | 2.510 | 2.437 | 0.656 | 0.401 | 0.373 | 98 | 95 | 6 | -26 | -31 | 3.17E-7 | 1.51E- | >1.00E-4 |
| Non-Small Cell Lung Cancer | | | | | | | | | | | | | | | |
| A549/ATCC | 0.345 | 1.940 | 1.883 | 1.882 | 1.726 | 0.097 | 0.055 | 96 | 96 | 87 | -72 | -84 | 1.70E-6 | 3.51E-6 | 7.26E-6 |
| EKVX | 0.650 | 1.557 | 1.474 | 1.469 | 1.214 | 0.010 | 0.010 | 91 | 90 | 62 | -99 | -98 | 1.19E-6 | 2.44E-6 | 4.99E-6 |
| HOP-62 | 0.541 | 1.467 | 1.495 | 1.491 | 1.245 | 0.195 | 0.111 | 103 | 103 | 76 | -64 | -80 | 1.53E-6 | 3.49E-6 | 7.95E-6 |
| HOP-92 | 1.506 | 1.887 | 1.837 | 1.792 | 1.111 | 0.116 | 0.185 | 87 | 75 | -26 | -92 | -88 | 1.77E-7 | 5.51E-7 | 2.29E-6 |
| NCI-H226 | 0.734 | 1.609 | 1.547 | 1.514 | 1.464 | 0.393 | 0.313 | 93 | 89 | 83 | -46 | -57 | 1.81E-6 | 4.39E-6 | 2.11E-6 |
| NCI-H23 | 0.556 | 1.905 | 1.912 | 1.904 | 0.922 | 0.083 | 0.122 | 100 | 100 | 27 | -85 | -78 | 4.85E-7 | 1.74E-6 | 4.86E-6 |
| NCI-H322M | 0.704 | 1.741 | 1.817 | 1.780 | 1.740 | 0.344 | 0.065 | 107 | 104 | 100 | -51 | -91 | 2.14E-6 | 4.59E-6 | 0.83E-6 |
| NCI-H460 | 0.292 | 2.846 | 2.943 | 2.908 | 2.447 | 0.128 | 0.105 | 104 | 102 | 84 | -56 | -64 | 1.75E-6 | 3.98E-6 | 9.02E-6 |
| NCI-H522 | 0.659 | 1.962 | 1.776 | 1.823 | 0.282 | 0.165 | 0.222 | 86 | 89 | -57 | -75 | -66 | 1.86E-7 | 4.07E-7 | 8.93E-7 |
| Colon Cancer | | | | | | | | | | | | | | | |
| COLO 205 | 0 475 | 1.636 | 1.685 | 1.745 | 0.403 | 0.128 | 0.165 | 104 | 109 | -15 | -73 | -65 | 3.00E-7 | 7.56E-7 | 3.99E-6 |
| HCC-2998 | 0.491 | 1.863 | 1.866 | 1.833 | 1.350 | 0.034 | 0.040 | 100 | 98 | 63 | -93 | -92 | 1.20E-6 | 2.52E-6 | 5.28E-6 |
| HCT-116 | 0.344 | 2.563 | 2.525 | 2.501 | 0.130 | 0.027 | 0.047 | 98 | 97 | -62 | -92 | -86 | 1.95E-7 | 4.07E-7 | 8.37E-7 |
| HCT-15 | 0.253 | 1.814 | 1.674 | 1.655 | 0.503 | 0.025 | 0.042 | 91 | 90 | 16 | -90 | 83 | 3.46E-7 | 1.41E-6 | 4.16E-6 |
| HT29 | 0.171 | 1.187 | 1.189 | 1.152 | 0.114 | 0.034 | 0.028 | 100 | 97 | -33 | -80 | -84 | 2.28E-7 | 5.54E-7 | 2.27E-6 |
| KM12 | 0.478 | 2.570 | 2.605 | 2.673 | 1.830 | 0.161 | 0.082 | 102 | 105 | 65 | -66 | -83 | 1.29E-6 | 3.11E-6 | 7.49E-6 |
| SW-620 | 0.330 | 2.596 | 2.557 | 2.400 | 0.271 | 0.070 | 0.078 | 91 | 91 | -18 | -79 | -77 | 2.39E-7 | 6.86E-7 | 3.37E-6 |
| CNS Cancer | | | | | | | | | | | | | | | |
| SF-268 | 0.636 | 2.008 | 2.027 | 2.058 | 1.322 | 0.215 | 0.260 | 101 | 104 | 50 | -66 | -59 | 9.99E-7 | 2.69E-6 | 7.24E-6 |
| SF-295 | 1.081 | 3.077 | 2.784 | 2.908 | 2.820 | 0.645 | 0.145 | 85 | 92 | 87 | -40 | -87 | 1.95E-6 | 4.82E-6 | 1.62E-5 |
| SF-539 | 0.862 | 2.778 | 2.576 | 2.692 | 0.626 | 0.074 | 0.145 | 89 | 95 | -27 | -91 | -83 | 2.35E-7 | 5.99E-7 | 2.26E-6 |
| SNB-75 | 1.311 | 2.103 | 1.883 | 1.925 | 1.792 | 0.645 | | 72 | 78 | 61 | -51 | -100 | 1.25E-6 | 3.50E-7 | 9.84E-6 |
| U251 | 0.351 | 1.858 | 1.802 | 1.738 | 0.906 | 0.051 | 0.042 | 96 | 91 | -18 | -79 | -77 | 5.78E-7 | 2.00E-6 | 5.13E-6 |
| Melanoma | | | | | | | | | | | | | | | |
| LOX IMVI | 0.231 | 1.750 | 1.727 | 1.594 | 0.072 | 0.022 | 0.044 | 98 | 90 | -69 | -90 | -81 | 1.78E-7 | 3.68E-7 | 7.61E-7 |
| MAL1ME-3M | 0.616 | 1.340 | 1.307 | 1.302 | 0.279 | 0.261 | 0.213 | 95 | 95 | -55 | -58 | -65 | 1.99E-7 | 4.30E-7 | 9.29E-7 |
| M14 | 0.484 | 1.809 | 1.739 | 1.760 | 0.434 | 0.142 | 0.117 | 95 | 95 | -10 | -71 | -76 | 2.72E-7 | 8.00E-7 | 4.53E-6 |
| MDA-MB-435 | 0.494 | 2.467 | 2.291 | 2.312 | 0.405 | 0.129 | 0.070 | 91 | 92 | -18 | -74 | -86 | 2.41E-7 | 6.86E-7 | 3.74E-6 |
| SK-MEL-2 | 0.784 | 2.367 | 2.234 | 2.362 | 1.3520 | 0.435 | 0.248 | 92 | 100 | 36 | -45 | -68 | 6.01E-7 | 2.79E-6 | 1.70E-6 |
| SK-MEL-211 | 0.231 | 1.750 | 1.727 | 1.594 | 0.072 | 0.022 | 0.044 | 92 | 90 | -37 | -77 | -71 | 2.05E-7 | 5.11E-7 | 2.12E-6 |
| SK-MEL-6 | 0.616 | 1.340 | 1.307 | 1.302 | 0.279 | 0.261 | 0.213 | 99 | 95 | 63 | -89 | -87 | 1.21E-6 | 2.59E-6 | 5.53E-6 |
| UACC-257 | 0.484 | 1.809 | 1.739 | 1.760 | 0.434 | 0.142 | 0.117 | 97 | 89 | 47 | -57 | -55 | 8.48E-7 | 2.82E-6 | 8.51E-6 |
| UACC-62 | 0.494 | 2.467 | 2.291 | 2.312 | 0.405 | 0.129 | 0.070 | 96 | 87 | -39 | -84 | -77 | 1.97E-7 | 4.88E-7 | 1.72E-6 |
| Ovarian Cancer | | | | | | | | | | | | | | | |
| IGROV1 | 0.800 | 2.342 | 2.420 | 2.372 | 1.581 | 0.232 | 0.229 | 105 | 102 | 61 | -71 | -71 | 1.01E-6 | 2.61E-6 | 6.72E-6 |
| OVCAR-3 | 0.494 | 1.658 | 1.683 | 1.670 | 0.524 | 0.008 | -0.003 | 102 | 101 | 3 | -98 | -100 | 3.30E-7 | 1.08E-6 | 3.32E-6 |
| OVCAR-4 | 0.790 | 1.741 | 1.642 | 1.655 | 1.112 | 0.062 | 0.087 | 90 | 91 | 34 | -92 | -89 | 5.21E-7 | 1.86E-6 | 4.63E-6 |
| OVCAR-5 | 0.583 | 1.445 | 1.375 | 1.364 | 0.561 | 0.117 | 0.133 | 92 | 91 | -4 | -80 | -77 | 2.69E-7 | 9.12E-7 | 4.04E-6 |
| OVCAR-8 | 0.375 | 1.781 | 1.788 | 1.729 | 0.463 | 0.145 | 0.169 | 100 | 96 | 6 | -51 | -55 | 3.26E-7 | 1.24E-6 | 6.77E-6 |
| NCI/ADR- | 0.582 | 1.965 | 2.011 | 2.123 | 1.852 | 0.876 | 0.252 | 103 | 111 | 92 | 21 | -57 | 3.91E-6 | 1.87E-5 | 8.20E-5 |
| SK-OV-3 | 0.854 | 1.656 | 1.719 | 1.717 | 1.666 | 0.934 | -0.008 | 108 | 108 | 101 | 10 | -100 | 3.64E-6 | 1.23E-5 | 3.51E-6 |
| Renal Cancer | | | | | | | | | | | | | | | |
| 786-0 | 1.063 | 2.879 | 2.794 | 2.806 | 0.824 | 0.198 | 0.182 | 95 | 95 | -32 | -81 | -81 | 2.44E-7 | 6.46E-7 | 2.93E-6 |
| A498 | 1.728 | 2.763 | 2.701 | 2.799 | 2.682 | 0.113 | 0.116 | 94 | 104 | 91 | -91 | -83 | 1.69E-6 | 3.14E-6 | 5.83E-6 |
| ACHN | 0.338 | 1.651 | 1.621 | 1.657 | 0.264 | 0.055 | 0.078 | 98 | 100 | -31 | -84 | -78 | 2.68E-7 | 6.62E-7 | 2.85E-6 |
| CAKI-1 | 0.444 | 2.043 | 1.951 | 1.908 | 1.095 | 0.033 | 0.004 | 94 | 92 | 41 | -93 | -99 | 5.57E-7 | 2.02E-6 | 4.79E-6 |
| RXF 393 | 0.642 | 1.297 | 1.271 | 1.198 | 0.113 | 0.052 | 0.152 | 96 | 85 | -82 | -92 | -76 | 1.62E-7 | 3.22E-7 | 6.40E-7 |
| SN12C | 0.749 | 2.711 | 2.713 | 2.543 | 0.697 | 0.261 | 0.233 | 100 | 91 | -7 | -65 | -59 | 2.64E-7 | 8.49E-7 | 5.49E-6 |
| TK-10 | 0.628 | 1.961 | 1.870 | 1.927 | 0.584 | 0.010 | 0.006 | 92 | 97 | -7 | -98 | -99 | 2.84E-7 | 8.56E-7 | 2.95E-6 |
| UO-31 | 0.884 | 2.292 | 2.150 | 2.153 | 1.555 | 0.055 | 0.118 | 90 | 90 | 48 | -94 | -87 | 8.80E-7 | 2.17E-6 | 4.90E-6 |
| Prostate Cancer | | | | | | | | | | | | | | | |
| PC-3 | 0.594 | 1.856 | 1.757 | 1.748 | 0.040 | 0.152 | 0.065 | 91 | 91 | 21 | -78 | -91 | 3.85E-7 | 1.63E-6 | 5.20E-6 |
| DU-145 | 0.518 | 1.924 | 1.970 | 1.990 | 1.309 | 0.003 | -0.008 | 103 | 105 | 56 | -99 | -100 | 1.10E-6 | 2.30E-6 | 4.81E-6 |
| Breast Cancer | | | | | | | | | | | | | | | |
| MCF7 | 0.298 | 1.559 | 1.417 | 1.304 | 0.278 | 0.075 | 0.138 | 89 | 80 | -7 | -75 | -54 | 2.21E-7 | 8.33E-7 | 4.30E-6 |
| MDA-MB-231/ATCC | 0.566 | 1.441 | 1.430 | 1.369 | 0.299 | 0.127 | 0.114 | 99 | 92 | -47 | -78 | -80 | 2.00E-7 | 4.58E-7 | 1.24E-6 |
| HS578T | 1.079 | 2.072 | 2.010 | 1.975 | 1.616 | 1.025 | 0.794 | 94 | 90 | 54 | -5 | -26 | 1.17E-6 | 8.25E-6 | >1.00E-4 |
| BT-549 | 1.171 | 2.411 | 2.313 | 2.340 | 1.012 | 1.025 | 0.794 | 94 | 94 | -14 | -80 | -85 | 2.57E-7 | 7.48E-7 | 3.57E-6 |

TABLE 3-continued

NCI five dose result for JVM 3-62

| Panel/Cell | Time | | Mean Optical Densities | | | | | Percent Growth | | | | | GI50 | TGI | LC50 |
|---|---|---|---|---|---|---|---|---|---|---|---|---|---|---|---|
| | Zero | Ctrl | −8.0 | −7.0 | −6.0 | −5.0 | −4.0 | −8.0 | −7.0 | −6.0 | −5.0 | −4.0 | | | |
| T-47D | 0.552 | 1.116 | 1.152 | 1.151 | 0.529 | 0.240 | 0.172 | 92 | 100 | −4 | −46 | −49 | 3.23E−7 | 9.15E−7 | >1.00E−4 |
| MDA-MB-468 | 0.961 | 2.037 | 1.953 | 1.890 | 0.543 | 0.297 | 0.284 | 100 | 86 | −43 | −81 | −70 | 1.90E−7 | 4.62E−7 | 1.50E−6 |

TABLE 4

NCI five dose result for JVM 3-54

| Panel/Cell | Time | | Mean Optical Densities | | | | | Percent Growth | |
|---|---|---|---|---|---|---|---|---|---|
| | Zero | Ctrl | −8.0 | −7.0 | −6.0 | −5.0 | −4.0 | −8.0 | −7.0 |
| Leukemia | | | | | | | | | |
| CCRF-CEM | 0.799 | 2.964 | 2.929 | 2.836 | 0.740 | 0.432 | 0.403 | 98 | 94 |
| HL-60(TB) | 0.823 | 2.784 | 2.710 | 2.462 | 0.852 | 0.486 | 0.507 | 962 | 84 |
| K-562 | 0.345 | 2.367 | 2.381 | 2.287 | 1.155 | 0.362 | 0.187 | 101 | 96 |
| MOLT-4 | 1.048 | 3.075 | 3.032 | 3.039 | 2.434 | 0.606 | 0.624 | 98 | 98 |
| RPMI-8226 | 1.002 | 2.778 | 2.791 | 2.822 | 1.559 | 0.673 | 0.578 | 101 | 102 |
| SR | 0.542 | 2.530 | 2.388 | 2.410 | 1.229 | 0.380 | 0.357 | 93 | 94 |
| Non-Small Cell Lung Cancer | | | | | | | | | |
| A549/ATCC | 0.345 | 1.947 | 1.942 | 1.934 | 1.926 | 1.063 | 0.074 | 100 | 99 |
| EKVX | 0.650 | 1.621 | 1.594 | 1.548 | 1.587 | 0.792 | 0.011 | 97 | 92 |
| HOP-62 | 0.541 | 1.511 | 1.449 | 1.461 | 1.516 | 0.677 | 0.095 | 94 | 95 |
| HOP-92 | 1 506 | 1.927 | 1.889 | 1.888 | 1.514 | 0.357 | 0.115 | 91 | 91 |
| NCI-H226 | 0.734 | 1.630 | 1.608 | 1.607 | 1.630 | 1.243 | 0.291 | 98 | 97 |
| NCI-H23 | 0.556 | 1.890 | 1.826 | 1.822 | 1.782 | 0.380 | 0.169 | 95 | 95 |
| NCI-H322M | 0.704 | 1.802 | 1.801 | 1.799 | 1.848 | 1.431 | 0.039 | 100 | 100 |
| NCI-H460 | 0.292 | 2.870 | 2.913 | 2.948 | 2.895 | 0.915 | 0.086 | 102 | 103 |
| NCI-H522 | 0.659 | 1.909 | 1.844 | 1.679 | 0.261 | 0.165 | 0.189 | 95 | 82 |
| Colon Cancer | | | | | | | | | |
| COLO 205 | 0.475 | 1.689 | 1.693 | 1.685 | 0.783 | 0.126 | 0.187 | 100 | 100 |
| HCC-2998 | 0.491 | 1.929 | 1.885 | 1.909 | 2.075 | 0.236 | 0.109 | 97 | 99 |
| HCT-116 | 0.344 | 2.651 | 2.623 | 2.305 | 1.646 | 0.076 | 0.042 | 99 | 85 |
| HCT-15 | 0.253 | 1.868 | 1.798 | 1.766 | 1.702 | 0.846 | 0.054 | 96 | 94 |
| HT29 | 0.171 | 1.225 | 1.211 | 1.203 | 0.557 | 0.033 | 0.086 | 99 | 98 |
| KM12 | 0.478 | 2.541 | 2.579 | 2.545 | 2.512 | 0.517 | 0.098 | 102 | 100 |
| SW-620 | 0.330 | 2.557 | 2.559 | 2.516 | 1.120 | 0.069 | 0.091 | 100 | 98 |
| CNS Cancer | | | | | | | | | |
| SF-268 | 0.636 | 1.940 | 1.901 | 1.895 | 1.83 | 0.746 | 0.165 | 97 | 97 |
| SF-295 | 1.081 | 2.969 | 2.818 | 2.768 | 2.92 | 2.358 | 0.142 | 92 | 89 |
| SF-539 | 0.862 | 2.781 | 2.835 | 2.643 | 2.30 | 0.370 | −0.008 | 103 | 93 |
| SNB-75 | 1.311 | 2.160 | 1.901 | 1.857 | 1.87 | 1.464 | 0.462 | 70 | 64 |
| U251 | 0.351 | 1.834 | 1.824 | 1.853 | 1.75 | 0.349 | 0.017 | 99 | 101 |
| Melanoma | | | | | | | | | |
| LOX IMVI | 0.231 | 1.745 | 1.637 | 1.634 | 0.73 | 0.038 | 0.061 | 93 | 93 |
| MAL1ME-3M | 0.616 | 1.378 | 1.338 | 1.301 | 0.83 | 0.269 | 0.220 | 95 | 90 |
| M14 | 0.484 | 1.858 | 1.772 | 1.687 | 1.69 | 0.286 | 0.078 | 94 | 88 |
| MDA-MB-435 | 0.494 | 2.487 | 2.491 | 2.130 | 1.69 | 0.233 | 0.017 | 100 | 82 |
| SK-MEL-2 | 0.784 | 2.317 | 2.335 | 2.147 | 1.97 | 0.509 | 0.259 | 101 | 89 |
| SK-MEL-211 | 0.583 | 1.691 | 1.689 | 1.627 | 0.95 | 0.242 | 0.155 | 100 | 94 |
| SK-MEL-6 | 0.730 | 3.055 | 2.986 | 3.062 | 2.99 | 0.882 | 0.109 | 97 | 100 |
| UACC-257 | 1.260 | 2.678 | 2.612 | 2.567 | 2.30 | 0.859 | 0.224 | 95 | 92 |
| UACC-62 | 0.658 | 2.697 | 2.594 | 2.552 | 1.55 | 0.219 | 0.090 | 95 | 93 |
| Ovarian Cancer | | | | | | | | | |
| IGROV1 | 0.800 | 2.353 | 2.366 | 2.419 | 2.285 | 0.925 | 0.189 | 101 | 104 |
| OVCAR-3 | 0.494 | 1.604 | 1.610 | 1.617 | 0.942 | 0.035 | 0.018 | 101 | 101 |
| OVCAR-4 | 0.790 | 1.722 | 1.652 | 1.553 | 1.425 | 0.750 | 0.018 | 93 | 82 |
| OVCAR-5 | 0.583 | 1.476 | 1.432 | 1.401 | 1.364 | 0.194 | 0.161 | 95 | 92 |
| OVCAR-8 | 0.375 | 1.793 | 1.785 | 1.786 | 1.501 | 0.348 | 0.083 | 99 | 99 |
| NCI/ADR- | 0.582 | 2.018 | 1.927 | 1.869 | 2.010 | 1.821 | 0.917 | 94 | 90 |
| SK-OV-3 | 0.854 | 1.677 | 1.663 | 1.691 | 1.738 | 1.408 | 0.003 | 98 | 102 |

TABLE 4-continued

NCI five dose result for JVM 3-54

Renal Cancer

| | | | | | | | | | |
|---|---|---|---|---|---|---|---|---|---|
| 786-0 | 1.063 | 2.952 | 2.907 | 2.782 | 2.860 | 0.467 | 0.097 | 98 | 91 |
| A498 | 1.728 | 2.760 | 2.733 | 2.697 | 2.753 | 2.120 | 0.020 | 97 | 94 |
| ACHN | 0.338 | 1.598 | 1.604 | 1.555 | 1.535 | 0.478 | 0.032 | 100 | 97 |
| CAKI-1 | 0.444 | 2.007 | 1.892• | 1.851 | 1.868 | 1.302 | 0.014 | 93 | 90 |
| RXF 393 | 0.642 | 1.341 | 1.342 | 1.310 | 1.141 | 0.229 | 0.003 | 100 | 95 |
| SN12C | 0.749 | 2.645 | 2.642 | 2.668 | 2.431 | 0.758 | 0.119 | 100 | 101 |
| TK-10 | 0.628 | 1.939 | 1.895 | 1.850 | 1.616 | 0.332 | 0.006 | 97 | 93 |
| UO-31 | 0.884 | 2.302 | 2.098 | 2.070 | 2.129 | 1.521 | 0.045 | 86 | 84 |

Prostate Cancer

| | | | | | | | | | |
|---|---|---|---|---|---|---|---|---|---|
| PC-3 | 0.694 | 1.919 | 1.905 | 1.906 | 1.805 | 0.629 | 0.048 | 99 | 99 |
| DU-145 | 0.518 | 1.927 | 1.918 | 1.902 | 1.914 | 0.548 | 0.019 | 99 | 98 |

Breast Cancer

| | | | | | | | | | |
|---|---|---|---|---|---|---|---|---|---|
| MCF7 | 0.298 | 1.683 | 1.568 | 1.499 | 0.626 | 0.093 | 0.174 | 92 | 87 |
| MDA-MB-231/ATCC | 0.566 | 1.417 | 1.438 | 1.452 | 1.235 | 0.139 | 0.083 | 103 | 104 |
| HS578T | 1.079 | 2.011 | 1.918 | 1.934 | 1.918 | 0.984 | 0.768 | 90 | 92 |
| BT-549 | 1.171 | 2.468 | 2.474 | 2.354 | 2.190 | 0.447 | 0.022 | 100 | 91 |
| T-47D | 0.552 | 1.146 | 1.118 | 1.102 | 0.970 | 0.315 | 0.375 | 95 | 93 |
| MDA-MB-468 | 0.961 | 2.116 | 2.023 | 2.016 | 1.257 | 0.391 | 0.296 | 92 | 91 |

| | Log10 Concentration Percent Growth | | | | | |
|---|---|---|---|---|---|---|
| Panel/Cell | −6.0 | −5.0 | −4.0 | GI50 | TGI | LC50 |

Leukemia

| | | | | | | |
|---|---|---|---|---|---|---|
| CCRF-CEM | −7 | −46 | −50 | 2.72E−7 | 8.45E−7 | >1.00E−4 |
| HL-60(TB) | 1 | −41 | −38 | 2.56E−7 | 1.08E−6 | >1.00E−4 |
| K-562 | 40 | 1 | −46 | 6.65E−7 | 1.04E−5 | >1.00E−4 |
| MOLT-4 | 68 | −42 | −41 | 1.47E−6 | 4.15E−6 | >1.00E−4 |
| RPMI-8226 | 31 | −33 | −42 | 5.47E−7 | 3.08E−6 | >1.00E−4 |
| SR | 35 | −29 | −34 | 5.49E−7 | 3.51E−6 | >1.00E−4 |

Non-Small Cell Lung Cancer

| | | | | | | |
|---|---|---|---|---|---|---|
| A549/ATCC | 99 | 45 | −79 | 8.02E−6 | 2.31E−5 | 5.87E−5 |
| EKVX | 96 | 15 | −98 | 3.69E−6 | 1.35E−5 | 3.73E−5 |
| HOP-62 | 101 | 14 | −82 | 3.84E−6 | 1.40E−5 | 4.61E−5 |
| HOP-92 | 2 | −76 | −92 | 2.87E−7 | 1.06E−6 | 4.61E−5 |
| NCI-H226 | 100 | 57 | −60 | 1.14E−5 | 3.05E−5 | 8.16E−5 |
| NCI-H23 | 92 | 32 | −70 | 2.18E−6 | 5.54E−6 | 3.04E−5 |
| NCI-H322M | 104 | 66 | −94 | 1.26E−5 | 2.58E−5 | 5.29E−5 |
| NCI-H460 | 101 | 24 | −71 | 4.61E−6 | 1.80E−5 | 6.07E−5 |
| NCI-H522 | −60 | −75 | −71 | 1.67E−7 | 3.75E−7 | 8.45E−7 |

Colon Cancer

| | | | | | | |
|---|---|---|---|---|---|---|
| COLO 205 | 25 | −73 | −61 | 4.66E−7 | 1.80E−6 | 5.79E−6 |
| HCC-2998 | 110 | −52 | −78 | 2.35E−6 | 4.78E−6 | 9.73E−6 |
| HCT-116 | 56 | −78 | −88 | 1.12E−6 | 2.63E−6 | 6.19E−6 |
| HCT-15 | 90 | 37 | 79 | 5.61E−6 | 2.08E−5 | 5.63E−5 |
| HT29 | 37 | −81 | −50 | 6.05E−7 | 2.05E−6 | 1.00E−4 |
| KM12 | 99 | 2 | −80 | 3.18E−6 | 1.05E−5 | 4.33E−5 |
| SW-620 | 35 | −79 | −72 | 5.86E−7 | 2.04E−6 | 5.56E−6 |

CNS Cancer

| | | | | | | |
|---|---|---|---|---|---|---|
| SF-268 | 92 | 8 | −74 | 3.18E−6 | 1.26E−5 | 5.10E−5 |
| SF-295 | 98 | 68 | −87 | 1.30E−5 | 2.74E−5 | 5.77E−5 |
| SF-539 | 75 | −57 | −100 | 1.55E−6 | 3.71E−6 | 8.84E−6 |
| SNB-75 | 67 | 18 | −65 | 2.19E−6 | 1.65E−5 | 6.63E−5 |
| U251 | 95 | −1 | −95 | 2.94E−6 | 9.83E−6 | 3.33E−5 |

Melanoma

| | | | | | | |
|---|---|---|---|---|---|---|
| LOX IMVI | 33 | −84 | −74 | 5.19E−7 | 1.92E−6 | 5.15E−6 |
| MAL1ME-3M | 29 | −56 | −64 | 4.52E−7 | 2.19E−6 | 8.43E−6 |
| M14 | 88 | −41 | −84 | 1.97E−6 | 4.82E−6 | 1.63E−5 |
| MDA-MB-435 | 60 | −53 | −97 | 1.24E−6 | 3.41E−6 | 9.42E−6 |
| SK-MEL-2 | 78 | −35 | −67 | 1.77E−6 | 4.89E−6 | 2.93E−5 |
| SK-MEL-211 | 33 | −58 | −73 | 5.29E−7 | 2.30E−6 | 8.08E−6 |
| SK-MEL-6 | 98 | 7 | −85 | 3.33E−6 | 1.18E−5 | 4.14E−5 |
| UACC-257 | 74 | −32 | −82 | 1.68E−6 | 4.99E−6 | 2.29E−5 |
| UACC-62 | 44 | −67 | −86 | 7.53E−7 | 2.50E−6 | 7.06E−6 |

TABLE 4-continued

NCI five dose result for JVM 3-54

| Ovarian Cancer | | | | | | |
|---|---|---|---|---|---|---|
| IGROV1 | 96 | 8 | −76 | 3.32E−6 | 1.24E−5 | 4.86E−5 |
| OVCAR-3 | 40 | −93 | −96 | 6.93E−7 | 2.01E−6 | 4.76E−6 |
| OVCAR-4 | 68 | −5 | −98 | 1.77E−6 | 8.53−6 | 3.05E−5 |
| OVCAR-5 | 87 | −67 | −72 | 1.75E−6 | 3.69E−6 | 7.79E−6 |
| OVCAR-8 | 79 | −7 | −78 | 2.18E−6 | 8.26E−6 | 4.02E−5 |
| NCI/ADR- | 99 | 86 | 23 | 3.77E−5 | >1.00E−4 | >1.00E−4 |
| SK-OV-3 | 107 | 67 | −100 | 1.27E−5 | 2.53E−5 | 5.04E−5 |
| Renal Cancer | | | | | | |
| 786-0 | 95 | −56 | −91 | 1.99E−6 | 4.25E−6 | 9.11E−6 |
| A498 | 99 | 38 | −99 | 6.36E−6 | 1.89E−5 | 4.39E−5 |
| ACHN | 95 | 11 | −91 | 3.44E−6 | 1.29E−5 | 3.98E−5 |
| CAKI-1 | 91 | 55 | −97 | 1.08E−5 | 2.30E−5 | 4.91E−5 |
| RXF 393 | 71 | −64 | −100 | 1.44E−6 | 3.36E−6 | 7.84E−6 |
| SN12C | 89 | . | −84 | 2.75E−6 | 1.01E−5 | 3.95E−5 |
| TK-10 | 75 | −47 | −99 | 1.61E−6 | 4.12E−6 | 1.13E−5 |
| UO-31 | 88 | 45 | −95 | 7.61E−6 | 2.09E−5 | 4.77E−5 |
| Prostate Cancer | | | | | | |
| PC-3 | 91 | −9 | −93 | 2.55E−6 | 8.05E−6 | 3.05E−5 |
| DU-145 | 99 | 2 | −96 | 3.21E−6 | 1.05E−5 | 3.38E−5 |
| Breast Cancer | | | | | | |
| MCF7 | 24 | −69 | −42 | 3.828E− | 1.80E−6 | 6.83E−6 |
| MDA-MB-231/ATCC | 79 | −76 | −85 | 1.53E−6 | 3.24E−6 | >1.00E−4 |
| HS578T | 90 | −9 | −27 | 2.54E−6 | 8.14E−6 | 8.23E−6 |
| BT-549 | 79 | −62 | −98 | 1.60E−6 | 3.63E−6 | 3.570,5 |
| T-47D | 70 | −43 | −32 | 1.51E−6 | 4.17E−6 | >1.00E−4 |
| MDA-MB-468 | 26 | −59 | −69 | 4.26E−7 | 2.00E−6 | 7.76E−6 |

Example 7 bis(((1aR,7aS,10aS,10bS,E)-1a-Methyl-8-methylene-9-oxo-1a,2,3,6,7,7a,8,9,10a,10b-decahydrooxireno[2',3':9,10]cyclodeca[1,2-b]furan-5-yl)methyl)decane-1,10-diyldicarbamate (JVM 3-65)

To the triazole intermediate of MMB (5) (60 mg, 0.167 mmol) in dichloromethane (2 mL) and 1,10-diaminodecane (19.9 mg, 0.116 mmol) was added at ambient temperature. The reaction mixture was stirred for 2 h at ambient temperature. When the reaction was completed (monitored by TLC), water was added to the reaction mixture and the aqueous mixture was extracted with dichloromethane. The organic layer was washed with water, followed by brine solution, dried over anhydrous $Na_2SO_4$ and concentrated to afford the crude product. The crude product was purified by column chromatography (silica gel, 2% methanol in dichloromethane) to afford compound JVM 3-65 as white solid. (Yield: 75%).

$^1$H NMR (CDCl3), 400 MHz): δ 6.24 (s, 1H), 5.67 (t, J=2.8 Hz, 1H), 5.54 (s, 1H), 4.69 (brs, 1H), 4.62 (d, J=12.8 Hz, 1H), 4.49 (d, J=12.4 Hz, 1H), 3.84 (t, J=9.2 Hz, 1H), 3.18-3.13 (m, 2H), 2.95 (t, J=9.1 Hz, 1H), 2.88 (d, J=9.6 Hz, 1H), 2.49-2.13 (m, 6H), 1.65 (t, J=10.8 Hz, 1H), 1.54 (s, 3H), 1.47 (t, J=6.8 Hz, 2H), 1.27 (brs, 6H), 1.11 (t, J=12 Hz, 1H). $^{13}$C NMR (CDCl3, 100 MHz): δ 169.5, 156.2, 139.0, 135.7, 130.2, 120.2, 81.2, 67.2, 63.4, 60.0, 42.7, 41.2, 36.8, 30.1, 29.5, 29.3, 26.8, 26.0, 24.8, 23.9, 18.1 ppm.

Example 8 bis(((1aR,7aS,10aS,10bS,E)-1a-Methyl-8-methylene-9-oxo-1a,2,3,6,7,7a,8,9,10a,10b-decahydrooxireno[2',3':9,10]cyclodeca[1,2-b]furan-5-yl)methyl)nonane-1,9-diyldicarbamate (JVM 3-61)

To the triazole intermediate of MMB (5) (60 mg, 0.167 mmol) in dichloromethane (2 mL) 1,9-diaminononane (18.3 mg, 0.116 mmol) was added at ambient temperature. The reaction mixture was stirred for 3 h at ambient temperature. When the reaction was completed (monitored by TLC), water was added to the reaction mixture and the aqueous mixture was extracted with dichloromethane. The organic layer was washed with water, followed by brine solution, dried over anhydrous $Na_2SO_4$ and concentrated to afford the crude product. The crude product was purified by column chromatography (silica gel, 2% methanol in dichloromethane) to afford compound JVM 3-61 as white solid. (Yield: 80%).

$^1$H NMR (CDCl$_3$), 400 MHz): δ 6.23 (s, 1H), 5.68 (t, J=7.2 Hz, 1H), 5.54(s, 1H), 4.67 (brs, 1H), 4.62 (d, J=12.8 Hz, 1H), 4.49 (d, J=12.4 Hz, 1H), 3.84 (t, J=9.2 Hz, 1H), 3.18-3.13 (m, 2H), 2.94 (t, J=9.2 Hz, 1H), 2.87 (d, J=9.6 Hz, 1H), 2.49-2.13 (m, 6H), 1.65 (t, J=11.2 Hz, 1H), 1.55 (s, 3H), 1.47 (t, J=12.4 Hz, 2H), 1.33-1.24 (m, 6 H), 1.11 (t, J=12 Hz, 1H). $^{13}$C NMR (CDCl$_{3, 100}$ MHz): δ 169.5, 156.2, 139.0, 135.7, 130.1, 120.2, 81.2, 67.2, 63.4, 60.0, 42.8, 41.2, 36.8, 30.0, 29.4, 29.2, 26.7, 26.0, 24.8, 23.9, 18.1 ppm.

Example 9 bis(((1aR,7aS,10aS,10bS,E)-1a-Methyl-8-methyl-ene-9-oxo-1a,2,3,6,7,7a,8,9,10a,10b-decahy droox-ireno[2',3':9,10]cyclodeca[1,2-b]furan-5-yl)methyl) octane-1,8-diyldicarbamate (JVM 3-62)

To the triazole intermediate of MMB (5) (60 mg, 0.167 mmol) in dichloromethane (2 mL) 1,8-diaminooctane (16.7 mg, 0.116 mmol) was added at ambient temperature. The reaction mixture was stirred for 3 h at ambient temperature. When the reaction was completed (monitored by TLC), water was added to the reaction mixture and the aqueous mixture was extracted with dichloromethane. The organic layer was washed with water, followed by brine solution, dried over anhydrous $Na_2SO_4$ and concentrated to afford the crude product. The crude product was purified by column chromatography (silica gel, 3% methanol in dichloromethane) to afford compound JVM 3-62 as white solid. (Yield: 77%).

$^1$H NMR (CDCl$_3$), 400 MHz): δ 6.24 (s, 1H), 5.68 (t, J=7.2 Hz, 1H), 5.55 (s, 1H), 4.70 (brs, 1H), 4.62 (d, J=12.4 Hz, 1H), 4.49 (d, J=12.8 Hz, 1H), 3.85 (t, J=9.2 Hz, 1H), 3.18-3.13 (m, 2H), 2.95 (t, J=9.2 Hz, 1H), 2.88 (d, J=9.2 Hz, 1H), 2.46-2.13 (m, 6H), 1.65 (t, J=11.6 Hz, 1H), 1.54 (s, 3H), 1.47 (t, J=6.4 Hz, 2H), 1.33-1.24 (m, 4H), 1.11 (t, J=11.6 Hz, 1H). $^{13}$C NMR (CDCl$_3$, 100 MHz): δ 169.5, 156.2, 139.1, 135.7, 130.2, 120.2, 81.2, 67.2, 63.4, 60.0, 42.8, 41.2, 36.8, 30.0, 29.2, 26.7, 26.0, 24.8, 23.9, 18.1 ppm.

Example 10 bis(((1aR,7aS,10aS,10bS,E)-1a-Methyl-8-methyl-ene-9-oxo-1a,2,3,6,7,7a,8,9,10a,10b-decah ydroox-ireno[2',3':9,10]cyclodeca[1,2-b]furan-5-yl)methyl) heptane-1,7-diyldicarbamate (JVM 3-58)

To the triazole intermediate of MMB (5) (60 mg, 0.167 mmol) in dichloromethane (2 mL) 1,7-diaminoheptane (15.1 mg, 0.116 mmol) was added at ambient temperature. The reaction mixture was stirred for 3 h at ambient temperature. When the reaction was completed (monitored by TLC), water was added to the reaction mixture and the aqueous mixture was extracted with dichloromethane. The organic layer was washed with water, followed by brine solution, dried over anhydrous $Na_2SO_4$ and concentrated to afford the crude product. The crude product was purified by column chromatography (silica gel, 3% methanol in dichloromethane) to afford compound JVM 3-58 as white solid. (Yield: 70%).

$^1$H NMR (CDCl$_3$), 400 MHz): δ 6.24 (s, 1H), 5.68 (t, J=8 Hz, 1H), 5.54 (s, 1H), 4.73 (brs, 1H), 4.61 (d, J=12.8 Hz, 1H), 4.50 (d, J=12.4 Hz, 1H), 3.85 (t, J=9.2 Hz, 1H), 3.18-3.13 (m, 2H), 2.96 (t, J=8.8 Hz, 1H), 2.88 (d, J=9.6 Hz, 1H), 2.49-2.13 (m, 6H), 1.65 (t, J=11.6 Hz, 1H), 1.54 (s, 3H), 1.47 (t, J=6.8 Hz, 2H), 1.33-1.30 (m, 3H), 1.10 (t, J=12 Hz, 1H). $^{13}$C NMR (CDCl$_3$, 100 MHz): δ 169.2, 155.9, 138.8, 135.4, 129.9, 119.9, 80.9, 66.9, 63.1, 59.7, 42.4, 40.8, 36.5, 29.7, 28.6, 26.4, 25.7, 24.5, 23.6, 17.8 ppm.

Example 11 bis(((1aR,7aS,10aS,10bS,E)-1a-Methyl-8-methyl-ene-9-oxo-1a,2,3,6,7,7a,8,9,10a,10b-dec ahydroox-ireno[2',3':9,10]cyclodeca[1,2-b]furan-5-yl)methyl) hexane-1,6-diyldicarbamate (JVM 3-64)

To the triazole intermediate of MMB (5) (60 mg, 0.167 mmol) in dichloromethane (2 mL) hexamethylenediamine (13.4 mg, 0.116 mmol) was added at ambient temperature. The reaction mixture was stirred for 3 h at ambient temperature. When the reaction was completed (monitored by TLC), water was added to the reaction mixture and the aqueous mixture was extracted with dichloromethane. The organic layer was washed with water, followed by brine solution, dried over anhydrous $Na_2SO_4$ and concentrated to afford the crude product. The crude product was purified by column chromatography (silica gel, 3% methanol in dichloromethane) to afford compound JVM 3-64 as white solid. (Yield: 75%).

$^1$H NMR (CDCl$_3$), 400 MHz): δ 6.24 (d, J=3.6 Hz, 1H), 5.70 (t, J=8.4 Hz, 1H), 5.55 (d, J=3.2 Hz, 1H), 4.72 (brs, 1H), 4.62 (d, J=13.2 Hz, 1H), 4.49 (d, J=12.8 Hz, 1H), 3.84 (t, J=9.2 Hz, 1H), 3.18-3.13 (m, 2H), 2.95 (t, J=3.6 Hz, 1H), 2.87 (d, J=9.6 Hz, 1H), 2.46-2.13 (m, 6H), 1.65 (t, J=10.8 Hz, 1H), 1.54 (s, 3H), 1.48 (t, J=6.4 Hz, 2H), 1.33-1.31 (m, 2H), 1.10 (t, J=11.6 Hz, 1H). $^{13}$C NMR (CDCl$_3$, 100 MHz): δ 169.6, 156.3, 139.1, 135.7, 130.2, 120.2, 81.2, 67.2, 63.4, 60.1, 42.8, 41.0, 36.8, 30.0, 26.3, 26.0, 24.9, 23.9, 18.1 ppm.

Example 12 bis(((1aR,7aS,10aS,10bS,E)-1a-Methyl-8-methyl-ene-9-oxo-1a,2,3,6,7,7a,8,9,10a,10b-decah ydroox-ireno[2',3':9,10]cyclodeca[1,2-b]furan-5-yl)methyl) pentane-1,5-diyldicarbamate (JVM 2-76)

To the triazole intermediate of MMB (5) (60 mg, 0.167 mmol) in dichloromethane (2 mL) cadaverine dihydrochloride (20.3 mg, 0.116 mmol) and triethylamine (43.4 mg, 0.43 mmol) were added at ambient temperature. The reaction mixture was stirred for 6 h at ambient temperature. When the reaction was completed (monitored by TLC), water was added to the reaction mixture and the aqueous mixture was extracted with dichloromethane. The organic layer was washed with water, followed by brine solution, dried over anhydrous $Na_2SO_4$ and concentrated to afford the crude product. The crude product was purified by column chromatography (silica gel, 3% methanol in dichloromethane) to afford compound JVM 2-76 as white solid. (Yield: 72%).

$^1$H NMR (CDCl$_3$), 400 MHz): δ 6.24 (d, J=2.8 Hz, 1H), 5.68 (t, J=8.8 Hz, 1H), 5.55 (d, J=2.4 Hz, 1H), 4.74 (brs, 1H), 4.61 (d, J=12 Hz, 1H), 4.50 (d, J=12.4 Hz, 1H), 3.85 (t, J=9.2 Hz, 1H), 3.17 (d, J=6.4 Hz, 2H), 2.96 (t, J=3.5 Hz, 1H), 2.88 (d, J=9.6 Hz, 1H), 2.46-2.13 (m, 6H), 1.66 (t, J=9.6 Hz, 1H), 1.56-1.49 (m, 6H), 1.49-1.33 (m, 1H), 1.10 (t, J=12.4 Hz, 1H). $^{13}$C NMR (CDCl$_3$, 100 MHz): δ 169.6, 156.3, 139.0, 135.6, 130.3, 120.2, 81.2, 67.2, 63.4, 60.1, 42.8, 40.9, 36.8, 29.7, 25.9, 24.8 23.9, 23.8, 18.1 ppm.

Example 13 bis(((1aR,7aS,10aS,10bS,E)-1a-Methyl-8-methyl-ene-9-oxo-1a,2,3,6,7,7a,8,9,10a,10b-deca hydroox-ireno[2',3':9,10]cyclodeca[1,2-b]furan-5-yl)methyl) butane-1,4-diyldicarbamate (JVM 3-54)

To the triazole intermediate of MMB (5) (60 mg, 0.167 mmol) in dichloromethane (2 mL) 1,4-diaminobutane (10.2 mg, 0.116 mmol) was added at ambient temperature. The reaction mixture was stirred for 3 h at ambient temperature. When the reaction was completed (monitored by TLC), water was added to the reaction mixture and the aqueous mixture was extracted with dichloromethane. The organic layer was washed with water, followed by brine solution, dried over anhydrous $Na_2SO_4$ and concentrated to afford the crude product. The crude product was purified by column chromatography (silica gel, 3% methanol in dichloromethane) to afford compound JVM 3-54 as white solid. (Yield: 65%).

$^1$H NMR (CDCl$_3$), 400 MHz): δ 6.24 (d, J=3.6 Hz, 1H), 5.69 (t, J=8.4 Hz, 1H), 5.55 (d, J=2.8 Hz, 1H), 4.85 (brs, 1H), 4.61 (d, J=12.4 Hz, 1H), 4.50 (d, J=12.8 Hz, 1H), 3.85 (t, J=8.8 Hz, 1H), 3.19 (d, J=4 Hz, 2H), 2.97 (t, J=3.6 Hz, 1H), 2.88 (d, J=9.6 Hz, 1H), 2.49-2.13 (m, 6H), 1.65 (t, J=10 Hz, 1H), 1.54 (s, 3H), 1.50 (brs, 2H), 1.10 (t, J=11.6 Hz, 1H). $^{13}$C NMR (CDCl$_3$, 100 MHz): δ 169.6, 156.3, 139.1, 135.5, 130.4, 120.2, 81.2, 67.3, 63.4, 60.1, 42.8, 40.7, 36.8, 27.3, 26.0, 24.9, 23.9, 18.1 ppm.

Example 14 bis(((1aR,7aS,10aS,10bS,E)-1a-Methyl-8-methylene-9-oxo-1a,2,3,6,7,7a,8,9,10a,10b-decahydrooxireno[2',3':9,10]cyclodeca[1,2-b]furan-5-yl)methyl) propane-1,3-diyldicarbamate (JVM 3-55A)

To the triazole intermediate of MMB (5) (60 mg, 0.167 mmol) in dichloromethane (2 mL) 1,3-diaminopropane (8.66 mg, 0.116 mmol) was added at ambient temperature. The reaction mixture was stirred for 6 h at ambient temperature. When the reaction was completed (monitored by TLC), water was added to the reaction mixture and the aqueous mixture was extracted with dichloromethane. The organic layer was washed with water, followed by brine solution, dried over anhydrous Na$_2$SO$_4$ and concentrated to afford the crude product. The crude product was purified by column chromatography (silica gel, 3% methanol in dichloromethane) to afford compound JVM 3-55A as white solid. (Yield: 60%).

$^1$H NMR (CDCl$_3$), 400 MHz): δ 6.24 (d, J=3.2 Hz, 1H), 5.68 (t, J=7.2 Hz, 1H), 5.56 (d, J=2.4 Hz, 1H), 5.12 (s, 1H), 4.61 (d, J=12.8 Hz, 1H), 4.50 (d, J=12.4 Hz, 1H), 3.85 (t, J=9.2 Hz, 1H), 3.25-3.20 (m, 2H), 2.95 (t, J=3.2 Hz, 1H), 2.88 (d, J=9.2 Hz, 1H), 2.49-2.13 (m, 6H), 1.68-1.62 (m, 2H), 1.54 (s, 3H), 1.11 (t, J=11.6 Hz, 1H). $^{13}$C NMR (CDCl$_3$, 100 MHz): δ 169.6, 156.2, 139.0, 135.5, 130.0, 120.2, 81.2, 67.3, 63.4, 60.1, 42.7, 37.6, 36.8, 25.9, 24.8, 23.9, 18.1 ppm.

Example 15 bis(((1aR,7aS,10aS,10bS,E)-1a-Methyl-8-methylene-9-oxo-1a,2,3,6,7,7a,8,9,10a,10b-decahydrooxireno[2',3':9,10]cyclodeca[1,2-b]furan-5-yl)methyl) 4,4'-(decane-1,10-diylbis(azanediyl))bis(4-oxobutanoate) (JVM 3-67)

To the stirred solution of MMB succinate (7) (50 mg, 0.137 mmol) in dichloromethane, EDC (39.3 mg, 0.205 mmol), HOBt (27.6 mg, 0.205 mmol), triethylamine (41.5 mg, 0.411 mmol) and 1,10-diaminodecane (16.5 mg, 0.095 mmol) were added at ambient temperature. The reaction mixture was stirred for 5 h at ambient temperature. When the reaction was completed (monitored by TLC), water was added to the reaction mixture and the aqueous mixture was extracted with dichloromethane. The organic layer was washed with water, followed by brine solution, dried over anhydrous Na$_2$SO$_4$ and concentrated to afford the crude product. The crude product was purified by column chromatography (silica gel, 3% methanol in dichloromethane) to afford compound JVM 3-67 as white solid. (Yield: 67%).

$^1$H NMR (CDCl$_3$, 400 MHz): δ 6.25 (d, J=3.2 Hz, 1H), 5.67 (t, J=7.2 Hz, 1H), 5.60 (d, J=2.8 Hz, 2H), 4.68 (d, J=12.8 Hz, 1H), 4.49 (d, J=12.8 Hz, 1H), 3.85 (t, J=8.8 Hz, 1H), 3.25-3.21 (m, 2H), 2.91 (t, J=9.6 Hz, 1H), 2.86 (d, J=9.2 Hz, 1H), 2.69-2.64 (m, 2H), 2.52-2.09 (m, 8H), 1.66 (t, J=11.2 Hz, 1H), 1.54 (s, 3H), 1.48 (t, J=7.2 Hz, 2H), 1.31-1.27 (m, 6H), 1.11 (t, J=11.6 Hz, 1H) ppm.

Example 16 bis(((1aR,7aS,10aS,10bS,E)-1a-Methyl-8-methylene-9-oxo-1a,2,3,6,7,7a,8,9,10a,10b-decahydrooxireno[2',3':9,10]cyclodeca[1,2-b]furan-5-yl)methyl) 4,4'-(nonane-1,9-diylbis(azanediyl))bis(4-oxobutanoate) (JVM 2-92)

To the stirred solution of MMB succinate (7) (50 mg, 0.137 mmol) in dichloromethane, EDC (39.3 mg, 0.205 mmol), HOBt (27.6 mg, 0.205 mmol), triethylamine (41.5 mg, 0.411 mmol) and 1,9-diaminononane (14.8 mg, 0.095 mmol) were added at ambient temperature. The reaction mixture was stirred for 6 h at ambient temperature. When the reaction was completed (monitored by TLC), water was added to the reaction mixture and the aqueous mixture was extracted with dichloromethane. The organic layer was washed with water, followed by brine solution, dried over anhydrous Na$_2$SO$_4$ and concentrated to afford the crude product. The crude product was purified by column chromatography (silica gel, 3% methanol in dichloromethane) to afford compound JVM 2-92 as white solid. (Yield: 70%).

$^1$H NMR (CDCl$_3$, 400 MHz): δ 6.25 (d, J=3.2 Hz, 1H), 5.69-5.65 (m, 2H), 5.61 (d, J=3.2 Hz, 1H), 4.68 (d, J=12.8 Hz, 1H), 4.50 (d, J=12.8 Hz, 1H), 3.85 (t, J=9.2 Hz, 1H), 3.27-3.19 (m, 2H), 2.92 (t, J=8.8 Hz, 1H), 2.86 (d, J=9.2 Hz, 1H), 2.70-2.64 (m, 2H), 2.52-2.13 (m, 8H), 1.66 (t, J=3.2 Hz, 1H), 1.54 (s, 3H), 1.47 (t, J=7.2 Hz, 2H), 1.31-1.27 (m, 6H), 1.11 (t, J=11.6 Hz, 1H) ppm.

Example 17 bis(((1aR,7aS,10aS,10bS,E)-1a-Methyl-8-methylene-9-oxo-1a,2,3,6,7,7a,8,9,10a,10b-decahydrooxireno[2',3':9,10]cyclodeca[1,2-b]furan-5-yl)methyl) 4,4'-(octane-1,8-diylbis(azanediyl))bis(4-oxobutanoate) (JVM 2-87)

To the stirred solution of MMB succinate (7) (50 mg, 0.137 mmol) in dichloromethane, EDC (39.3 mg, 0.205 mmol), HOBt (27.6 mg, 0.205 mmol), triethylamine (41.5 mg, 0.411 mmol) and 1,8-diaminooctane (13.3 mg, 0.095 mmol) were added at ambient temperature. The reaction mixture was stirred for 6 h at ambient temperature. When the reaction was completed (monitored by TLC), water was added to the reaction mixture and the aqueous mixture was extracted with dichloromethane. The organic layer was washed with water, followed by brine solution, dried over anhydrous Na$_2$SO$_4$ and concentrated to afford the crude product. The crude product was purified by column chromatography (silica gel, 3% methanol in dichloromethane) to afford compound JVM 2-87 as white solid. (Yield: 68%).

$^1$H NMR (CDCl$_3$, 400 MHz): δ 6.25 (d, J=3.2 Hz, 1H), 5.69-5.67 (m, 2H), 5.61 (d, J=3.2 Hz, 1H), 4.67 (d, J=12.4 Hz, 1H), 4.50 (d, J=12.8 Hz, 1H), 3.85 (t, J=8.8 Hz, 1H), 3.23-3.20 (m, 2H), 2.93 (t, J=9.2 Hz, 1H), 2.87 (d, J=9.2 Hz, 1H), 2.67-2.64 (m, 2H), 2.48-2.13 (m, 8H), 1.66 (t, J=10 Hz, 1H), 1.54 (s, 3H), 1.47 (t, J=6.8 Hz, 2H), 1.29 (s, 4H), 1.11 (t, J=11.6 Hz, 1H) ppm.

Example 18 bis(((1aR,7aS,10aS,10bS,E)-1a-Methyl-8-methylene-9-oxo-1a,2,3,6,7,7a,8,9,10a,10b-decahydrooxireno[2',3':9,10]cyclodeca[1,2-b]furan-5-yl)methyl) 4,4'-(heptane-1,7-diylbis(azanediyl))bis(4-oxobutanoate) (JVM 3-69)

To the stirred solution of MMB succinate (7) (50 mg, 0.137 mmol) in dichloromethane, EDC (39.3 mg, 0.205 mmol), HOBt (27.6 mg, 0.205 mmol), triethylamine (41.5 mg, 0.411 mmol) and 1,7-diaminoheptane (12.3 mg, 0.095 mmol) were added at ambient temperature. The reaction mixture was stirred for 5 h at ambient temperature. When the reaction was completed (monitored by TLC), water was added to the reaction mixture and the aqueous mixture was extracted with dichloromethane. The organic layer was washed with water, followed by brine solution, dried over anhydrous $Na_2SO_4$ and concentrated to afford the crude product. The crude product was purified by column chromatography (silica gel, 3% methanol in dichloromethane) to afford compound JVM 3-69 as white solid. (Yield: 67%).

$^1$H NMR ($CDCl_3$, 400 MHz): δ 6.24 (d, J=3.2 Hz, 1H), 5.67-5.65 (m, 2H), 5.60 (d, J=2.8 Hz, 1H), 4.66 (d, J=12.4 Hz, 1H), 4.51 (d, J=12.8 Hz, 1H), 3.85 (t, J=9.2 Hz, 1H), 3.24-3.19 (m, 2H), 2.95 (t, J=9.2 Hz, 1H), 2.87 (d, J=9.2 Hz, 1H), 2.65 (t, J=6.4 Hz, 2H), 2.48-2.13 (m, 8H), 1.66 (t, J=11.2 Hz, 1H), 1.54 (s, 3H), 1.48 (t, J=6.8 Hz, 2H), 1.31 (s, 4H), 1.11 (t, J=12 Hz, 1H). $^{13}$C NMR ($CDCl_3$, 100 MHz): δ 172.9, 171.1, 169.6, 139.0, 134.9, 130.2, 120.4, 81.3, 67.1, 63.4, 60.0, 42.7, 39.6, 36.8, 30.8, 29.5, 29.5, 28.8, 26.7, 25.9, 24.6, 23.9, 18.1 ppm.

Example 19 bis(((1aR,7aS,10aS,10bS,E)-1a-Methyl-8-methylene-9-oxo-1a,2,3,6,7,7a,8,9,10a,10b-decahydrooxireno[2',3':9,10]cyclodeca[1,2-b]furan-5-yl)methyl) 4,4'-(hexane-1,6-diylbis(azanediyl))bis(4-oxobutanoate) (JVM 2-85)

To the stirred solution of MMB succinate (7) (50 mg, 0.137 mmol) in dichloromethane, EDC (39.3 mg, 0.205 mmol), HOBt (27.6 mg, 0.205 mmol), triethylamine (41.5 mg, 0.411 mmol) and 1,6-diaminohexane (11 mg, 0.095 mmol) were added at ambient temperature. The reaction mixture was stirred for 6 h at ambient temperature. When the reaction was completed (monitored by TLC), water was added to the reaction mixture and the aqueous mixture was extracted with dichloromethane. The organic layer was washed with water, followed by brine solution, dried over anhydrous $Na_2SO_4$ and concentrated to afford the crude product. The crude product was purified by column chromatography (silica gel, 3% methanol in dichloromethane) to afford compound JVM 2-85 as white solid. (Yield: 65%).

$^1$H NMR ($CDCl_3$, 400 MHz): δ 6.24 (d, J=3.2 Hz, 1H), 5.83 (brs, 1H), 5.66 (t, J=7.6 Hz, 1H), 5.60(d, J=2.8 Hz, 1H), 4.64(d, J=12.8 Hz, 1H), 4.52(d, J=12.8 Hz, 1H), 3.85(t, J=9.2 Hz, 1H), 3.24-3.21(m, 2H), 2.98(t, J=9.2 Hz, 1H), 2.87(d, J=9.2 Hz, 1H), 2.67-2.63(m, 2H), 2.49-2.13(m, 8H), 1.66(t, J=10.8 Hz, 1H), 1.54(s, 3H), 1.48(t, J=6.4 Hz, 2H), 1.32(brs, 2H), 1.11 (t, J=12 Hz, 1H) ppm.

Example 20 bis(((1aR,7aS,10aS,10bS,E)-1a-Methyl-8-methylene-9-oxo-1a,2,3,6,7,7a,8,9,10a,10b-decahydrooxireno[2',3':9,10]cyclodeca[1,2-b]furan-5-yl)methyl) 4,4'-(pentane-1,5-diylbis(azanediyl))bis(4-oxobutanoate) (JVM 2-79)

To the stirred solution of MMB succinate (7) (50 mg, 0.137 mmol) in dichloromethane, EDC (39.3 mg, 0.205 mmol), HOBt (27.6 mg, 0.205 mmol), triethylamine (41.5 mg, 0.411 mmol) and cadaverine dihydrochloride (16.6 mg, 0.095 mmol) were added at ambient temperature. The reaction mixture was stirred for 8 h at ambient temperature. When the reaction was completed (monitored by TLC), water was added to the reaction mixture and the aqueous mixture was extracted with dichloromethane. The organic layer was washed with water, followed by brine solution, dried over anhydrous $Na_2SO_4$ and concentrated to afford the crude product. The crude product was purified by column chromatography (silica gel, 3% methanol in dichloromethane) to afford compound JVM 2-79 as white solid. (Yield: 65%).

$^1$H NMR ($CDCl_3$, 400 MHz): δ 6.23 (s, 1H), 5.85 (brs, 1H), 5.67 (t, J=7.2 Hz, 1H), 5.59 (s, 1H), 4.64 (d, J=12 Hz, 1H), 4.52 (d, J=11.6 Hz, 1H), 3.85 (t, J=9.6 Hz, 1H), 3.23 (brs, 2H), 3.01 (t, J=9.2 Hz, 1H), 2.89 (d, J=9.6 Hz, 1H), 2.66-2.63 (m, 2H), 2.48-2.14 (m, 8H), 1.66 (t, J=11.6 Hz, 1H), 1.55-1.48 (m, 5H), 1.32 (d, J=6 Hz, 1H), 1.11 (t, J=12 Hz, 1H). $^{13}$C NMR ($CDCl_3$, 100 MHz): δ 173.0, 171.3, 169.7, 139.0, 134.8, 130.1, 120.4, 81.3, 67.0, 63.3, 60.1, 42.7, 39.2, 36.7, 30.7, 29.4, 29.0, 25.9, 24.7, 23.9, 23.7, 18.1 ppm.

Example 21 bis(((1aR,7aS,10aS,10bS,E)-1a-Methyl-8-methylene-9-oxo-1a,2,3,6,7,7a,8,9,10a,10b-decahydrooxireno[2',3':9,10]cyclodeca[1,2-b]furan-5-yl)methyl) 4,4'-(butane-1,4-diylbis (azanediyl))bis(4-oxobutanoate) (JVM 2-86)

To the stirred solution of MMB succinate (7) (50 mg, 0.137 mmol) in dichloromethane, EDC (39.3 mg, 0.205 mmol), HOBt (27.6 mg, 0.205 mmol), triethylamine (41.5 mg, 0.411 mmol) and 1,4-diaminobutane (8.3 mg, 0.095 mmol) were added at ambient temperature. The reaction mixture was stirred for 12 h at ambient temperature. When the reaction was completed (monitored by TLC), water was added to the reaction mixture and the aqueous mixture was extracted with dichloromethane. The organic layer was washed with water, followed by brine solution, dried over anhydrous $Na_2SO_4$ and concentrated to afford the crude product. The crude product was purified by column chromatography (silica gel, 3% methanol in dichloromethane) to afford compound JVM 2-86 as white solid. (Yield: 57%).

$^1$H NMR ($CDCl_3$, 400 MHz): δ 6.23 (s, 1H), 6.05 (s, 1H), 5.65 (t, J=8 Hz, 1H), 5.58 (s, 1H), 4.62 (d, J=12.8 Hz, 1H), 4.54(d, J=13.2 Hz, 1H), 3.85(t, J=9.2 Hz, 1H), 3.30-3.09 (m, 3H), 2.90 (d, J=9.6 Hz, 1H), 2.70-2.62 (m, 2H), 2.50-2.17 (m, 8H), 1.69 (t, J=11.6 Hz, 1H), 1.54 (s, 3H), 1.50 (s, 2H), 1.13 (t, J=12.4 Hz, 1H) ppm.

Example 22

(1aR,1a'R,4E,4'E,7aS,7a'S,10aS,10bS,10a'S,
10b'S)—N,N'-(decane-1,10-diyl)bis(1a-methyl-8-
methylene-9-oxo-1a,2,3,6,7,7a,8,9,10a,10b-decahy-
drooxireno[2',3':9,10]cyclodeca[1,2-b]furan-5-
carboxamide) (JVM 3-83)

To the stirred solution of carboxylic melampomagnolic acid (3) (30 mg, 0.107 mmol) in dichloromethane, EDC (30.8 mg, 0.161 mmol), HOBt (21.75 mg, 0.161 mmol), triethylamine (32.4 mg, 0.321 mmol) and 1,10-diaminodecane (12.9 mg, 0.075 mmol) were added at ambient temperature. The reaction mixture was stirred for 3 h at ambient temperature. When the reaction was completed (monitored by TLC), water was added to the reaction mixture and the aqueous mixture was extracted with dichloromethane. The organic layer was washed with water, followed by brine solution, dried over anhydrous $Na_2SO_4$ and concentrated to afford the crude product. The crude product was purified by column chromatography (silica gel, 3% methanol in dichloromethane) to afford compound JVM 3-83 as white solid. (Yield: 65%).

$^1$H NMR (CDCl$_3$), 400 MHz): δ 6.22 (t, J=5.6 Hz, 1H), 6.18 (s, 1H), 6.12 (t, J=8.4 Hz, 1H), 5.53 (s, 1H), 3.82 (t, J=9.6 Hz, 1H), 3.501-3.45 (m, 1H), 3.19-3.13 (m, 1H), 2.92 (d, J=9.6 Hz, 1H), 2.85-2.72(m, 2H), 2.60-2.52(m, 1H), 2.40-2.19(m, 4H), 1.63-1.55(m, 4H), 1.49 (t, J=2.8 Hz, 2H), 1.25-1.15(m, 7H); $^{13}$C NMR (CDCl$_3$, 100 MHz): δ 169.8, 169.2, 139.8, 138.7, 131.4, 120.7, 81.7, 63.3, 60.1, 43.1, 39.7, 36.4, 29.5, 29.3, 29.0, 26.7, 26.0, 24.4, 24.0, 18.0 ppm.

Example 23

(1aR,1a'R,4E,4'E,7aS,7a'S,10aS,10bS,10a'S,
10b'S)—N,N'-(nonane-1,9-diyl)bis(1a-methyl-8-
methylene-9-oxo-1a,2,3,6,7,7a,8,9,10a,10b-decahy-
drooxireno[2',3':9,10]cyclodeca[1,2-b]furan-5-
carboxamide) (JVM 3-82)

To the stirred solution of melampomagnolic acid (3) (30 mg, 0.107 mmol) in dichloromethane, EDC (30.8 mg, 0.161 mmol), HOBt (21.75 mg, 0.161 mmol), triethylamine (32.4 mg, 0.321 mmol) and 1,9-diaminononane (11.9 mg, 0.075 mmol) were added at ambient temperature. The reaction mixture was stirred for 3 h at ambient temperature. When the reaction was completed (monitored by TLC), water was added to the reaction mixture and the aqueous mixture was extracted with dichloromethane. The organic layer was washed with water, followed by brine solution, dried over anhydrous $Na_2SO_4$ and concentrated to afford the crude product. The crude product was purified by column chromatography (silica gel, 3% methanol in dichloromethane) to afford compound JVM 3-82 as white solid. (Yield: 70%).

$^1$H NMR (CDCl$_3$), 400 MHz): δ 6.35 (t, J=6 Hz, 1H), 6.16 (s, 1H), 6.11 (t, J=8 Hz, 1H), 5.53(s, 1H), 3.83 (t, J=9.6 Hz, 1H), 3.53-3.46 (m, 1H), 3.13-3.06 (m, 1H), 2.99 (d, J=9.2 Hz, 1H), 2.84-2.72 (m, 2H), 2.59 (m, 1H), 2.40-2.19 (m, 4H), 1.62-1.55(m, 4H), 1.48-1.43(m, 2H), 1.23-1.13(m, 7H). $^{13}$C NMR (CDCl$_3$, 100 MHz): δ 170.0, 169.3, 139.7, 138.8, 131.5, 120.5, 81.9, 63.1, 60.0, 43.1, 39.5, 36.4, 31.0, 29.4, 28.9, 26.6, 25.9, 24.3, 24.0, 18.0 ppm.

Example 24

(1aR,1a'R,4E,4'E,7aS,7a'S,10aS,10bS,10a'S,
10b'S)—N,N'-(octane-1,8-diyl)bis(1a-methyl-8-
methylene-9-oxo-1a,2,3,6,7,7a,8,9,10a,10b-decahy-
drooxireno[2',3':9,10]cyclodeca[1,2-b]furan-5-
carboxamide) (JVM 3-78)

To the stirred solution of melampomagnolic acid (3) (30 mg, 0.107 mmol) in dichloromethane, EDC (30.8 mg, 0.161 mmol), HOBt (21.75 mg, 0.161 mmol), triethylamine (32.4 mg, 0.321 mmol) and 1,8-diaminooctane (10.8 mg, 0.075 mmol) were added at ambient temperature. The reaction mixture was stirred for 6 h at ambient temperature. When the reaction was completed (monitored by TLC), water was added to the reaction mixture and the aqueous mixture was extracted with dichloromethane. The organic layer was washed with water, followed by brine solution, dried over anhydrous $Na_2SO_4$ and concentrated to afford the crude product. The crude product was purified by column chromatography (silica gel, 3% methanol in dichloromethane) to afford compound JVM 3-78 as white solid. (Yield: 60%).

$^1$H NMR (CDCl$_3$), 400 MHz): δ 6.40 (t, J=6 Hz, 1H), 6.16 (d, J=3.2 Hz, 1H), 6.11 (t, J=8 Hz, 1H), 5.54(d, J=3.2 Hz, 1H), 3.83 (t, J=6 Hz, 1H), 3.55-3.48(m, 1H), 3.13-3.05(m, 1H), 3.02(d, J=10 Hz, 1H), 2.83-2.74 (m, 2H), 2.58-2.52(m, 1H), 2.40-2.19(m, 4H), 1.62-1.55(m, 4H), 1.48-1.47(m, 2H), 1.20-1.19(m, 5H). $^{13}$C NMR (CDCl$_3$, 100 MHz): δ 170.0, 169.3, 139.8, 138.8, 131.4, 120.5, 82.1, 63.1, 59.9, 43.3, 39.7, 36.5, 29.6, 29.5, 26.9, 25.6, 24.3, 24.0, 17.0 ppm.

Example 25

(1aR,1a'R,4E,4'E,7aS,7a'S,10aS,10bS,10a'S,
10b'S)—N,N'-(heptane-1,7-diyl)bis(1a-methyl-8-
methylene-9-oxo-1a,2,3,6,7,7a,8,9,10a,10b-decahy-
drooxireno[2',3':9,10]cyclodeca[1,2-b]furan-5-
carboxamide) (JVM 3-84)

To the stirred solution of melampomagnolic acid (3) (30 mg, 0.107 mmol) in dichloromethane, EDC (30.8 mg, 0.161 mmol), HOBt (21.75 mg, 0.161 mmol), triethylamine (32.4 mg, 0.321 mmol) and 1,7-diaminoheptane (9.75 mg, 0.075 mmol) were added at ambient temperature. The reaction mixture was stirred for 5 h at ambient temperature. When the reaction was completed (monitored by TLC), water was added to the reaction mixture and the aqueous mixture was extracted with dichloromethane. The organic layer was washed with water, followed by brine solution, dried over anhydrous $Na_2SO_4$ and concentrated to afford the crude product. The crude product was purified by column chromatography (silica gel, 3% methanol in dichloromethane) to afford compound JVM 3-84 as white solid. (Yield: 58%).

$^1$H NMR (CDCl$_3$), 400 MHz): δ 6.67 (s, 1H), 6.14-6.10 (m, 2H), 5.51(s, 1H), 3.87(t, J=9.6 Hz, 1H), 3.82-3.73(m, 1H), 3.25(d, J=9.6 Hz, 1H), 2.89-2.73(m, 3H), 2.55-2.48(m, 1H), 2.41-2.18(m, 4H), 1.59-1.55(m, 4H), 1.50-1.39(m, 2H), 1.34-1.25(m, 2H), 1.07-1.05(m, 1H), 1.00-0.94(m, 2H). $^{13}$C NMR (CDCl$_3$, 100 MHz): δ 170.9, 169.4, 139.5, 139.2, 131.2, 120.1, 82.9, 63.1, 59.8, 43.6, 39.6, 36.6, 30.3, 29.3, 28.1, 25.1, 24.2, 24.1, 17.8 ppm.

Example 26

(1aR,1a'R,4E,4'E,7aS,7a'S,10aS,10bS,10a'S, 10b'S)—N,N'-(hexane-1,6-diyl)bis(1a-methyl-8-methylene-9-oxo-1a,2,3,6,7,7a,8,9,10a,10b-decahydrooxireno[2',3':9,10]cyclodeca[1,2-b]furan-5-carboxamide) (JVM 3-86)

To the stirred solution of melampomagnolic acid (3) (30 mg, 0.107 mmol) in dichloromethane, EDC (30.8 mg, 0.161 mmol), HOBt (21.75 mg, 0.161 mmol), triethylamine (32.4 mg, 0.321 mmol) and 1,6-diaminohexane (8.70 mg, 0.075 mmol) were added at ambient temperature. The reaction mixture was stirred for 5 h at ambient temperature. When the reaction was completed (monitored by TLC), water was added to the reaction mixture and the aqueous mixture was extracted with dichloromethane. The organic layer was washed with water, followed by brine solution, dried over anhydrous Na2SO4 and concentrated to afford the crude product. The crude product was purified by column chromatography (silica gel, 3% methanol in dichloromethane) to afford compound JVM 3-86 as white solid. (Yield: 65%).

1H NMR (CDCl3), 400 MHz): δ 6.53 (d, J=7.6 Hz, 1H), 6.19-6.12(m, 2H), 5.55(s, 1H), 3.86 (t, J=10 Hz, 1H), 3.62-3.53(m, 1H), 3.13(d, J=10 Hz, 1H), 3.03-2.95 (m, 1H), 2.76-2.73(m, 2H), 2.58-2.51 (m, 1H), 2.43-2.18 (m, 4H), 1.60-1.54 (m, 4H), 1.31-1.25 (m, 3H), 1.19-1.10 (m, 2H). 13C NMR (CDCl3, 100 MHz): δ 170.7, 169.3, 139.3, 139.1, 131.6, 120.4, 82.6, 63.1, 59.8, 43.5, 38.6, 36.4, 29.9, 26.0, 25.0, 24.1, 24.1, 17.8 ppm.

Example 27

(1aR,1a'R,4E,4'E,7aS,7a'S,10aS,10bS,10a'S, 10b'S)—N,N'-(butane-1,4-diyl)bis(1a-methyl-8-methylene-9-oxo-1a,2,3,6,7,7a,8,9,1a,10b-decahydrooxireno[2',3':9,10]cyclodeca[1, 2-b]furan-5-carboxamide) (JVM 3-79)

To the stirred solution of melampomagnolic acid (3) (30 mg, 0.107 mmol) in dichloromethane, EDC (30.8 mg, 0.161 mmol), HOBt (21.75 mg, 0.161 mmol), triethylamine (32.4 mg, 0.321 mmol) and 1,4-diaminobutane (6.60 mg, 0.075 mmol) were added at ambient temperature. The reaction mixture was stirred for 6 h at ambient temperature. When the reaction was completed (monitored by TLC), water was added to the reaction mixture and the aqueous mixture was extracted with dichloromethane. The organic layer was washed with water, followed by brine solution, dried over anhydrous Na2SO4 and concentrated to afford the crude product. The crude product was purified by column chromatography (silica gel, 3% methanol in dichloromethane) to afford compound JVM 3-79 as white solid. (Yield: 55%).

1H NMR (CDCl3), 400 MHz): δ 6.89 (d, J=2.4 Hz, 1H), 6.18(s, 1H), 6.12(t, J=8.4 Hz, 1H), 5.51 (d, J=2.4 Hz, 1H), 3.83(t, J=9.6 Hz, 1H), 3.50-3.39(m, 1H), 3.28-3.17(m, 1H), 3.08(d, J=9.6 Hz, 1H), 2.84-2.72(m, 2H), 2.48-2.17(m, 5H), 1.64-1.55 (m, 5H), 1.25-1.16 (m, 2H). 13C NMR (CDCl3, 100 MHz): δ 170.0, 169.8, 139.2, 138.8, 132.4, 120.6, 81.7, 63.0, 60.0, 43.2, 39.2, 36.3, 26.5, 25.6, 24.2, 24.1, 18.0 ppm.

Example 28 bis(((1aR,7aS,10aS,10bS,E)-1a-methyl-8-methylene-9-oxo-1a,2,3,6,7,7a,8,9,10a,10b-decahydrooxireno[2',3':9,10]cyclodeca[1,2-b]furan-5-yl)methyl) glutarate (JVM 3-100)

To the MMB (2) (50 mg, 0.189 mmol) and in dichloromethane (2 mL), glutarylchloride (25.5 mg, 0.151 mmol) and triethylamine (28.6 mg, 0.283 mmol) were added at 0° C. The reaction mixture was stirred for 16 h at ambient temperature. When the reaction was completed (monitored by TLC), water was added to the reaction mixture and the aqueous mixture was extracted with dichloromethane. The organic layer was washed with water, followed by brine solution, dried over anhydrous Na2SO4 and concentrated to afford the crude product. The crude product was purified by column chromatography (silica gel, 3% methanol in dichloromethane) to afford compound JVM 3-100 as white solid. (Yield: 57%).

1H NMR (CDCl3), 400 MHz): δ 6.25 (d, J=3.6 Hz, 1H), 5.68 (t, J=7.6 Hz, 1H), 5.55(d, J=3.6 Hz, 1H), 4.65(d, J=12.4 Hz, 1H), 4.49(d, J=12.8 Hz, 1H), 3.85 (t, J=8.8 Hz, 1H), 2.94-2.88(m, 1H), 2.86 (d, J=9.6 Hz, 1H), 2.50-2.14(m, 8H), 1.99-1.91 (m, 1H), 1.71-1.67(m, 1H), 1.55(s, 3H), 1.11 (t, J=11.2 Hz, 1H). 13C NMR (CDCl3, 100 MHz): δ 172.6, 169.4, 138.9, 134.9, 130.8, 120.3, 81.1, 66.9, 63.4, 60.0, 42.8, 36.7, 33.2, 25.9, 24.7, 23.9, 20.1, 18.1 ppm.

Example 29 bis(((1aR,7aS,10aS,10bS,E)-1a-methyl-8-methylene-9-oxo-1a,2,3,6,7,7a,8,9,10a,10b-decahydrooxireno[2',3':9,10]cyclodeca[1, 2-b]furan-5-yl)methyl) malonate (JVM 3-99)

To the MMB (2) (50 mg, 0.189 mmol) and in dichloromethane (2 mL), malonyl dichloride (21.3 mg, 0.151 mmol) and triethylamine (28.6 mg, 0.283 mmol) were added at 0° C. The reaction mixture was stirred for 6 h at ambient temperature. When the reaction was completed (monitored by TLC), water was added to the reaction mixture and the aqueous mixture was extracted with dichloromethane. The organic layer was washed with water, followed by brine solution, dried over anhydrous Na2SO4 and concentrated to afford the crude product. The crude product was purified by column chromatography (silica gel, 3% methanol in dichloromethane) to afford compound JVM 3-99 as white solid. (Yield: 75%).

1H NMR (CDCl$_3$), 400 MHz): δ 6.25 (d, J=3.6 Hz, 1H), 5.72(t, J=7.6 Hz, 1H), 5.56(d, J=3.2 Hz, 1H), 4.78(d, J=12 Hz, 1H), 4.52(d, J=12.4 Hz, 1H), 3.85(t, J=9.2 Hz, 1H), 3.39(s, 1H), 3.39-2.85(m, 1H), 2.85(d, J=10 Hz, 1H), 2.51-2.15(m, 6H), 1.72-1.68(m, 1H), 1.55(s, 3H), 1.14(t, J=11.2 Hz, 1H); 13C NMR (CDCl3, 100 MHz): δ 169.4, 166.2, 138.9, 134.4, 131.8, 120.3, 81.1, 68.0, 63.4, 60.0, 42.7, 41.4, 36.7, 25.7, 24.6, 24.0, 18.1 ppm.

Example 30 butane-1,4-diylbis(((1aR,7aS,10aS,10bS,E)-1a-methyl-8-methylene-9-oxo-1a,2,3,6,7,7a,8,9,10a, 10b-decahydrooxireno[2',3':9,10]cyclodeca[1, 2-b] furan-5-yl)methyl)dicarbonate (JVM 3-91A)

To the triazole intermediate of MMB (5) (60 mg, 0.167 mmol) and in dichloromethane (2 mL), 1,4-butanediol (10.5 mg, 0.116 mmol) and triethylamine (33.7 mg, 0.334 mmol) were added at ambient temperature. The reaction mixture was stirred for 16 h at ambient temperature. When the reaction was completed (monitored by TLC), water was added to the reaction mixture and the aqueous mixture was extracted with dichloromethane. The organic layer was washed with water, followed by brine solution, dried over anhydrous Na2SO4 and concentrated to afford the crude product. The crude product was purified by column chromatography (silica gel, 3% methanol in dichloromethane) to afford compound JVM 3-91A as white solid. (Yield: 45%).

1H NMR (CDCl3, 400 MHz): δ 6.25 (d, J=3.6 Hz, 1H), 5.74 (t, J=7.6 Hz, 1H), 5.55(t, J=2.8 Hz, 1H), 4.67 (d, J=12 Hz, 1H), 4.57(d, J=12.4 Hz, 1H), 4.16(t, J=6.8 Hz, 2H), 3.85(t, J=9.2 Hz, 1H), 2.90-2.81 (m, 2H), 2.50-2.14(m, 6H), 1.76-1.66 (m, 3H), 1.55 (s, 3H), 1.12(t, J=11.6 Hz, 1H); 13C NMR (CDCl3, 100 MHz): δ 169.4, 155.1, 138.8, 134.5, 131.6, 120.4, 81.1, 70.4, 67.6, 63.4, 60.0, 42.7, 36.7, 25.8, 25.2, 24.5, 23.9, 18.1 ppm.

Example 31 bis(((1aR,7aS,10aS,10bS,E)-1a-methyl-8-methylene-9-oxo-1a,2,3,6,7,7a,8,9,10a,10b-decahydrooxireno[2',3':9,10]cyclodeca[1,2-b]furan-5-yl)methyl)pentane-1,5-diyldicarbonate (JVM 3-88A)

To the triazole intermediate of MMB (5) (60 mg, 0.167 mmol) and in dichloromethane (2 mL), 1,5-pentanediol (12.0 mg, 0.116 mmol) and triethylamine (33.7 mg, 0.334 mmol) were added at ambient temperature. The reaction mixture was stirred for 12 h at ambient temperature. When the reaction was completed (monitored by TLC), water was added to the reaction mixture and the aqueous mixture was extracted with dichloromethane. The organic layer was washed with water, followed by brine solution, dried over anhydrous Na2SO4 and concentrated to afford the crude product. The crude product was purified by column chromatography (silica gel, 3% methanol in dichloromethane) to afford compound JVM 3-88A as white solid. (Yield: 50%).

1H NMR (CDCl3, 400 MHz): δ 6.25 (d, J=3.6 Hz, 1H), 5.74 (t, J=8.4 Hz, 1H), 5.55 (d, J=2.8 Hz, 1H), 4.67 (d, J=12 Hz, 1H), 4.57 (d, J=12 Hz, 1H), 4.14 (t, J=6.8 Hz, 2H), 3.85 (t, J=9.2 Hz, 1H), 2.90-2.81 (m, 2H), 2.50-2.14 (m, 6H), 1.73-1.66 (m, 3H), 1.55 (s, 3H), 1.48-1.41 (m, 1H), 1.11 (t, J=12 Hz, 1H); 13C NMR (CDCl3, 100 MHz): δ 169.4, 155.1, 138.8, 134.5, 131.5, 120.4, 81.1, 70.3, 68.1, 63.4, 60.0, 42.7, 36.7, 28.4, 25.9, 24.5, 23.9, 22.2, 18.1 ppm.

Example 32

Synthesis of Triazole Carbonate Dimer of MMB (i.e JVM 4-18)

Provided below is the reaction scheme (Scheme 6) for a triazole carbonate dimer of MMB. An exemplary compound is JVM 4-18.

Scheme 6. Synthesis of triazole carbonate dimer of MMB

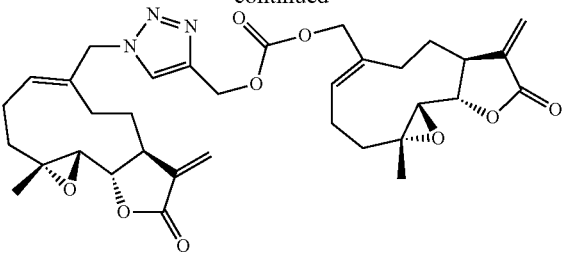

Example 33

Synthesis of Ester Dimer of MMB (PNR-09-01)

Provided below is the reaction scheme (Scheme 7) for PNR-09-01, an ester dimer of MMB. MMB was reacted with pyridine 2,6-dicarboxylic acid to afford PNR-09-01.

Scheme 7. Synthesis of pyridine 2, 6 diester dimer of MMB

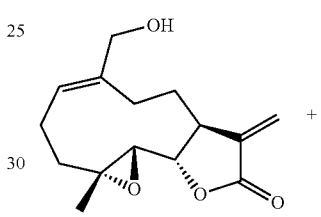

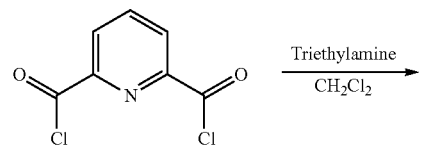

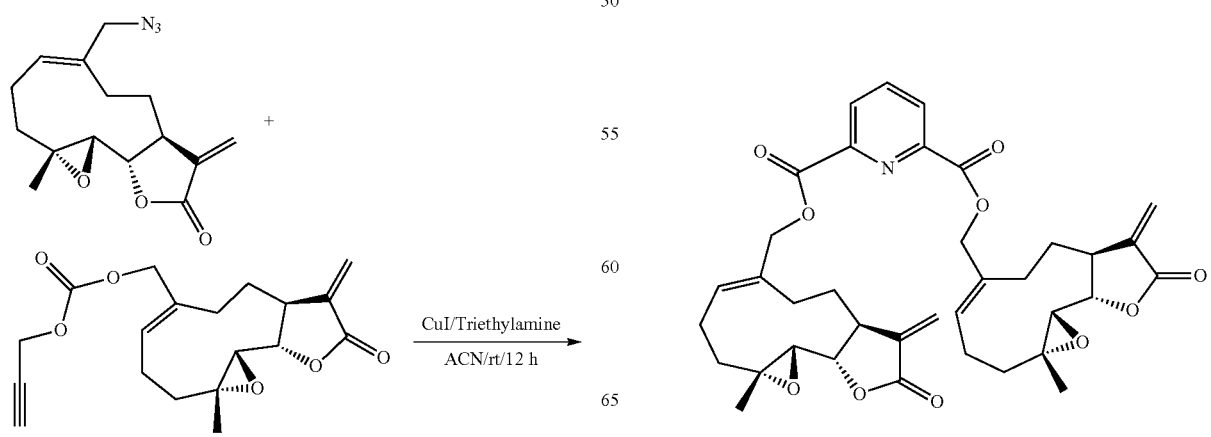

TABLE 5

Exemplary Compounds.

| Line No. | Compound Name | Compound Structure | $EC_{50}$ (μM) |
|---|---|---|---|
| 1 | JVM 3-55A | 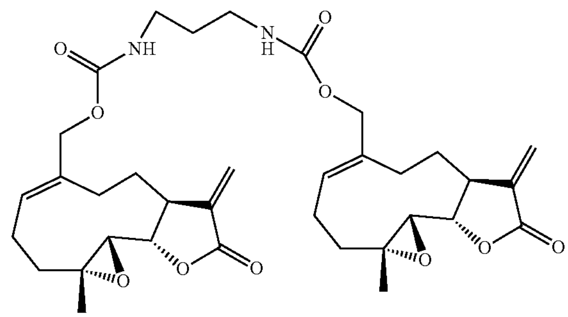 [SMILES: C=C1C(=O)O[C@H]2[C@H]1CC/C(COC(=O)NCCCNC(=O)OC/C1=C/CC[C@@]3(C)O[C@H]3[C@H]3OC(=O)C(=C)[C@@H]3CC1)=C\CC[C@@]1(C)O[C@@H]21] | — |
| 2 | JVM 3-54 | 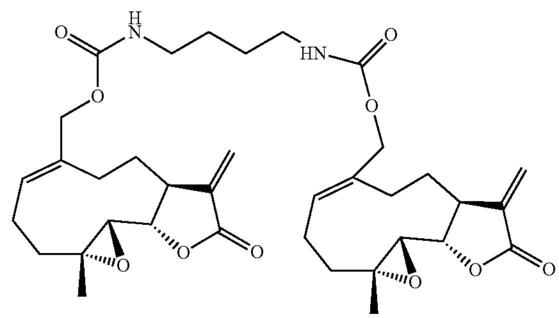 [SMILES: C=C1C(=O)O[C@H]2[C@H]1CC/C(COC(=O)NCCCCNC(=O)OC/C1=C/CC[C@@]3(C)O[C@H]3[C@H]3OC(=O)C(=C)[C@@H]3CC1)=C\CC[C@@]1(C)O[C@@H]21] | — |
| 3 | JVM 2-76 | 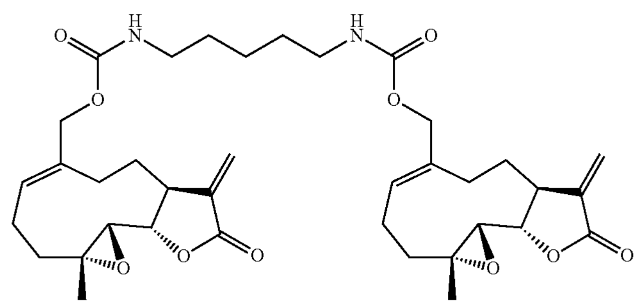 [SMILES: C=C1C(=O)O[C@H]2[C@H]1CC/C(COC(=O)NCCCCCNC(=O)OC/C1=C/CC[C@@]3(C)O[C@H]3[C@H]3OC(=O)C(=C)[C@@H]3CC1)=C\CC[C@@]1(C)O[C@@H]21] | — |
| 4 | JVM 3-64 | 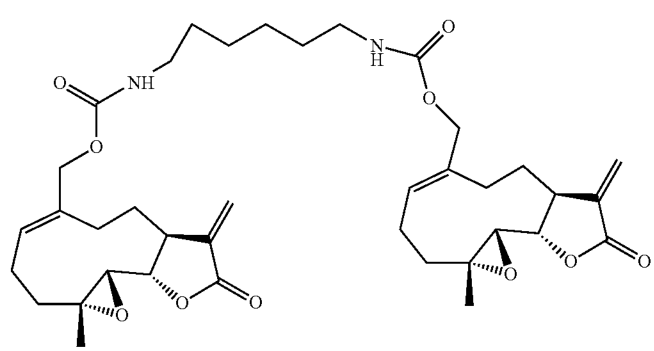 [SMILES: C=C1C(=O)O[C@H]2[C@H]1CC/C(COC(=O)NCCCCCCNC(=O)OC/C1=C/CC[C@@]3(C)O[C@H]3[C@H]3OC(=O)C(=C)[C@@H]3CC1)=C\CC[C@@]1(C)O[C@@H]21] | — |

TABLE 5-continued

Exemplary Compounds.

| Line No. | Compound Name | Compound Structure | $EC_{50}$ ($\mu M$) |
|---|---|---|---|
| 5 | JVM 3-58 | 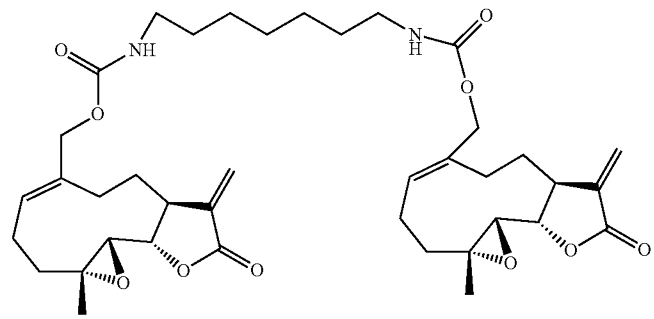 [SMILES: C=C1C(=O)O[C@H]2[C@H]1CC/C(COC(=O)NCCCCCCCNC(=O)OC/C1=C/CC[C@@]3(C)O[C@H]3[C@H]3OC(=O)C(=C)[C@@H]3CC1)=C\CC[C@@]1(C)O[C@@H]21] | — |
| 6 | JVM 3-61 | 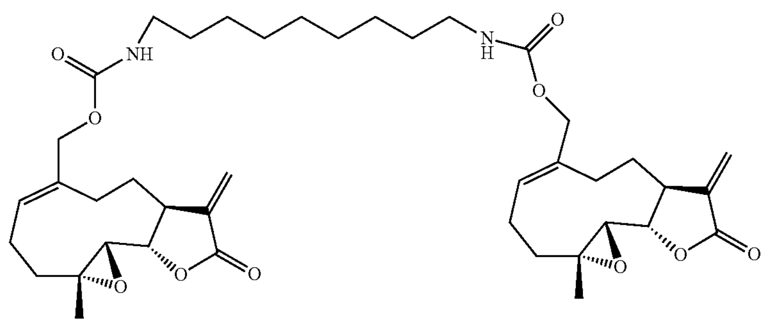 [SMILES: C=C1C(=O)O[C@H]2[C@H]1CC/C(COC(=O)NCCCCCCCCCNC(=O)OC/C1=C/CC[C@@]3(C)O[C@H]3[C@H]3OC(=O)C(=C)[C@@H]3CC1)=C\CC[C@@]1(C)O[C@@H]21] | — |
| 7 | JVM 3-62 | 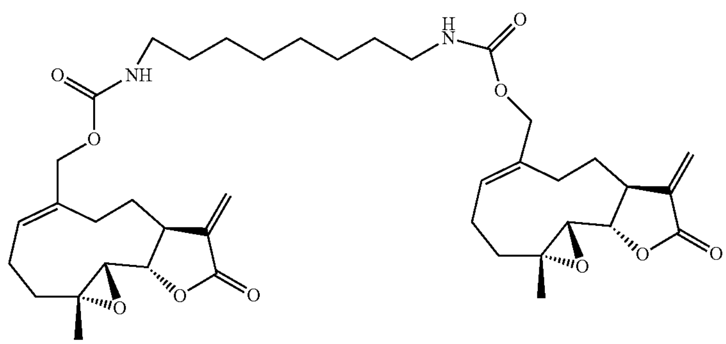 [SMILES: C=C1C(=O)O[C@H]2[C@H]1CC/C(COC(=O)NCCCCCCCCNC(=O)OC/C1=C/CC[C@@]3(C)O[C@H]3[C@H]3OC(=O)C(=C)[C@@H]3CC1)=C\CC[C@@]1(C)O[C@@H]21] | — |
| 8 | JVM 3-65 | 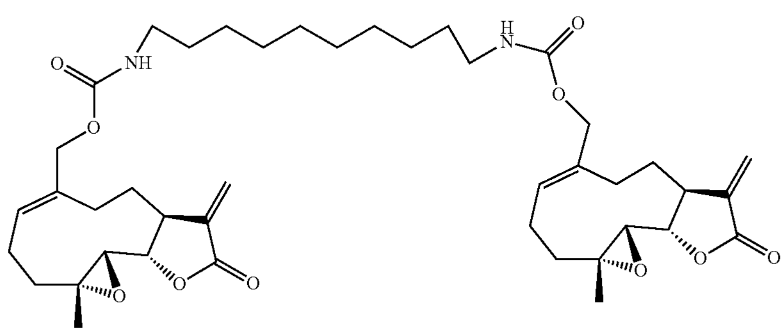 [SMILES: C=C1C(=O)O[C@H]2[C@H]1CC/C(COC(=O)NCCCCCCCCCCNC(=O)OC/C1=C/CC[C@@]3(C)O[C@H]3[C@H]3OC(=O)C(=C)[C@@H]3CC1)=C\CC[C@@]1(C)O[C@@H]21] | — |

TABLE 5-continued
Exemplary Compounds.
| Line No. | Compound Name | Compound Structure | EC$_{50}$ ($\mu$M) |
|---|---|---|---|
| 9 | JVM 3-91A | 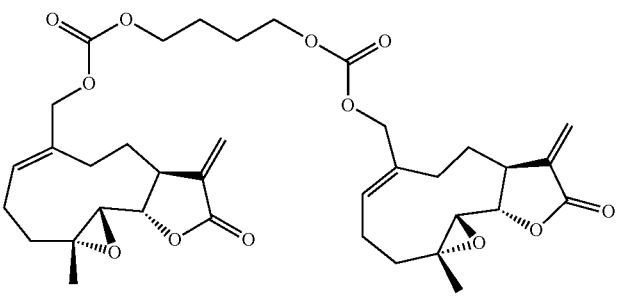 [SMILES: C=C1C(=O)O[C@H]2[C@H]1CC/C(COC(=O)OCCCCOC(=O)OC/C1=C/CC[C@@]3(C)O[C@H]3[C@H]3OC(=O)C(=C)[C@@H]3CC1)=C\CC[C@@]1(C)O[C@@H]21] | 0.93 |
| 10 | JVM 3-88A | 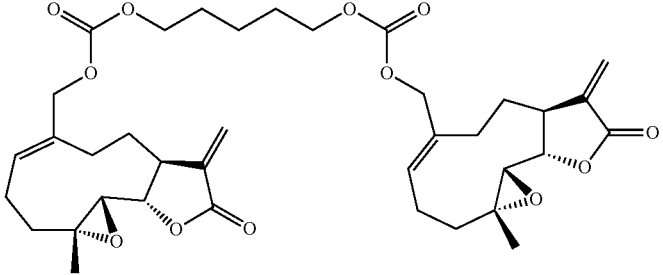 [SMILES: C=C1C(=O)O[C@H]2[C@H]1CC/C(COC(=O)OCCCCCOC(=O)OC/C1=C/CC[C@@]3(C)O[C@H]3[C@H]3OC(=O)C(=C)[C@@H]3CC1)=C\CC[C@@]1(C)O[C@@H]21] | — |
| 11 | JVM 3-55 | 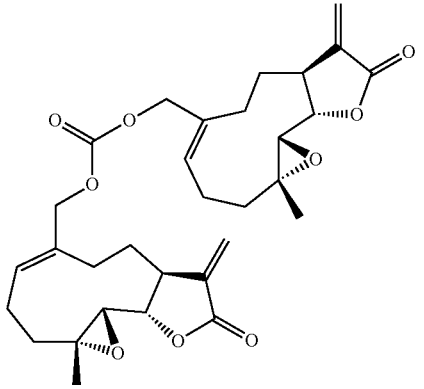 [SMILES: C=C1C(=O)O[C@H]2[C@H]1CC/C(COC(=O)OC/C1=C/CC[C@@]3(C)O[C@H]3[C@H]3OC(=O)C(=C)[C@@H]3CC1)=C\CC[C@@]1(C)O[C@@H]21] | — |
| 12 | JVM 3-68 | 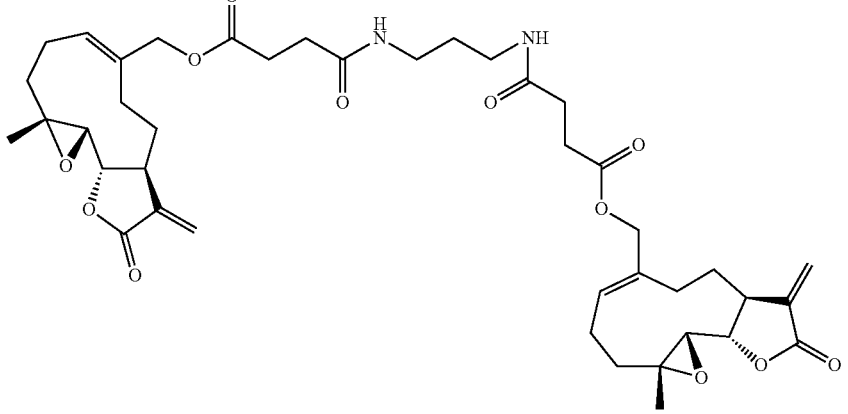 | — |

TABLE 5-continued
Exemplary Compounds.
| Line No. | Compound Name | Compound Structure | EC$_{50}$ (μM) |
|---|---|---|---|
| 13 | JVM 2-86 | 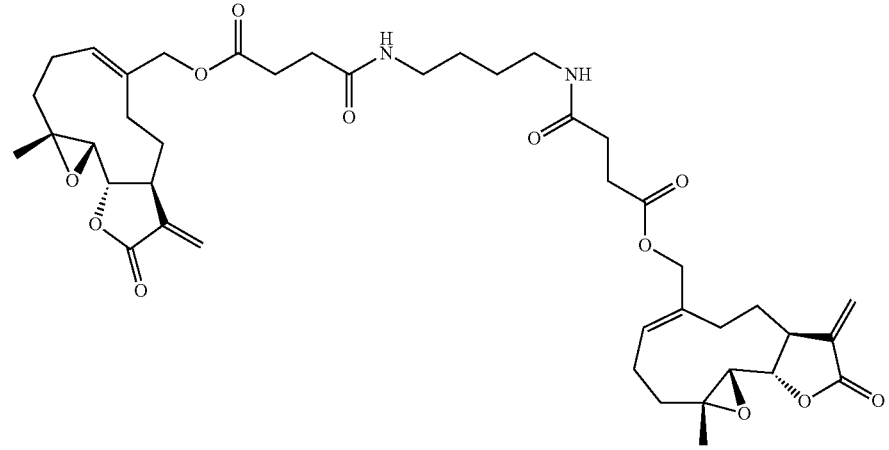 [SMILES: C=C1C(=O)O[C@H]2[C@H]1CC/C(COC(=O)CCC(=O)NCCCCNC(=O)CCC(=O)OC/C1=C/CC[C@@]3(C)O[C@H]3[C@H]3OC(=O)C(=C)[C@@H]3CC1)=C\CC[C@@]1(C)O[C@@H]21] | — |
| 14 | JVM 2-79 | 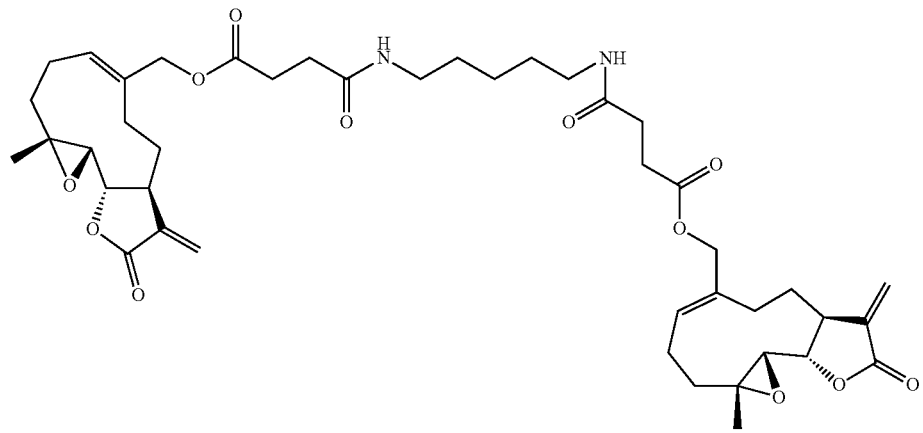 [SMILES: C=C1C(=O)O[C@H]2[C@H]1CC/C(COC(=O)CCC(=O)NCCCCCNC(=O)CCC(=O)OC/C1=C/CC[C@@]3(C)O[C@H]3[C@H]3OC(=O)C(=C)[C@@H]3CC1)=C\CC[C@@]1(C)O[C@@H]21] | — |
| 15 | JVM 2-85 | 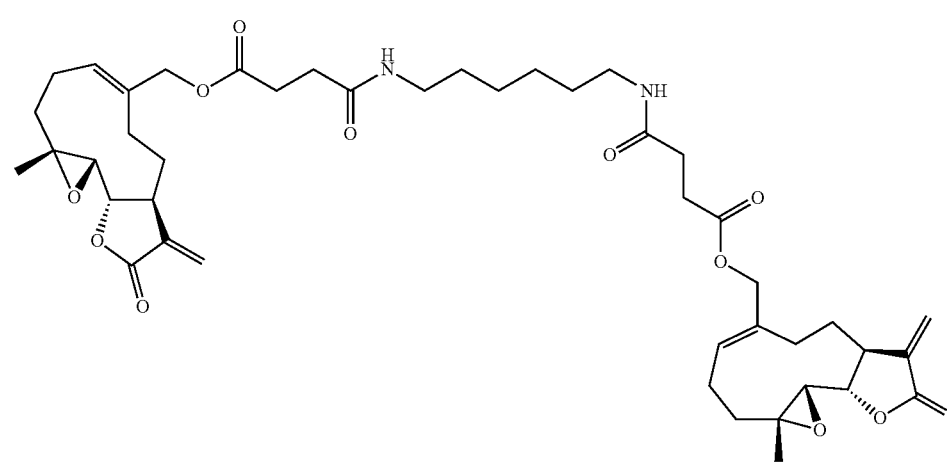 | — |

TABLE 5-continued
Exemplary Compounds.
| Line No. | Compound Name | Compound Structure | EC$_{50}$ (μM) |
|---|---|---|---|
| 16 | JVM 3-69 | 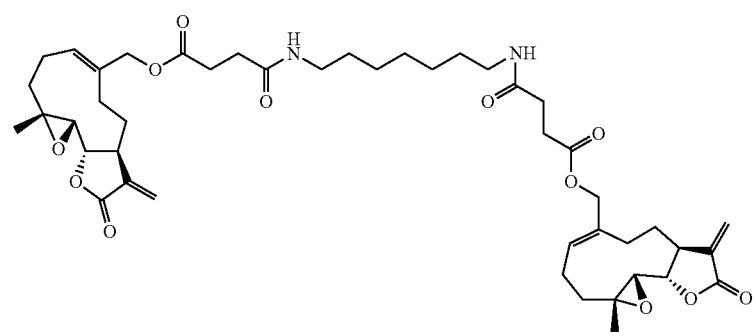 [SMILES: C=C1C(=O)O[C@H]2[C@H]1CC/C(COC(=O)CCC(=O)NCCCCCCCNC(=O)CCC(=O)OC/C1=C/CC[C@@]3(C)O[C@H]3[C@H]3OC(=O)C(=C)[C@@H]3CC1)=C\CC[C@@]1(C)O[C@@H]21] | — |
| 17 | JVM 2-87 | 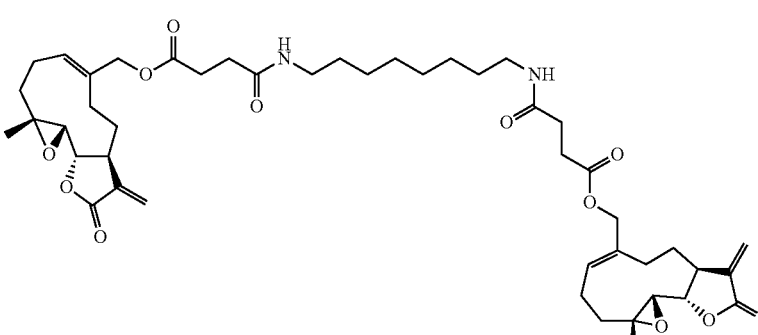 | — |
| 18 | JVM 2-92 | 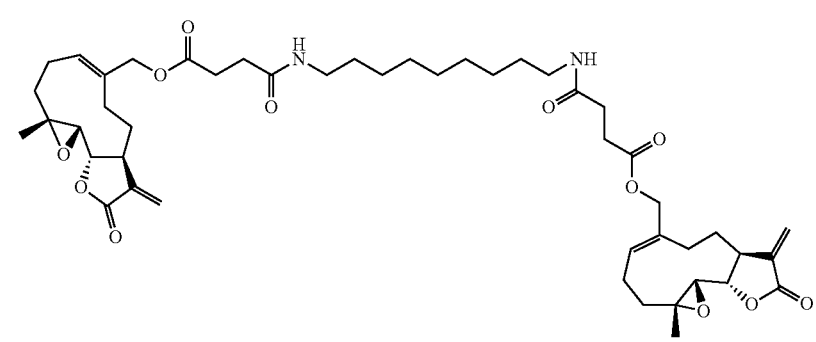 [SMILES: C=C1C(=O)O[C@H]2[C@H]1CC/C(COC(=O)CCC(=O)NCCCCCCCCCNC(=O)CCC(=O)OC/C1=C/CC[C@@]3(C)O[C@H]3[C@H]3OC(=O)C(=C)[C@@H]3CC1)=C\CC[C@@]1(C)O[C@@H]21] | — |
| 19 | JVM 3-67 | 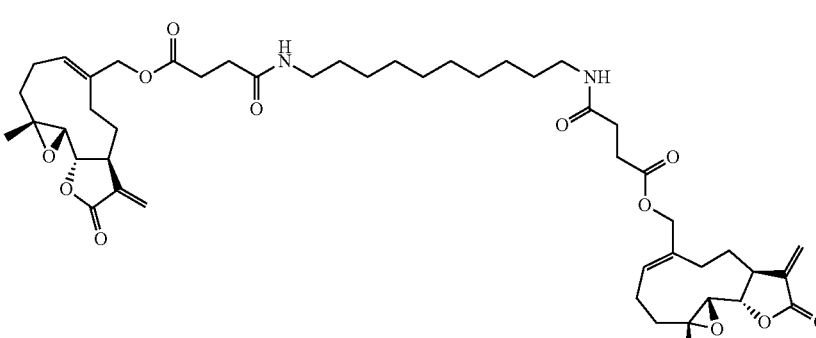 | — |

TABLE 5-continued

Exemplary Compounds.

| Line No. | Compound Name | Compound Structure | EC$_{50}$ (μM) |
|---|---|---|---|
| 20 | JVM 3-99 | 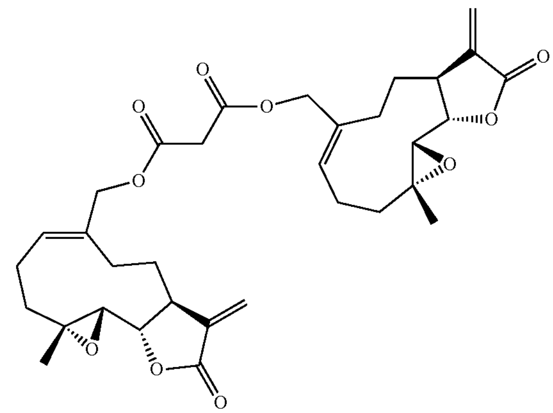 [SMILES: C=C1C(=O)O[C@H]2[C@H]1CC/C(COC(=O)CC(=O)OC/C1=C/CC[C@@]3(C)O[C@H]3[C@H]3OC(=O)C(=C)[C@@H]3CC1)=C\CC[C@@]1(C)O[C@@H]21] | 1.0 |
| 21 | JVM 3-100 | 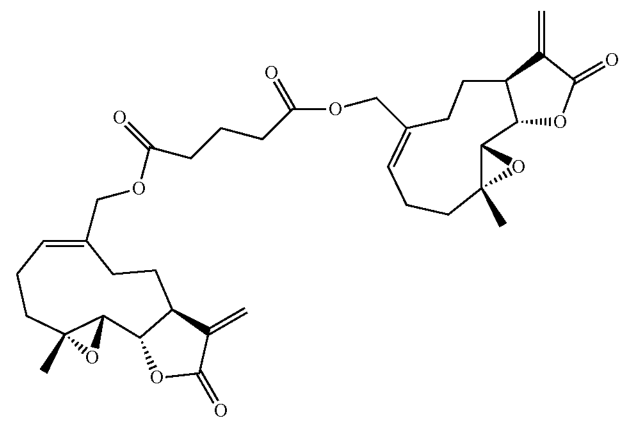 [SMILES: C=C1C(=O)O[C@H]2[C@H]1CC/C(COC(=O)CCCC(=O)OC/C1=C/CC[C@@]3(C)O[C@H]3[C@H]3OC(=O)C(=C)[C@@H]3CC1)=C\CC[C@@]1(C)O[C@@H]21] | — |
| 22 | JVM 3-79 | 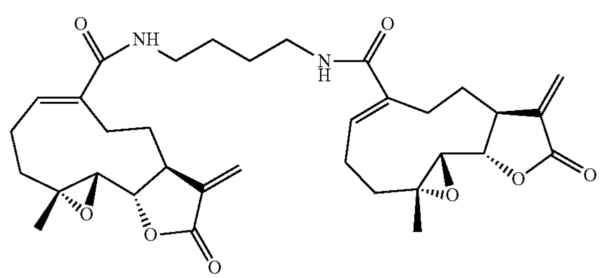 [SMILES: C=C1C(=O)O[C@H]2[C@H]1CC/C(C(=O)NCCCCNC(=O)/C1=C/CC[C@@]3(C)O[C@H]3[C@H]3OC(=O)C(=C)[C@@H]3CC1)=C\CC[C@@]1(C)O[C@@H]21] | — |
| 23 | JVM 3-86 | 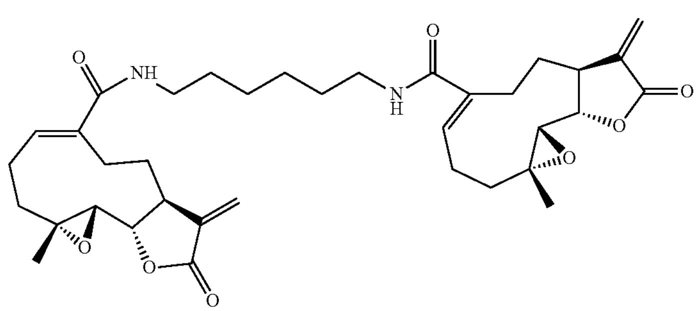 [SMILES: C=C1C(=O)O[C@H]2[C@H]1CC/C(C(=O)NCCCCCCNC(=O)/C1=C/CC[C@@]3(C)O[C@H]3[C@H]3OC(=O)C(=C)[C@@H]3CC1)=C\CC[C@@]1(C)O[C@@H]21] | — |

TABLE 5-continued
Exemplary Compounds.
| Line No. | Compound Name | Compound Structure | EC$_{50}$ (μM) |
|---|---|---|---|
| 24 | JVM 3-84 | 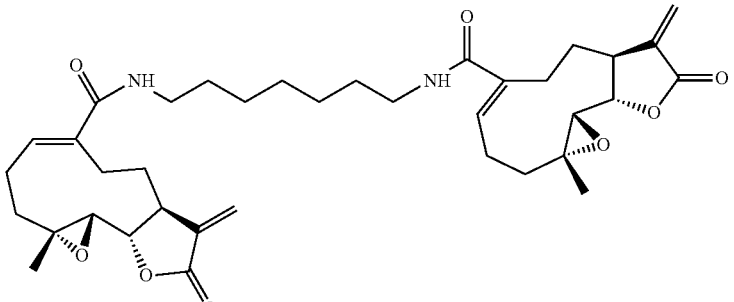 | — |
| 25 | JVM 3-78 | 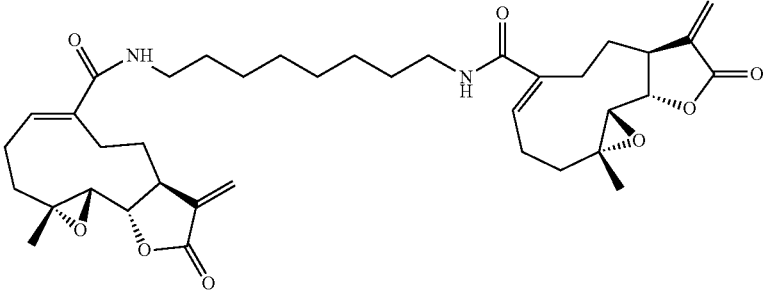 [SMILES: C=C1C(=O)O[C@H]2[C@H]1CC/C(C(=O)NCCCCCCCCNC(=O)/C1=C/CC[C@@]3(C)O[C@H]3[C@H]3OC(=O)C(=C)[C@@H]3CC1)=C\CC[C@@]1(C)O[C@@H]21] | — |
| 26 | JVM 3-82 | 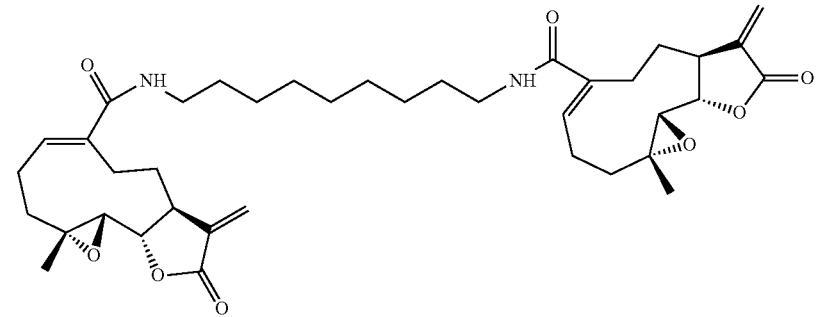 [SMILES: C=C1C(=O)O[C@H]2[C@H]1CC/C(C(=O)NCCCCCCCCCNC(=O)/C1=C/CC[C@@]3(C)O[C@H]3[C@H]3OC(=O)C(=C)[C@@H]3CC1)=C\CC[C@@]1(C)O[C@@H]21] | — |
| 27 | JVM 3-83 | 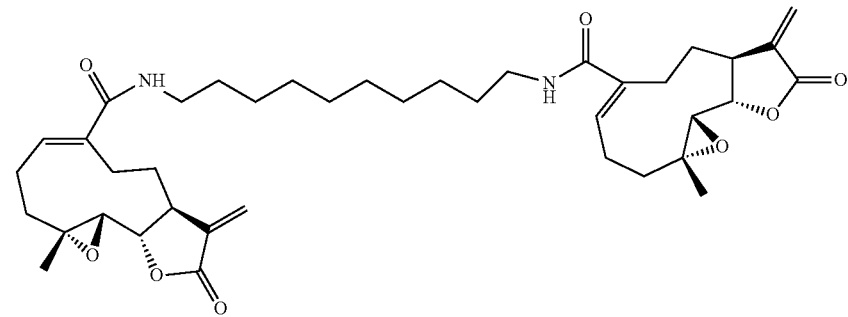 [SMILES: C=C1C(=O)O[C@H]2[C@H]1CC/C(C(=O)NCCCCCCCCCCNC(=O)/C1=C/CC[C@@]3(C)O[C@H]3[C@H]3OC(=O)C(=C)[C@@H]3CC1)=C\CC[C@@]1(C)O[C@@H]21] | 2.8 |
| 28 | JVM 4-18 | 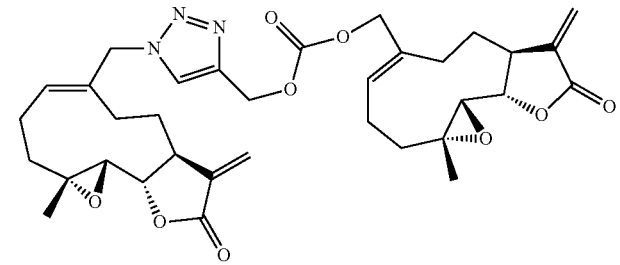 [SMILES: C=C1C(=O)O[C@H]2[C@H]1CC/C(COC(=O)OCc1cn(C/C3=C/CC[C@@]4(C)O[C@H]4[C@H]4OC(=O)C(=C)[C@@H]4CC3)nn1)=C\CC[C@@]1(C)O[C@@H]21] | — |

TABLE 5-continued
Exemplary Compounds.
| Line No. | Compound Name | Compound Structure | EC$_{50}$ (μM) |
|---|---|---|---|
| 29 | PNR-9-01 | 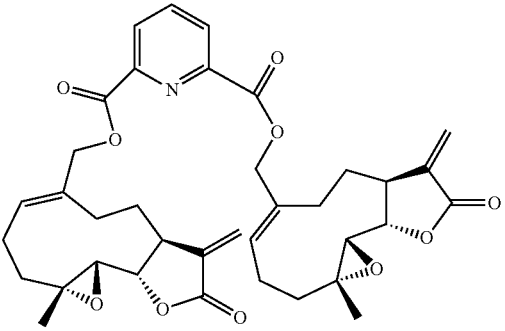 [SMILES: C=C1C(=O)O[C@H]2[C@H]1CC/C(COC(=O)c1cccc(C(=O)OC/C3=C/CC[C@@]4(C)O[C@H]4[C@H]4OC(=O)C(=C)[C@@H]4CC3)n1)=C\CC[C@@]1(C)O[C@@H]21] | — |
| 30 | JVM 4-44 | 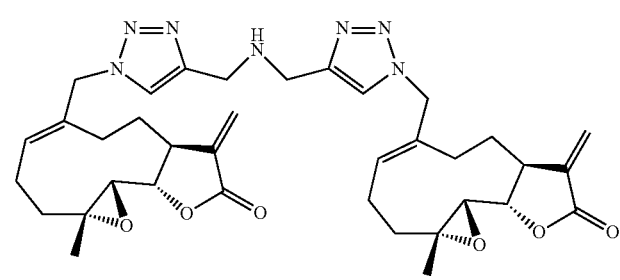 [SMILES: C=C1C(=O)O[C@H]2[C@H]1CC/C(Cn1cc(CNCc3cn(C/C4=C/CC[C@@]5(C)O[C@H]5[C@H]5OC(=O)C(=C)[C@@H]5CC4)nn3)nn1)=C\CC[C@@]1(C)O[C@@H]21] | 51.6 |
| 31 | JVM 4-51 | 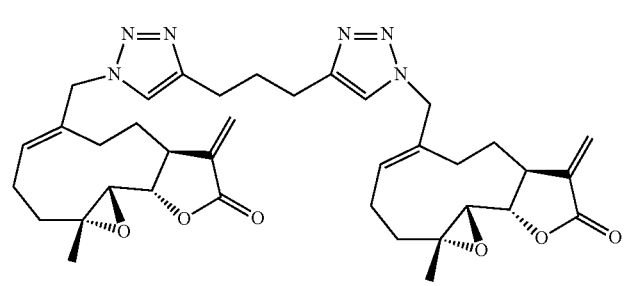 [SMILES: C=C1C(=O)O[C@H]2[C@H]1CC/C(Cn1cc(CCCc3cn(C/C4=C/CC[C@@]5(C)O[C@H]5[C@H]5OC(=O)C(=C)[C@@H]5CC4)nn3)nn1)=C\CC[C@@]1(C)O[C@@H]21] | 4.0 |
| 32 | JVM 4-41A | 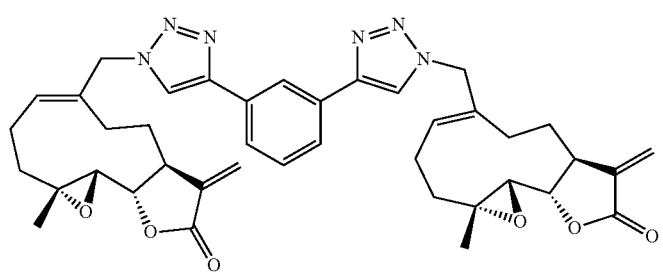 [SMILES: C=C1C(=O)O[C@H]2[C@H]1CC/C(Cn1cc(-c3cccc(-c4cn(C/C5=C/CC[C@@]6(C)O[C@H]6[C@H]6OC(=O)C(=C)[C@@H]6CC5)nn4)c3)nn1)=C\CC[C@@]1(C)O[C@@H]21] | 2.3 |

TABLE 5-continued
Exemplary Compounds.
| Line No. | Compound Name | Compound Structure | EC$_{50}$ (μM) |
|---|---|---|---|
| 33 | JVM 3-62-1 | 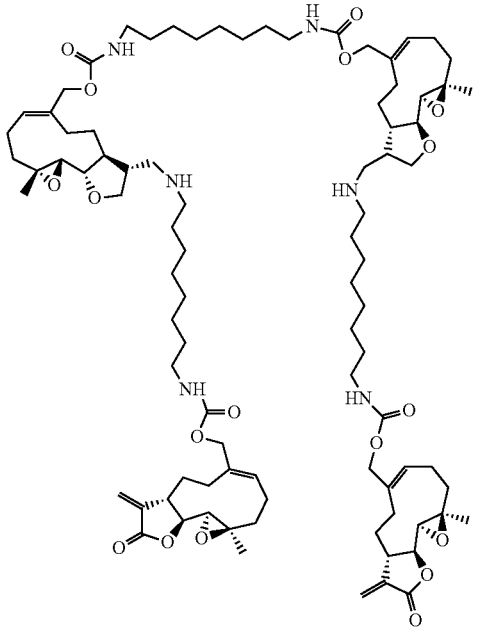 | 1.7 |
| 34 | JVM 3-62-2 | 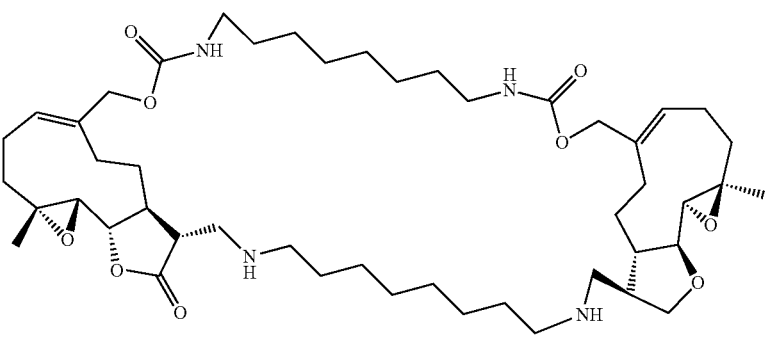 [SMILES: C[C@@]12CC/C=C3\CC[C@@H]4[C@H](OC(=O)[C@H]4CNCCCCCCCCNC[C@@H]4CO[C@H]5[C@H]4CC/C(=C\CC[C@@]4(C)O[C@@H]54)COC(=O)NCCCCCCCCNC(=O)OC3)[C@@H]1O2] | 38.05 |
| 35 | JVM 3-55 C | 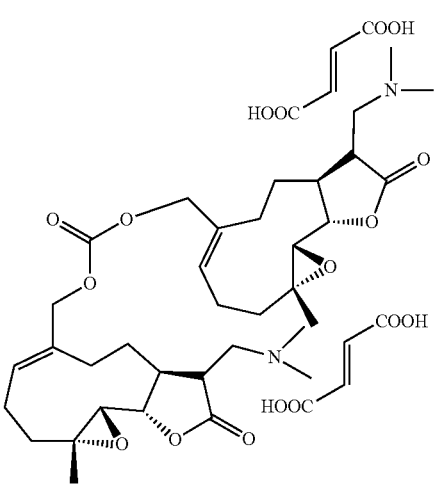 | — |

TABLE 5-continued

Exemplary Compounds.

| Line No. | Compound Name | Compound Structure | EC$_{50}$ (μM) |
|---|---|---|---|
| 36 | JVM 3-55 B | 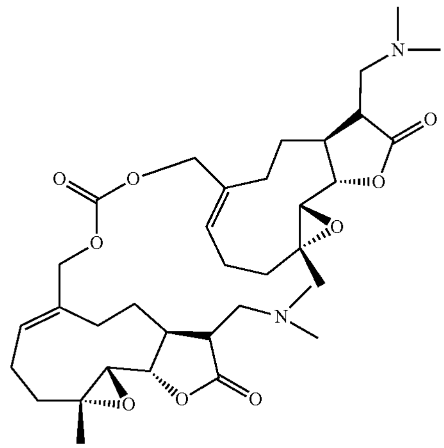 | 5.1 |
| 37 | JVM 3-62A | 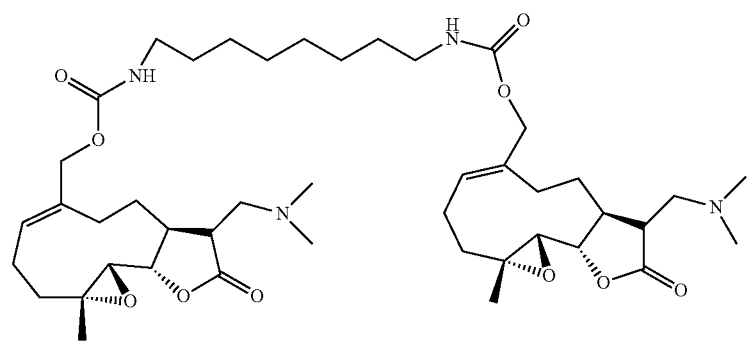 | 1.3 |
| 38 | JVM 3-62B | 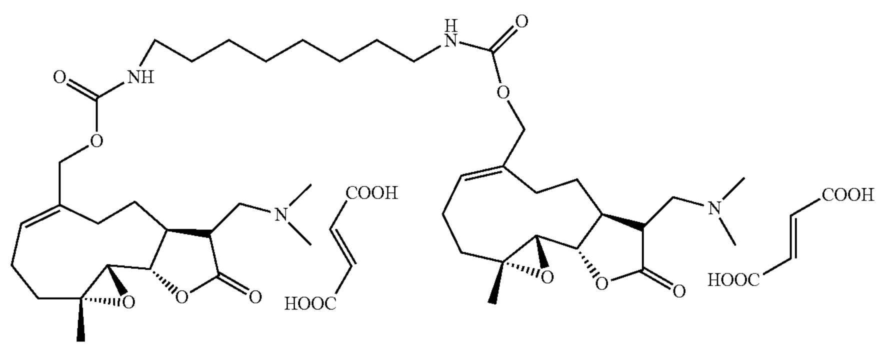 | 1.2 |
| 39 | BS-3-24 | 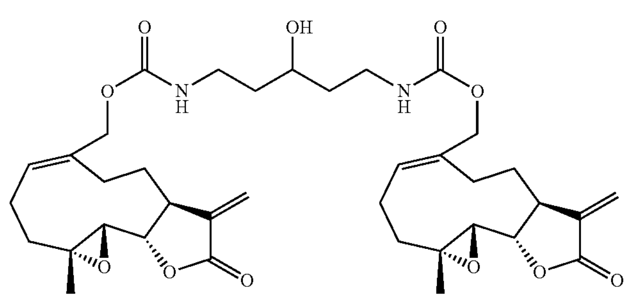 [SMILES: C=C1C(=O)O[C@H]2[C@H]1CC/C(COC(=O)NCCC(O)CCNC(=O)OC/C1=C/CC[C@@]3(C)O[C@H]3[C@H]3OC(=O)C(=C)[C@@H]3CC1)=C\CC[C@@]1(C)O[C@@H]21] | 9.03 |

TABLE 5-continued

Exemplary Compounds.

| Line No. | Compound Name | Compound Structure | $EC_{50}$ (μM) |
|---|---|---|---|
| 40 | BS-3-14 | 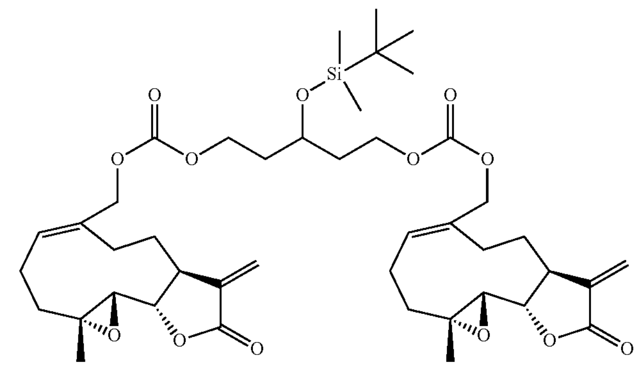 [SMILES: C=C1C(=O)O[C@H]2[C@H]1CC/C(COC(=O)OCCC(CCOC(=O)OC/C1=C/CC[C@@]3(C)O[C@H]3[C@H]3OC(=O)C(=C)[C@@H]3CC1)O[Si](C)(C)C(C)(C)C)=C\CC[C@@]1(C)O[C@@H]21] | 1.11 |
| 41 | BS-4-70 | 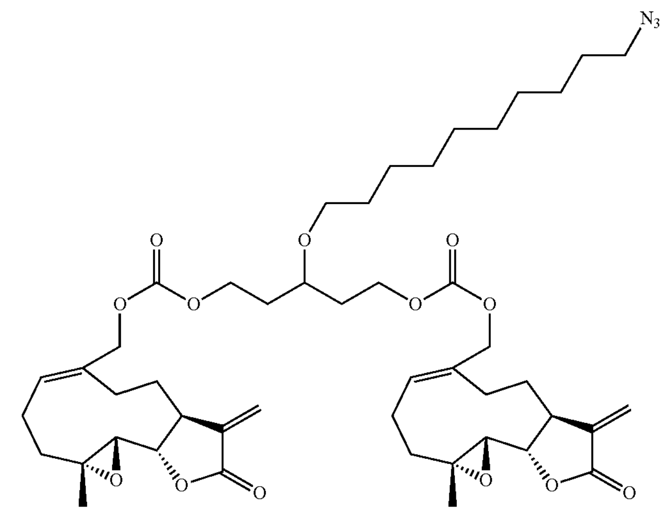 [SMILES: C=C1C(=O)O[C@H]2[C@H]1CC/C(COC(=O)OCCC(CCOC(=O)OC/C1=C/CC[C@@]3(C)O[C@H]3[C@H]3OC(=O)C(=C)[C@@H]3CC1)OCCCCCCCCCCN=[N+]=[N-])=C\CC[C@@]1(C)O[C@@H]21] | NA |
| 42 | BS-4-38a | 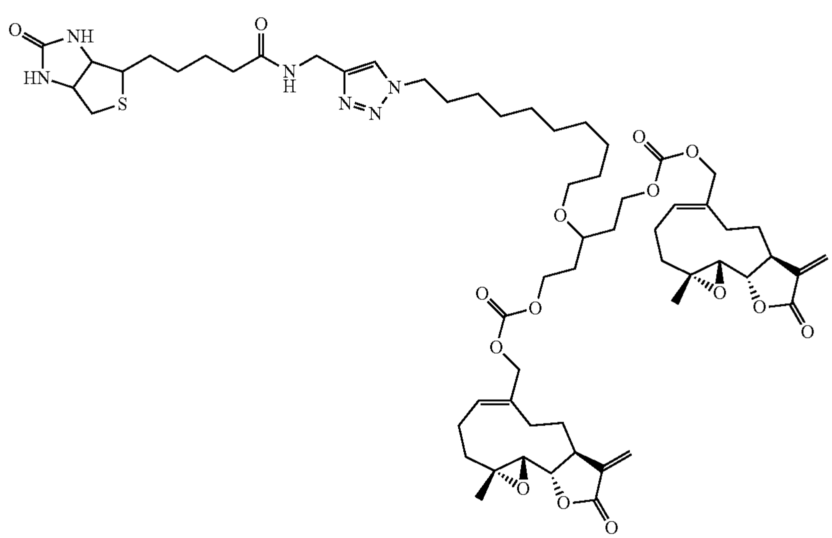 [SMILES: C=C1C(=O)O[C@H]2[C@H]1CC/C(COC(=O)OCCC(CCOC(=O)OC/C1=C/CC[C@@]3(C)O[C@H]3[C@H]3OC(=O)C(=C)[C@@H]3CC1)OCCCCCCCCCCn1cc(CNC(=O)CCCCC3SCC4NC(=O)NC43)nn1)=C\CC[C@@]1(C)O[C@@H]21] | 20.0 |

TABLE 5-continued

Exemplary Compounds.

| Line No. | Compound Name | Compound Structure | EC$_{50}$ (μM) |
|---|---|---|---|
| 43 | BS-4-38b | 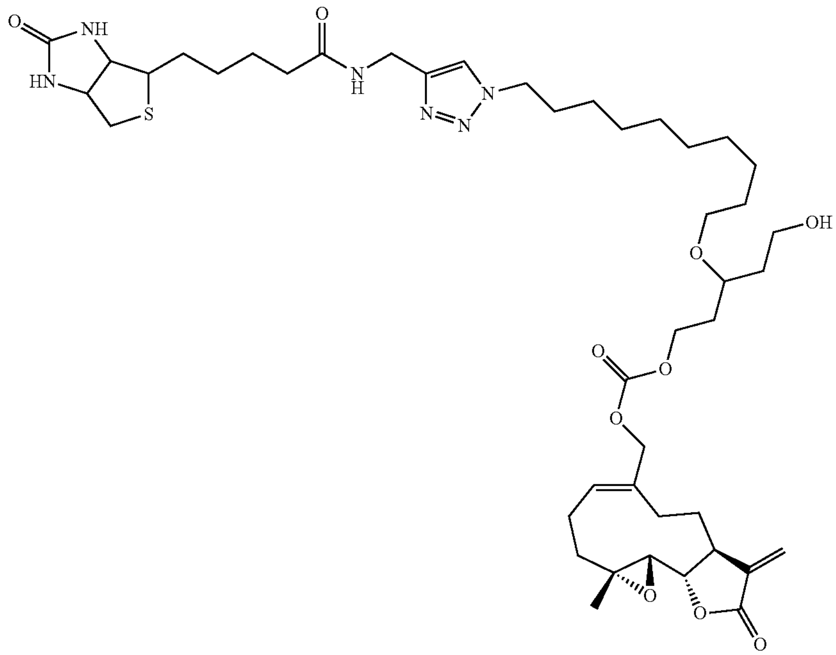 [SMILES: C=C1C(=O)O[C@H]2[C@H]1CC/C(COC(=O)OCCC(CCO)OCCCCCCCCCCn1cc(CNC(=O)CCCCC3SCC4NC(=O)NC43)nn1)=C\CC[C@@]1(C)O[C@@H]21] | 30.0 |
| 44 | | 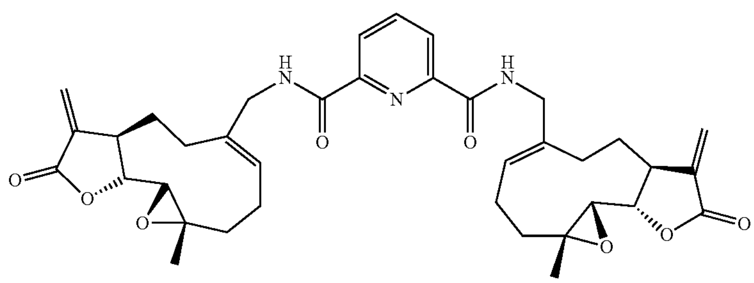 | — |
| 45 | | 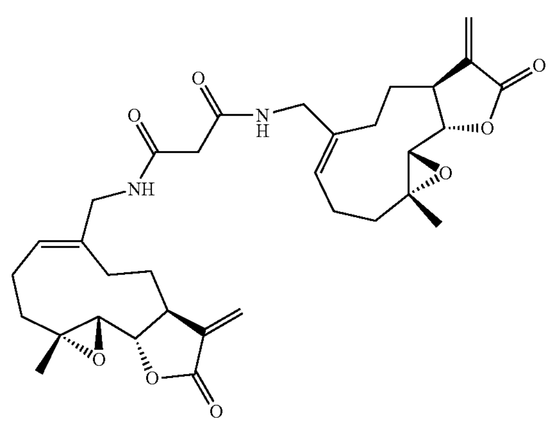 [SMILES: C=C1C(=O)O[C@H]2[C@H]1CC/C(CNC(=O)CC(=O)NC/C1=C/CC[C@@]3(C)O[C@H]3[C@H]3OC(=O)C(=C)[C@@H]3CC1)=C\CC[C@@]1(C)O[C@@H]21] | — |

TABLE 5-continued

Exemplary Compounds.

| Line No. | Compound Name | Compound Structure | $EC_{50}$ (μM) |
|---|---|---|---|
| 46 | | 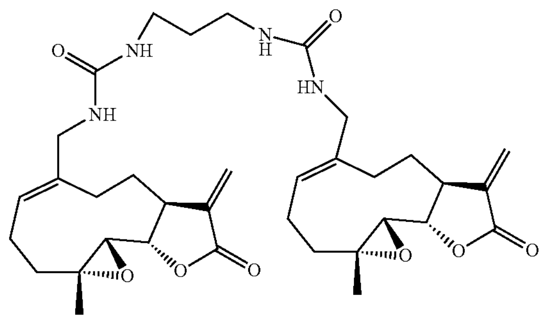 [SMILES: C=C1C(=O)O[C@H]2[C@H]1CC/C(CNC(=O)NCCCNC(=O)NC/C1=C/CC[C@@]3(C)O[C@H]3[C@H]3OC(=O)C(=C)[C@@H]3CC1)=C\CC[C@@]1(C)O[C@@H]21] | — |
| 47 | | 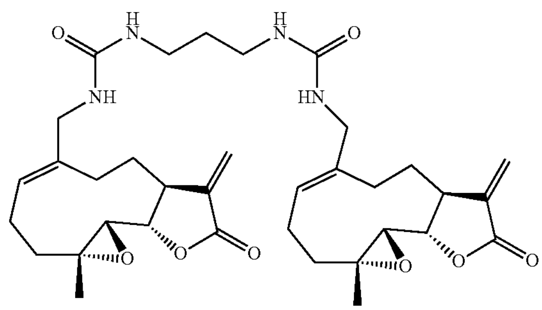 [SMILES: C=C1C(=O)O[C@H]2[C@H]1CC/C(CNC(=O)NCCCNC(=O)NC/C1=C/CC[C@@]3(C)O[C@H]3[C@H]3OC(=O)C(=C)[C@@H]3CC1)=C\CC[C@@]1(C)O[C@@H]21] | — |
| 48 | | 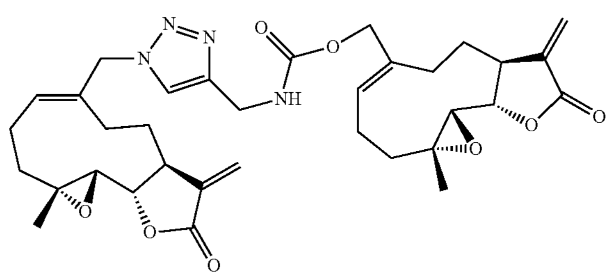 [SMILES: C=C1C(=O)O[C@H]2[C@H]1CC/C(COC(=O)NCc1cn(C/C3=C/CC[C@@]4(C)O[C@H]4[C@H]4OC(=O)C(=C)[C@@H]4CC3)nn1)=C\CC[C@@]1(C)O[C@@H]21] | — |
| 49 | | 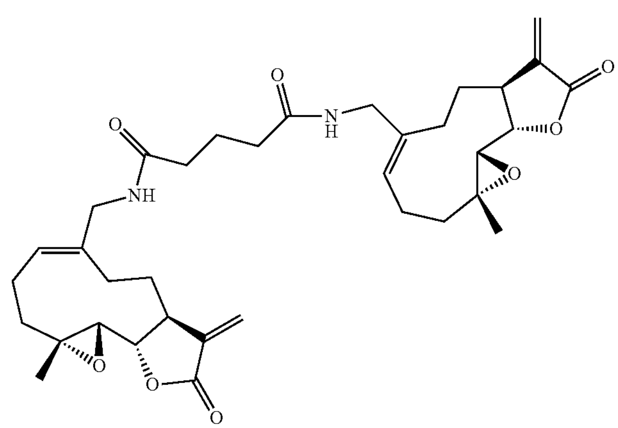 [SMILES: C=C1C(=O)O[C@H]2[C@H]1CC/C(CNC(=O)CCCC(=O)NC/C1=C/CC[C@@]3(C)O[C@H]3[C@H]3OC(=O)C(=C)[C@@H]3CC1)=C\CC[C@@]1(C)O[C@@H]21] | — |

TABLE 5-continued
Exemplary Compounds.
| Line No. | Compound Name | Compound Structure | EC$_{50}$ (μM) |
|---|---|---|---|
| 50 | | 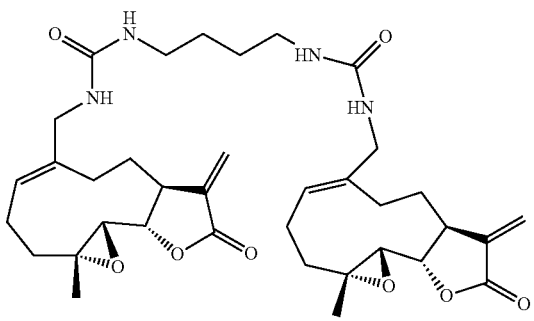 [SMILES: C=C1C(=O)O[C@H]2[C@H]1CC/C(CNC(=O)NCCCCNC(=O)NC/C1=C/CC[C@@]3(C)O[C@H]3[C@H]3OC(=O)C(=C)[C@@H]3CC1)=C\CC[C@@]1(C)O[C@@H]21] | — |
| 51 | | 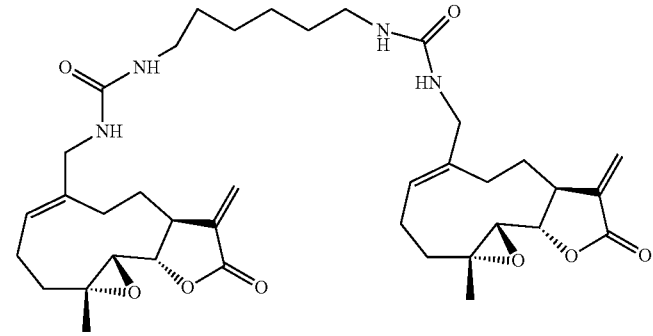 [SMILES: C=C1C(=O)O[C@H]2[C@H]1CC/C(CNC(=O)NCCCCCCNC(=O)NC/C1=C/CC[C@@]3(C)O[C@H]3[C@H]3OC(=O)C(=C)[C@@H]3CC1)=C\CC[C@@]1(C)O[C@@H]21] | — |
| 52 | | 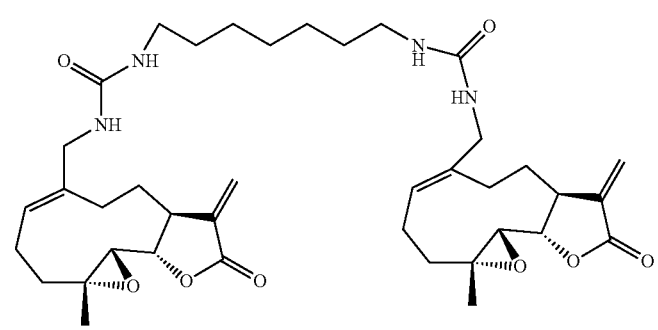 [SMILES: C=C1C(=O)O[C@H]2[C@H]1CC/C(CNC(=O)NCCCCCCCNC(=O)NC/C1=C/CC[C@@]3(C)O[C@H]3[C@H]3OC(=O)C(=C)[C@@H]3CC1)=C\CC[C@@]1(C)O[C@@H]21] | — |
| 53 | | 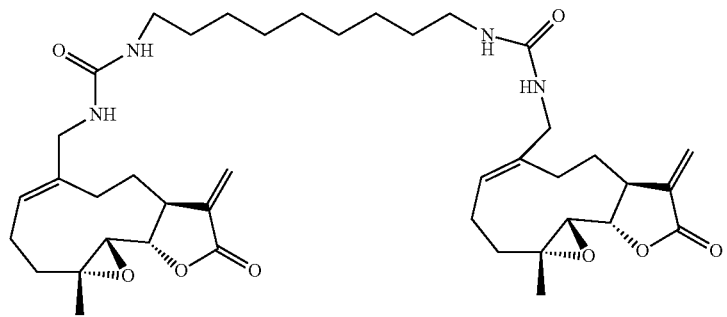 [SMILES: C=C1C(=O)O[C@H]2[C@H]1CC/C(CNC(=O)NCCCCCCCCCNC(=O)NC/C1=C/CC[C@@]3(C)O[C@H]3[C@H]3OC(=O)C(=C)[C@@H]3CC1)=C\CC[C@@]1(C)O[C@@H]21] | — |

TABLE 5-continued

Exemplary Compounds.

| Line No. | Compound Name | Compound Structure | EC$_{50}$ (μM) |
|---|---|---|---|
| 54 | | 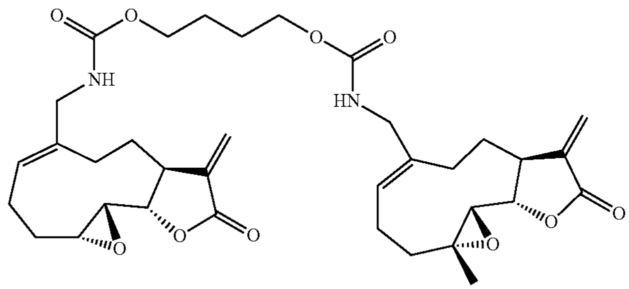 [SMILES: C=C1C(=O)O[C@@H]2[C@@H]3O[C@@H]3CC/C=C(/CNC(=O)OCCCCOC(=O)NC/C3=C/CC[C@@]4(C)O[C@H]4[C@H]4OC(=O)C(=C)[C@@H]4CC3)CC[C@@H]12] | — |
| 55 | | 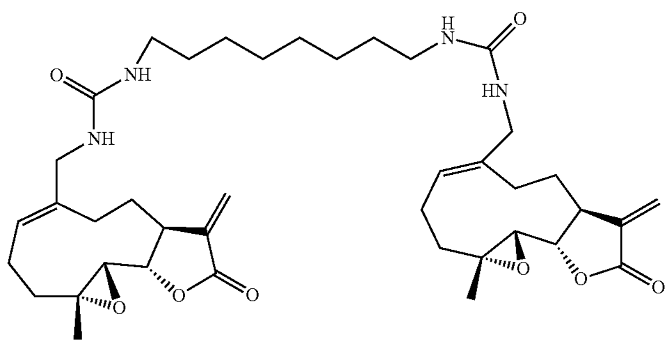 [SMILES: C=C1C(=O)O[C@H]2[C@H]1CC/C(CNC(=O)NCCCCCCCCNC(=O)NC/C1=C/CC[C@@]3(C)O[C@H]3[C@H]3OC(=O)C(=C)[C@@H]3CC1)=C\CC[C@@]1(C)O[C@@H]21] | — |
| 56 | | 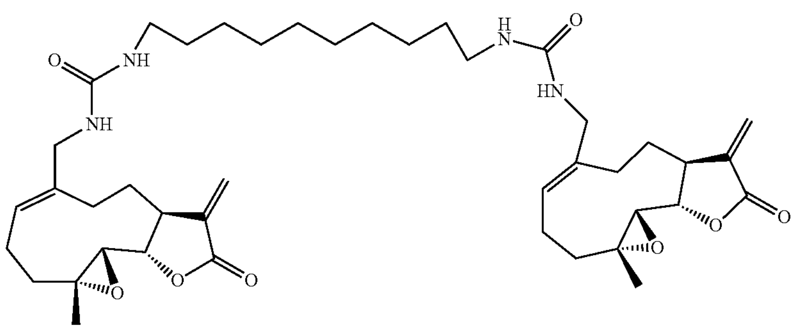 [SMILES: C=C1C(=O)O[C@H]2[C@H]1CC/C(CNC(=O)NCCCCCCCCCCNC(=O)NC/C1=C/CC[C@@]3(C)O[C@H]3[C@H]3OC(=O)C(=C)[C@@H]3CC1)=C\CC[C@@]1(C)O[C@@H]21] | — |
| 57 | | 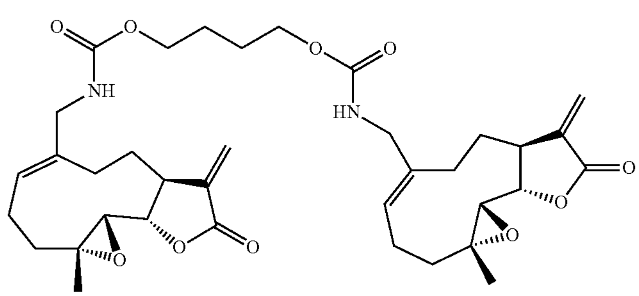 [SMILES: C=C1C(=O)O[C@H]2[C@H]1CC/C(CNC(=O)OCCCCOC(=O)NC/C1=C/CC[C@@]3(C)O[C@H]3[C@H]3OC(=O)C(=C)[C@@H]3CC1)=C\CC[C@@]1(C)O[C@@H]21] | — |

TABLE 5-continued
Exemplary Compounds.
| Line No. | Compound Name | Compound Structure | $EC_{50}$ (μM) |
|---|---|---|---|
| 58 | JVM 3-90 | 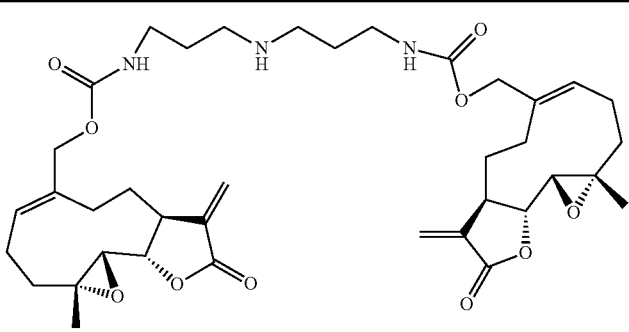 | — |
| 59 | | 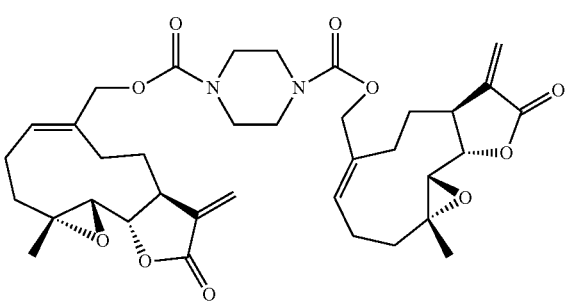 [SMILES: C=C1C(=O)O[C@H]2[C@H]1CC/C(COC(=O)N1CCN(C(=O)OC/C3=C/CC[C@@]4(C)O[C@H]4[C@H]4OC(=O)C(=C)[C@@H]4CC3)CC1)=C\CC[C@@]1(C)O[C@@H]21] | — |
| 60 | | 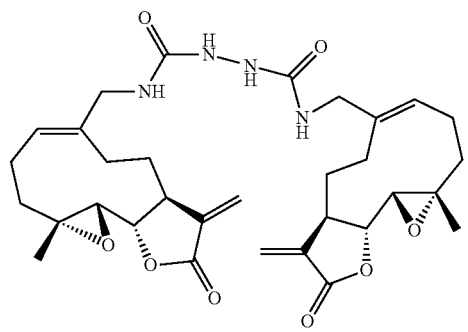 [SMILES: C=C1C(=O)O[C@@H]2[C@@H]1CC/C(CNC(=O)NNC(=O)NC/C1=C/CC[C@@]3(C)O[C@H]3[C@H]3OC(=O)C(=C)[C@@H]3CC1)=C\CC[C@]1(C)O[C@H]21] | — |
| 61 | JVM 3-70 | 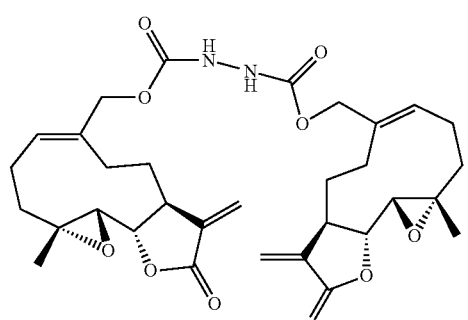 | — |

TABLE 5-continued

Exemplary Compounds.

| Line No. | Compound Name | Compound Structure | $EC_{50}$ (µM) |
|---|---|---|---|
| 62 | | 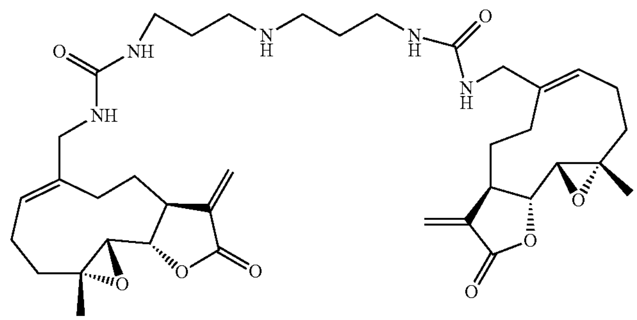 [SMILES: C=C1C(=O)O[C@@H]2[C@@H]1CC/C(CNC(=O)NCCCNCCCNC(=O)NC/C1=C/CC[C@@]3(C)O[C@H]3[C@H]3OC(=O)C(=C)[C@@H]3CC1)=C\CC[C@]1(C)O[C@H]21] | — |
| 63 | | 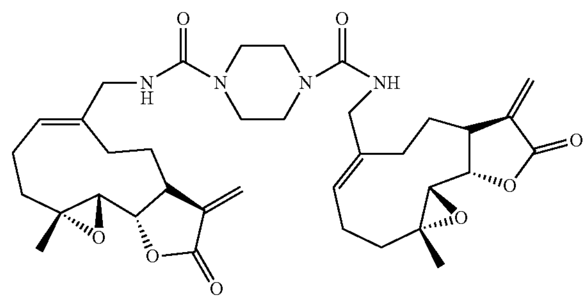 | — |
| 64 | | 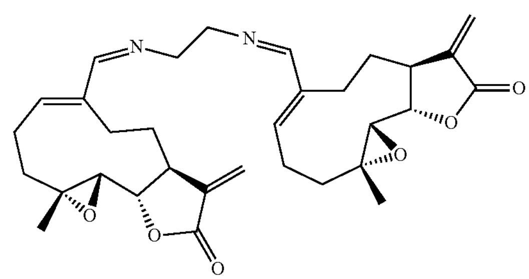 [SMILES: C=C1C(=O)O[C@H]2[C@H]1CC/C(C=NCC/N=C\C1=C\CC[C@@]3(C)O[C@H]3[C@H]3OC(=O)C(=C)[C@@H]3CC1)=C\CC[C@@]1(C)O[C@@H]21] | — |
| 65 | | 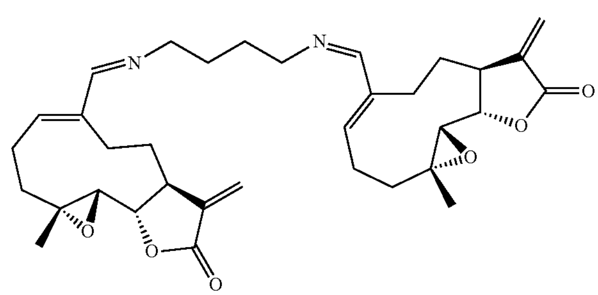 [SMILES: C=C1C(=O)O[C@H]2[C@H]1CCC(/C=N\CCCC/N=C/C1=C/CC[C@@]3(C)O[C@H]3[C@H]3OC(=O)C(=C)[C@@H]3CC1)=C\CC[C@@]1(C)O[C@@H]21] | — |
| 66 | | 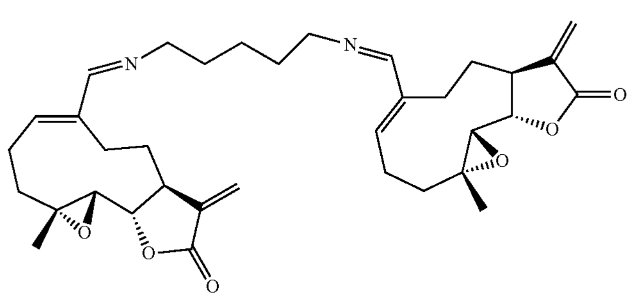 [SMILES: C=C1C(=O)O[C@H]2[C@H]1CC/C(C=NCCCCC/N=C/C1=C/CC[C@@]3(C)O[C@H]3[C@H]3OC(=O)C(=C)[C@@H]3CC1)=C\CC[C@@]1(C)O[C@@H]21] | — |

TABLE 5-continued

Exemplary Compounds.

| Line No. | Compound Name | Compound Structure | EC$_{50}$ (µM) |
|---|---|---|---|
| 67 | | 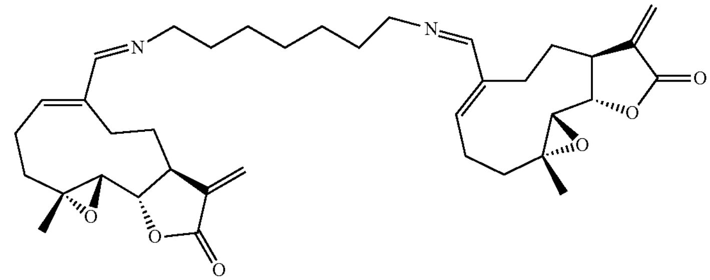 [SMILES: C=C1C(=O)O[C@H]2[C@H]1CC/C(C=NCCCCCCC/N=C/C1=C/CC[C@@]3(C)O[C@H]3[C@H]3OC(=O)C(=C)[C@@H]3CC1)=C\CC[C@@]1(C)O[C@@H]21] | — |
| 68 | | 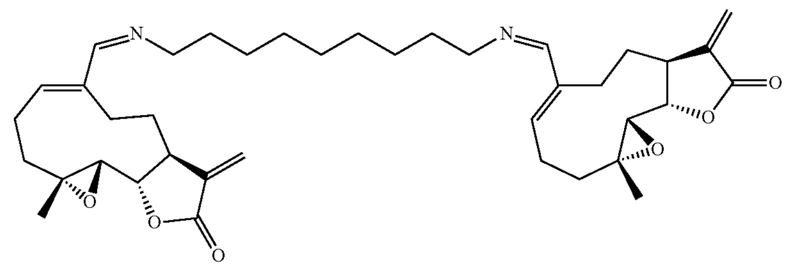 [SMILES: C=C1C(=O)O[C@H]2[C@H]1CCC(/C=N\CCCCCCCCC/N=C\C1=C\CC[C@@]3(C)O[C@H]3[C@H]3OC(=O)C(=C)[C@@H]3CC1)=C\CC[C@@]1(C)O[C@@H]21] | — |
| 69 | | 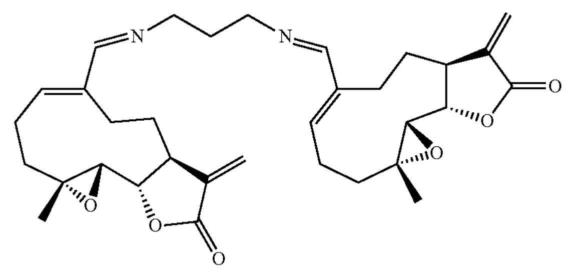 [SMILES: C=C1C(=O)O[C@H]2[C@H]1CCC(/C=N/CCC/N=C/C1=C/CC[C@@]3(C)O[C@H]3[C@H]3OC(=O)C(=C)[C@@H]3CC1)=C\CC[C@@]1(C)O[C@@H]21] | — |
| 70 | | 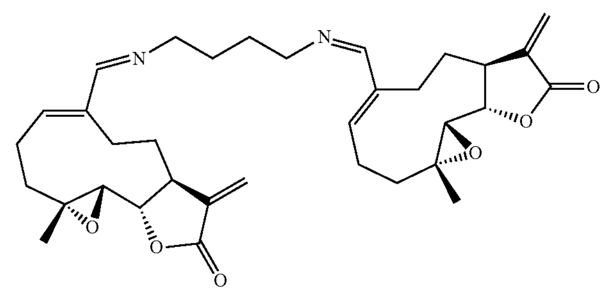 [SMILES: C=C1C(=O)O[C@H]2[C@H]1CCC(/C=N\CCCC/N=C/C1=C/CC[C@@]3(C)O[C@H]3[C@H]3OC(=O)C(=C)[C@@H]3CC1)=C\CC[C@@]1(C)O[C@@H]21] | — |
| 71 | | 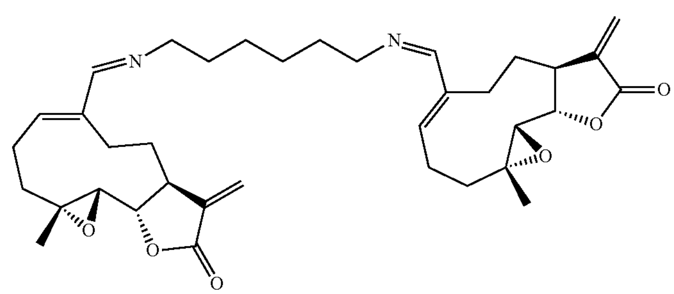 [SMILES: C=C1C(=O)O[C@H]2[C@H]1CCC(/C=N\CCCCCC/N=C/C1=C/CC[C@@]3(C)O[C@H]3[C@H]3OC(=O)C(=C)[C@@H]3CC1)=C\CC[C@@]1(C)O[C@@H]21] | — |

TABLE 5-continued

Exemplary Compounds.

| Line No. | Compound Name | Compound Structure | $EC_{50}$ (µM) |
|---|---|---|---|
| 72 | | 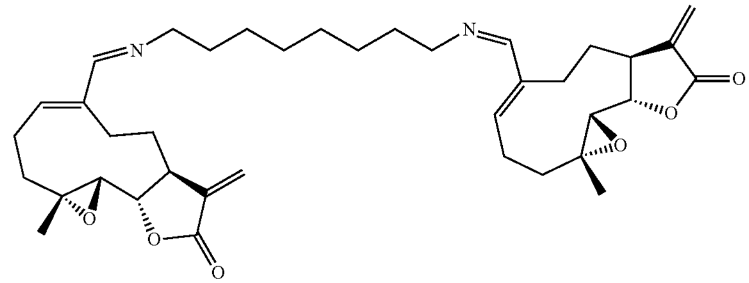 [SMILES: C=C1C(=O)O[C@H]2[C@H]1CCC(/C=N\CCCCCCCC/N=C/C1=C/CC[C@@]3(C)O[C@H]3[C@H]3OC(=O)C(=C)[C@@H]3CC1)=C\CC[C@@]1(C)O[C@@H]21] | — |
| 73 | | 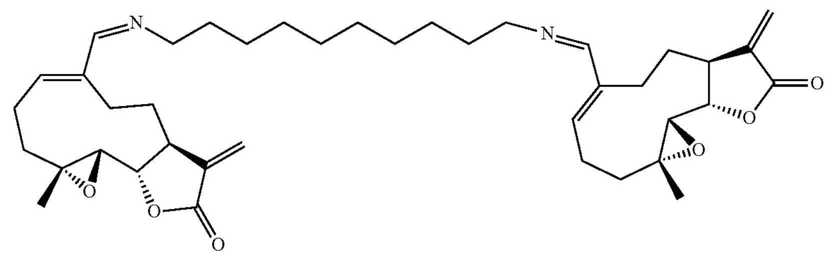 [SMILES: C=C1C(=O)O[C@H]2[C@H]1CC/C(C=NCCCCCCCCCC/N=C\C1=C\CC[C@@]3(C)O[C@H]3[C@H]3OC(=O)C(=C)[C@@H]3CC1)=C\CC[C@@]1(C)O[C@@H]21] | — |
| 74 | | 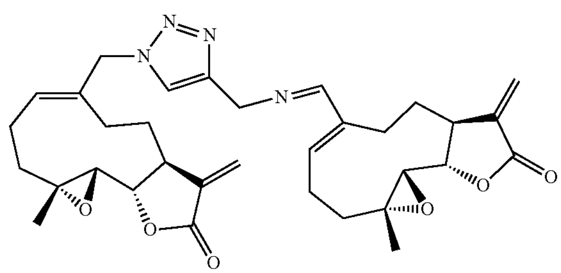 [SMILES: C=C1C(=O)O[C@H]2[C@H]1CC/C(C=NCc1cn(C/C3=C/CC[C@@]4(C)O[C@H]4[C@H]4OC(=O)C(=C)[C@@H]4CC3)nn1)=C\CC[C@@]1(C)O[C@@H]21] | — |
| 75 | | 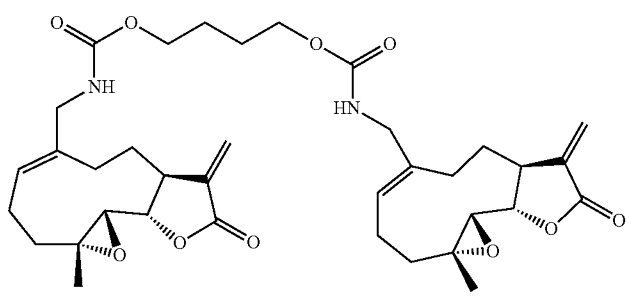 [SMILES: C=C1C(=O)O[C@H]2[C@H]1CC/C(CNC(=O)OCCCCOC(=O)NC/C1=C/CC[C@@]3(C)O[C@H]3[C@H]3OC(=O)C(=C)[C@@H]3CC1)=C\CC[C@@]1(C)O[C@@H]21] | — |
| 76 | | 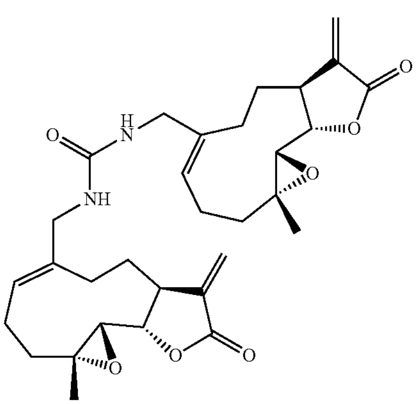 [SMILES: C=C1C(=O)O[C@H]2[C@H]1CC/C(CNC(=O)NC/C1=C/CC[C@@]3(C)O[C@H]3[C@H]3OC(=O)C(=C)[C@@H]3CC1)=C\CC[C@@]1(C)O[C@@H]21] | — |

TABLE 5-continued

Exemplary Compounds.

| Line No. | Compound Name | Compound Structure | EC$_{50}$ (μM) |
|---|---|---|---|
| 77 | | 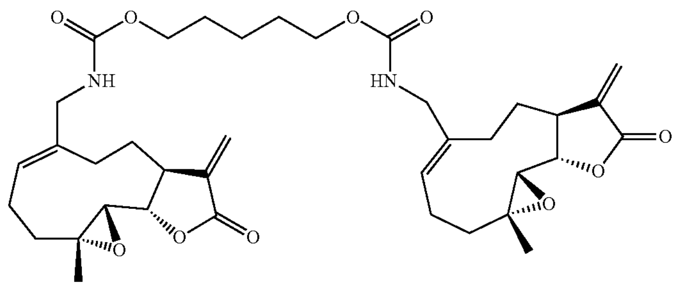 [SMILES: C=C1C(=O)O[C@H]2[C@H]1CC/C(CNC(=O)OCCCCCOC(=O)NC/C1=C/CC[C@@]3(C)O[C@H]3[C@H]3OC(=O)C(=C)[C@@H]3CC1)=C\CC[C@@]1(C)O[C@@H]21] | — |
| 78 | | 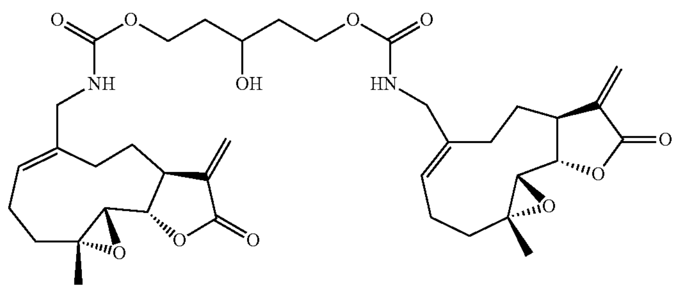 [SMILES: C=C1C(=O)O[C@H]2[C@H]1CC/C(CNC(=O)OCCC(O)CCOC(=O)NC/C1=C/CC[C@@]3(C)O[C@H]3[C@H]3OC(=O)C(=C)[C@@H]3CC1)=C\CC[C@@]1(C)O[C@@H]21] | — |
| 79 | | 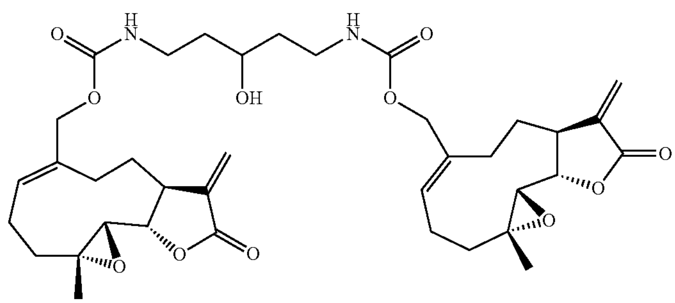 [SMILES: C=C1C(=O)O[C@H]2[C@H]1CC/C(COC(=O)NCCC(O)CCNC(=O)OC/C1=C/CC[C@@]3(C)O[C@H]3[C@H]3OC(=O)C(=C)[C@@H]3CC1)=C\CC[C@@]1(C)O[C@@H]21] | — |
| 80 | | 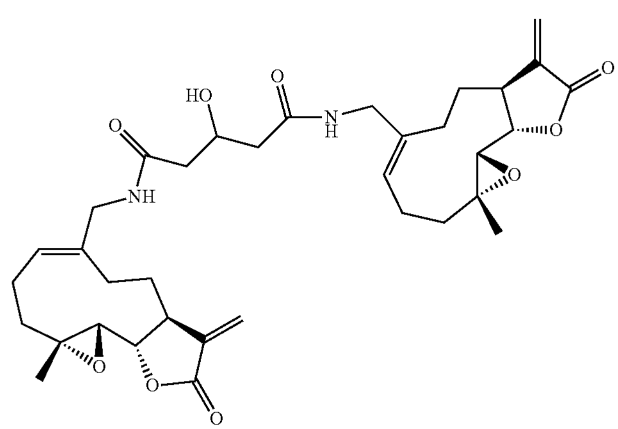 [SMILES: C=C1C(=O)O[C@H]2[C@H]1CC/C(CNC(=O)CC(O)CC(=O)NC/C1=C/CC[C@@]3(C)O[C@H]3[C@H]3OC(=O)C(=C)[C@@H]3CC1)=C\CC[C@@]1(C)O[C@@H]21] | — |

TABLE 5-continued

Exemplary Compounds.

| Line No. | Compound Name | Compound Structure | EC$_{50}$ (µM) |
|---|---|---|---|
| 81 | | 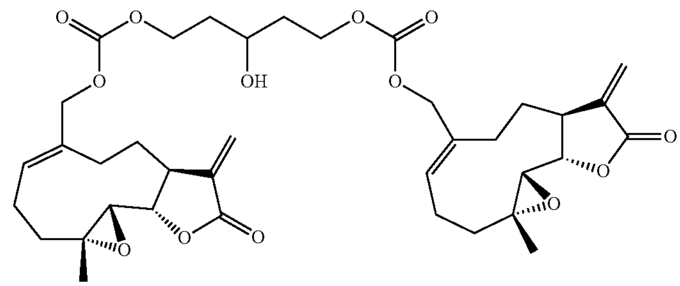 [SMILES: C=C1C(=O)O[C@H]2[C@H]1CC/C(COC(=O)OCCC(O)CCOC(=O)OC/C1=C/CC[C@@]3(C)O[C@H]3[C@H]3OC(=O)C(=C)[C@@H]3CC1)=C\CC[C@@]1(C)O[C@@H]21] | — |
| 82 | | 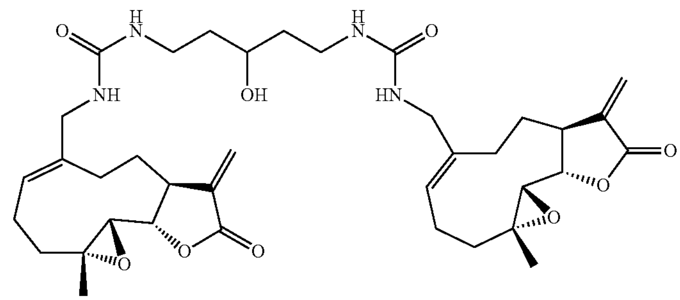 [SMILES: C=C1C(=O)O[C@H]2[C@H]1CC/C(CNC(=O)NCCC(O)CCNC(=O)NC/C1=C/CC[C@@]3(C)O[C@H]3[C@H]3OC(=O)C(=C)[C@@H]3CC1)=C\CC[C@@]1(C)O[C@@H]21] | — |
| 83 | | 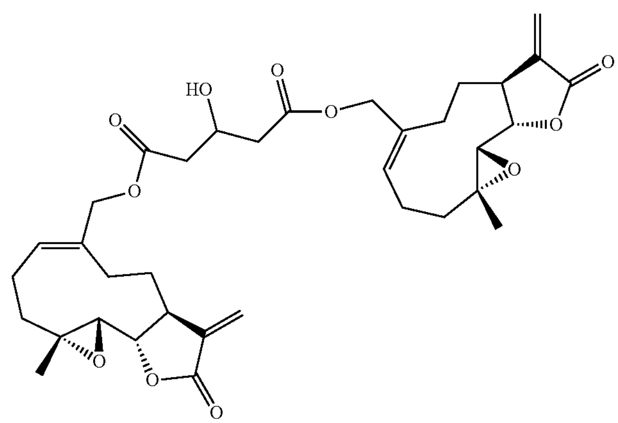 [SMILES: C=C1C(=O)O[C@H]2[C@H]1CC/C(COC(=O)CC(O)CC(=O)OC/C1=C/CC[C@@]3(C)O[C@H]3[C@H]3OC(=O)C(=C)[C@@H]3CC1)=C\CC[C@@]1(C)O[C@@H]21] | — |
| 84 | | 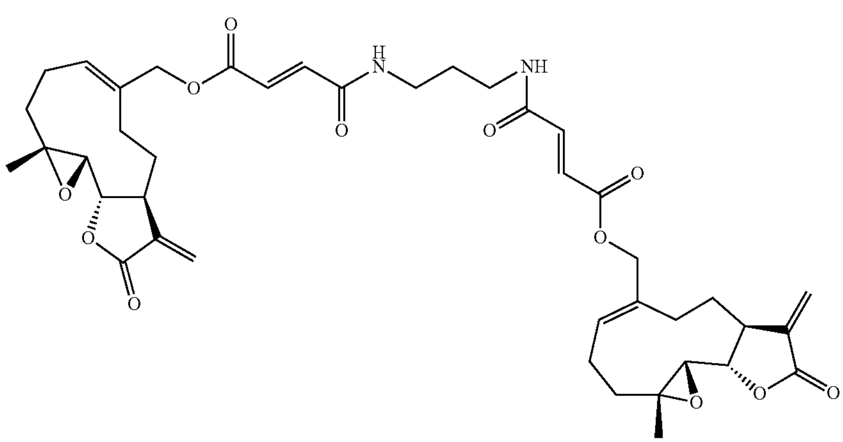 [SMILES: C=C1C(=O)O[C@H]2[C@H]1CC/C(COC(=O)/C=C/C(=O)NCCCNC(=O)/C=C/C(=O)OC/C1=C/CC[C@@]3(C)O[C@H]3[C@H]3OC(=O)C(=C)[C@@H]3CC1)=C\CC[C@@]1(C)O[C@@H]21] | — |

TABLE 5-continued

Exemplary Compounds.

| Line No. | Compound Name | Compound Structure | EC$_{50}$ (μM) |
|---|---|---|---|
| 85 | | 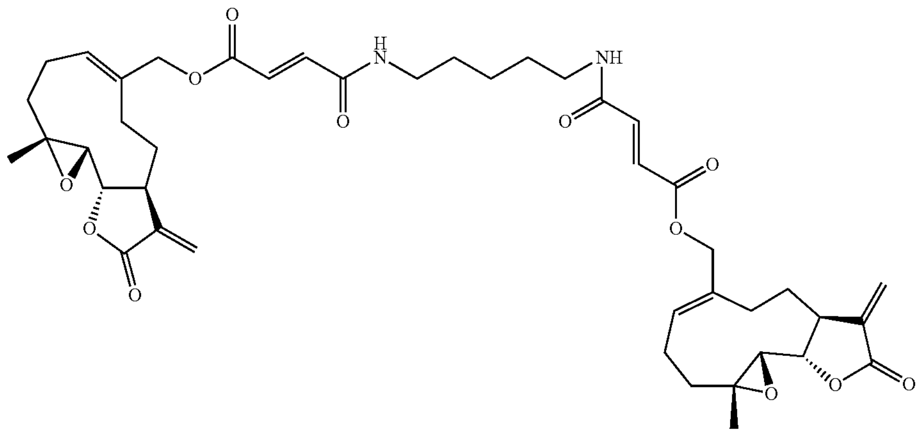 [SMILES: C=C1C(=O)O[C@H]2[C@H]1CC/C(COC(=O)/C=C/C(=O)NCCCCCNC(=O)/C=C/C(=O)OC/C1=C/CC[C@@]3(C)O[C@H]3[C@H]3OC(=O)C(=C)[C@@H]3CC1)=C\CC[C@@]1(C)O[C@@H]21] | — |
| 86 | | 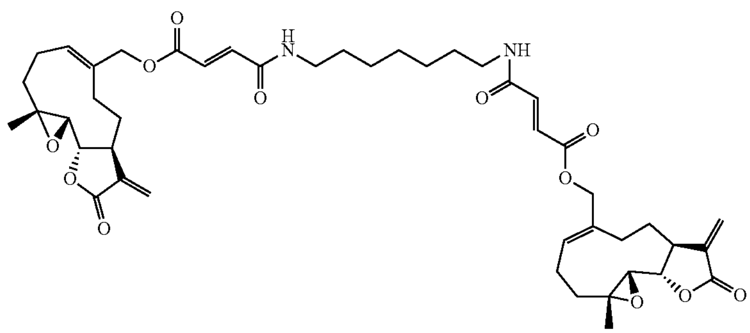 [SMILES: C=C1C(=O)O[C@H]2[C@H]1CC/C(COC(=O)/C=C/C(=O)NCCCCCCCNC(=O)/C=C/C(=O)OC/C1=C/CC[C@@]3(C)O[C@H]3[C@H]3OC(=O)C(=C)[C@@H]3CC1)=C\CC[C@@]1(C)O[C@@H]21] | — |
| 87 | | 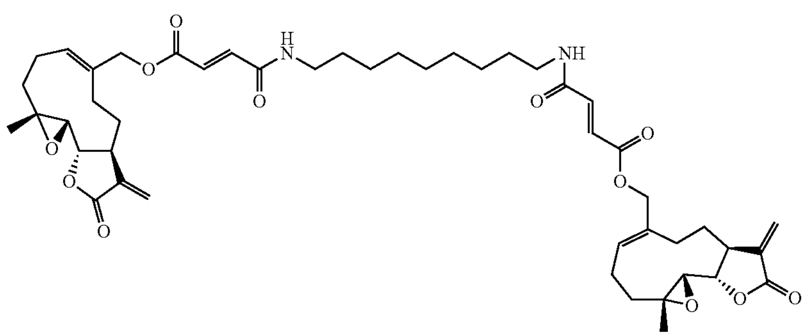 [SMILES: C=C1C(=O)O[C@H]2[C@H]1CC/C(COC(=O)/C=C/C(=O)NCCCCCCCCCNC(=O)/C=C/C(=O)OC/C1=C/CC[C@@]3(C)O[C@H]3[C@H]3OC(=O)C(=C)[C@@H]3CC1)=C\CC[C@@]1(C)O[C@@H]21] | — |
| 88 | | 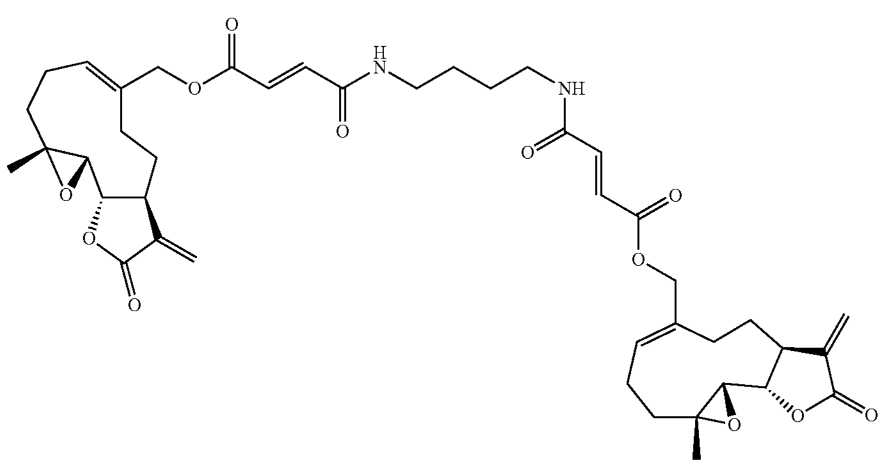 [SMILES: C=C1C(=O)O[C@H]2[C@H]1CC/C(COC(=O)/C=C/C(=O)NCCCCNC(=O)/C=C/C(=O)OC/C1=C/CC[C@@]3(C)O[C@H]3[C@H]3OC(=O)C(=C)[C@@H]3CC1)=C\CC[C@@]1(C)O[C@@H]21] | — |

TABLE 5-continued

Exemplary Compounds.

| Line No. | Compound Name | Compound Structure | EC$_{50}$ (μM) |
|---|---|---|---|
| 89 | | 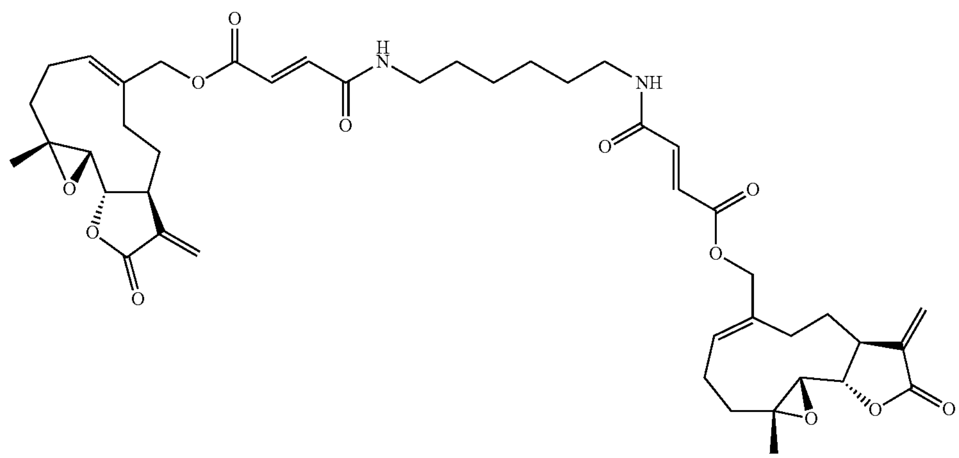 [SMILES: C=C1C(=O)O[C@H]2[C@H]1CC/C(COC(=O)/C=C/C(=O)NCCCCCCNC(=O)/C=C/C(=O)OC/C1=C/CC[C@@]3(C)O[C@H]3[C@H]3OC(=O)C(=C)[C@@H]3CC1)=C\CC[C@@]1(C)O[C@@H]21] | — |
| 90 | | 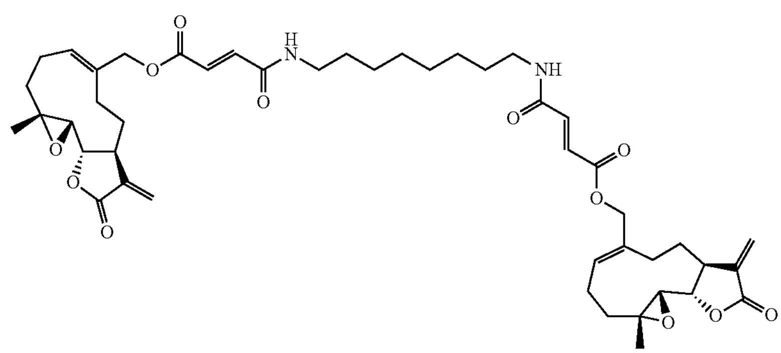 [SMILES: C=C1C(=O)O[C@H]2[C@H]1CC/C(COC(=O)/C=C/C(=O)NCCCCCCCCNC(=O)/C=C/C(=O)OC/C1=C/CC[C@@]3(C)O[C@H]3[C@H]3OC(=O)C(=C)[C@@H]3CC1)=C\CC[C@@]1(C)O[C@@H]21] | — |
| 91 | | 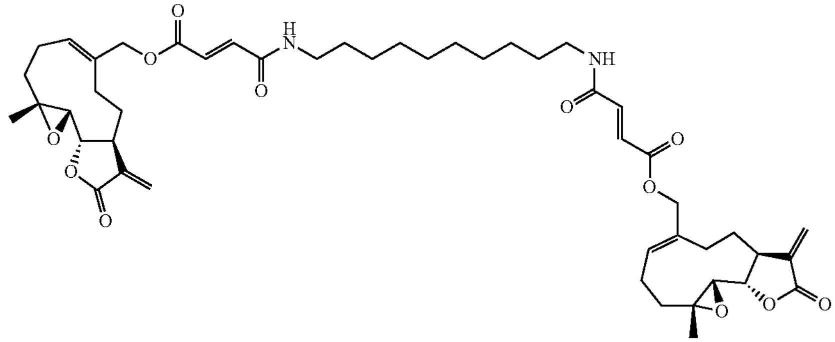 [SMILES: C=C1C(=O)O[C@H]2[C@H]1CC/C(COC(=O)/C=C/C(=O)NCCCCCCCCCCNC(=O)/C=C/C(=O)OC/C1=C/CC[C@@]3(C)O[C@H]3[C@H]3OC(=O)C(=C)[C@@H]3CC1)=C\CC[C@@]1(C)O[C@@H]21] | — |

What is claimed is:

1. A compound comprising Formula (I) or a pharmaceutical acceptable salt thereof:

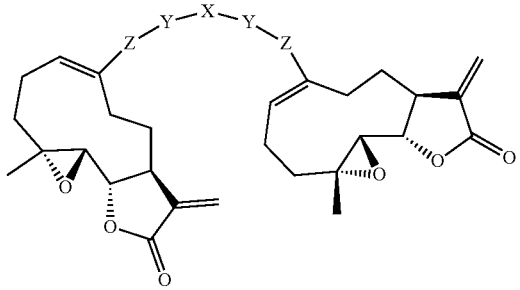

(I)

wherein:
Z is independently selected from the group consisting of CH₂, O, C(O), and CH, wherein when Z is CH, Z is connected to Y via a double bond and Y is N;
Y is independently selected from the group consisting of O, NR, N,

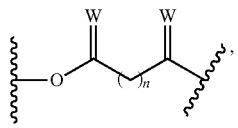

heterocycle, hydrocarbyl and substituted hydrocarbyl,

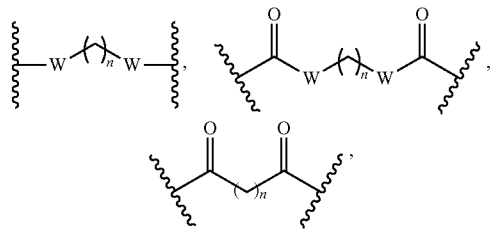

wherein R is selected from the group consisting of H, alkyl, hydrocarbyl and substituted hydrocarbyl and W is selected from the group consisting of O, S, NH, N-alkyl, heterocycle, alkyl, substituted alkyl, hydrocarbyl and substituted hydrocarbyl;
X is selected from the group consisting of (CH₂)ₙ, C(O), —(CH₂)ₙ—W—C(O)—, —C(O)—W—C(O)—, —C(O)NH—W—NHC(O)—, —C(O)O—W—OC(O)—, carbocycle, heterocycle, alkyl, substituted alkyl, hydrocarbyl and substituted hydrocarbyl;
wherein W is selected from the group consisting of O, S, NH, N-alkyl,
heterocycle, alkyl, substituted alkyl, hydrocarbyl and substituted hydrocarbyl; and
n is an integer from 0-10.

2. The compound of claim 1, wherein the compound comprises Formula (II) or a pharmaceutical acceptable salt thereof:

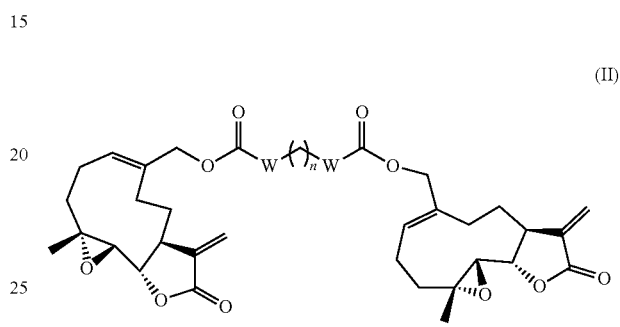

(II)

wherein:
X is selected from the group consisting of O or NH; and
n is an integer from 010.

3. A compound comprising Formula (III) or a pharmaceutical acceptable salt thereof:

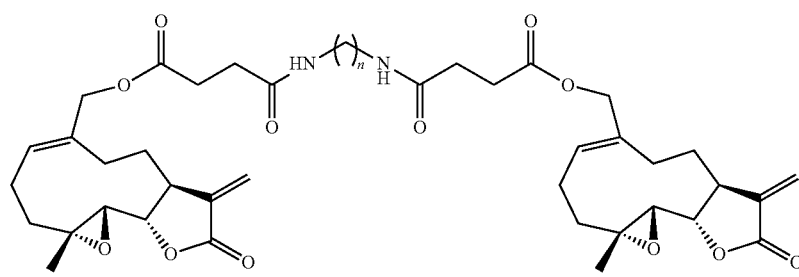

(III)

wherein:
n is an integer from 1-10.

4. The compound of claim 1, wherein the compound comprises Formula (IV):

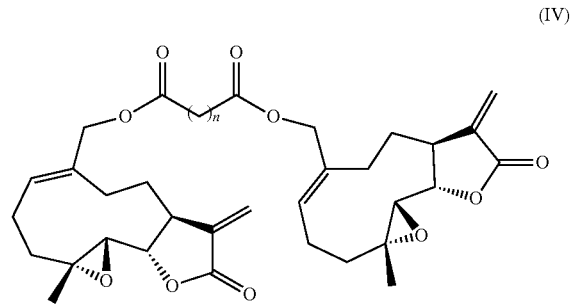

(IV)

wherein:
n is an integer from 1-10.

5. A compound comprising Formula (V) or a pharmaceutical acceptable salt thereof:

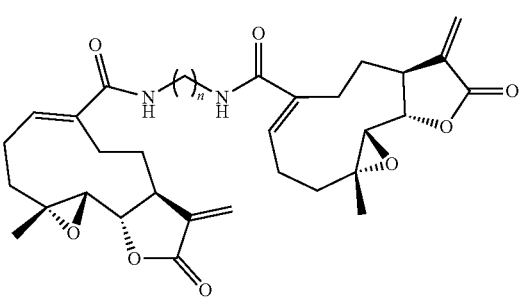

(V)

wherein:
n is an integer from 1-10.

6. The compound of claim 1, wherein the compounds comprising Formulas (I), (II), (III), (IV) or (V) independently have an optical activity of (−) or (+); and the configuration of C-4, C-5, C-6, and C-7, respectively, is RRRR, RRSR, RRRS, RRSS, RSRR, RSSR, RSRS, RSSS, SRRR, SRSR, SRRS, SRSS, SSRR, SSSR, SSRS, or SSSS.

7. The compound of claim 1, wherein Z is selected from the group consisting of CH$_2$ and C(O).

8. The compound of claim 1, wherein Y is selected from the group consisting of O, NR, and

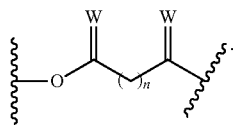

9. The compound of claim 8, wherein W is selected from the group consisting of O, S, NH, and N-alkyl.

10. The compound of claim 1, wherein X is selected from the group consisting of (CH$_2$)$_n$, C(O),

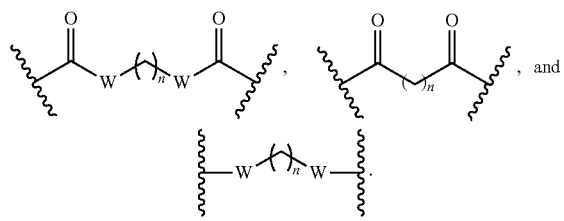

, and

11. The compound of claim 10, wherein W is selected from the group consisting of O, S, NH, and N-alkyl.

* * * * *